(12) United States Patent
Askew et al.

(10) Patent No.: US 6,693,101 B2
(45) Date of Patent: Feb. 17, 2004

(54) αV INTEGRIN RECEPTOR ANTAGONISTS

(75) Inventors: Ben C. Askew, Newbury Park, CA (US); Michael J. Breslin, Drexel Hill, PA (US); Mark E. Duggan, Schwenksville, PA (US); John H. Hutchinson, Philadelphia, PA (US); Robert S. Meissner, Schwenksville, PA (US); James J. Perkins, Churchville, PA (US); Thomas G. Steele, Schwenksville, PA (US); Michael A. Patane, Billerica, MA (US)

(73) Assignee: Merck & Co., Inc., Rahway, NJ (US)

( * ) Notice: Subject to any disclaimer, the term of this patent is extended or adjusted under 35 U.S.C. 154(b) by 159 days.

(21) Appl. No.: 09/767,471

(22) Filed: Jan. 23, 2001

(65) Prior Publication Data

US 2001/0053853 A1 Dec. 20, 2001

Related U.S. Application Data

(60) Provisional application No. 60/177,792, filed on Jan. 24, 2000, and provisional application No. 60/230,469, filed on Sep. 6, 2000.

(51) Int. Cl.[7] ............... A61K 31/44; C07D 239/02; C07D 471/02; C07D 513/00
(52) U.S. Cl. ............ 514/256; 514/212.02; 514/300; 544/316; 544/333; 544/335; 546/115; 546/118; 546/122; 546/123; 546/135; 540/521; 540/543; 540/577; 540/580
(58) Field of Search ............... 514/256, 300, 514/212.02; 544/333, 316, 353; 546/122, 123, 118, 115, 135; 540/521, 543, 577, 580

(56) References Cited

U.S. PATENT DOCUMENTS 5,652,363 A * 7/1997 Khanna et al. ............ 544/105
5,952,341 A 9/1999 Duggan et al.
6,048,861 A * 4/2000 Askew et al. .............. 514/256
6,297,249 B1 * 10/2001 Duggan et al. ............. 514/256
2002/0086882 A1 * 7/2002 Konradi et al. ............ 514/332

FOREIGN PATENT DOCUMENTS

WO     WO 99/31061     6/1999
WO     WO 00/72801 A2   12/2000

OTHER PUBLICATIONS

Duggan et al, "Ligands to the integrin receptor αvβ3", Expert Opinion on Therapeutic Patents, vol. 10, pp. 1367–1383 (2000).

Miller et al., "Identification and in vivo efficacy of small-molecule antagonists of integrin αvβ3 (the vitronectin receptor)", Drug Discovery Today, vol. 5, pp. 397–408 (2000).

Gowen et al., "Emerging therapies for osteoporosis", Emerging Drugs, vol. 5, pp. 1–43 (2000).

Kerr et al, "Small molecule αv integrin antagonists: novel anticancer agents", Expert Opinion on Investigational Drugs, vol. 9, pp. 1271–1279 (2000).

Hartman et al., "αvβ3Integrin antagonists as inhibitors of bone resorption", Expert Opinion on Investigational Drugs, vol. 9, pp. 1281–1291 (2000).

* cited by examiner

Primary Examiner—Richard L. Raymond
Assistant Examiner—Tamthom N. Truong
(74) Attorney, Agent, or Firm—Patricia A. Shatynski; Mark R. Daniel

(57) ABSTRACT

The present invention relates to novel alkanoic acid derivatives thereof, their synthesis, and their use as αv integrin receptor antagonists. More particularly, the compounds of the present invention are antagonists of the integrin receptors αvβ3 and/or αvβ5 and are useful for inhibiting bone resorption, treating and preventing osteoporosis, and inhibiting vascular restenosis, diabetic retinopathy, macular degeneration, angiogenesis, atherosclerosis, inflammatory arthritis, cancer, and metastatic tumor growth.

1 Claim, No Drawings

αV INTEGRIN RECEPTOR ANTAGONISTS

CROSS-REFERENCE TO RELATED APPLICATIONS

The present invention is related to U.S. provisional applications Serial No. 60/177,792, filed Jan. 24, 2000; and 60/230,469, filed Sep. 6, 2000, the contents of each of which are hereby incorporated by reference.

FIELD OF THE INVENTION

The present invention relates to alkanoic acid derivatives, their synthesis, and their use as αv integrin receptor antagonists. More particularly, the compounds of the present invention are antagonists of the integrin receptors αvβ3, αvβ5, and αv integrin receptors associated with other β-subunits, and are useful for inhibiting bone resorption, treating and preventing osteoporosis, and inhibiting vascular restenosis, diabetic retinopathy, macular degeneration, angiogenesis, atherosclerosis, inflammatory arthritis, cancer, and metastatic tumor growth.

BACKGROUND OF THE INVENTION

It is believed that a wide variety of disease states and conditions can be mediated by acting on integrin receptors and that integrin receptor antagonists represent a useful class of drugs. Integrin receptors are heterodimeric transmembrane receptors through which cells attach and communicate with extracellular matrices and other cells. (See S. B. Rodan and G. A. Rodan, "Integrin Function In Osteoclasts," *Journal of Endocrinology*, 154: S47–S56 (1997), which is incorporated by reference herein in its entirety).

In one aspect of the present invention, the compounds herein are useful for inhibiting bone resorption. Bone resorption is mediated by the action of cells known as osteoclasts. Osteoclasts are large multinucleated cells of up to about 400 mm in diameter that resorb mineralized tissue, chiefly calcium carbonate and calcium phosphate, in vertebrates. Osteoclasts are actively motile cells that migrate along the surface of bone, and can bind to bone, secrete necessary acids and proteases, thereby causing the actual resorption of mineralized tissue from the bone. More specifically, osteoclasts are believed to exist in at least two physiological states, namely, the secretory state and the migratory or motile state. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone.

Integrins are involved in osteoclast attachment, activation and migration. The most abundant integrin on osteoclasts, e.g., on rat, chicken, mouse and human osteoclasts, is an integrin receptor known as αvβ3, which is thought to interact in bone with matrix proteins that contain the RGD sequence. Antibodies to αvβ3 block bone resorption in vitro indicating that this integrin plays a key role in the resorptive process. There is increasing evidence to suggest that αvβ3 ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, αvβ3 ligands have been found to be useful in treating and/or inhibiting restenosis (i.e. recurrence of stenosis after corrective surgery on the heart valve), atherosclerosis, diabetic retinopathy, macular degeneration, and angiogenesis (i.e. formation of new blood vessels), and inhibiting viral disease. Moreover, it has been postulated that the growth of tumors depends on an adequate blood supply, which in turn is dependent on the growth of new vessels into the tumor; thus, inhibition of angiogenesis can cause tumor regression in animal models (See *Harrison's Principles of Internal Medicine*, 12th ed., 1991, which is incorporated by reference herein in its entirety). Therefore, αvβ3 antagonists which inhibit angiogenesis can be useful in the treatment of cancer by inhibiting tumor growth (See, e.g., Brooks et al., *Cell*, 79:1157–1164 (1994), which is incorporated by reference herein in its entirety).

Evidence has also been presented suggesting that angiogenesis is a central factor in the initiation and persistence of arthritic disease, and that the vascular integrin αvβ3 may be a preferred target in inflammatory arthritis. Therefore, αvβ3 antagonists which inhibit angiogenesis may represent a novel therapeutic approach to the treatment of arthritic disease, such as rheumatoid arthritis (see C. M. Storgard, et al, "Decreased angiogenesis and arthritic disease in rabbits treated with an αvβ3 antagonist," *J. Clin. Invest.*, 103: 47–54 (1999), which is incorporated by reference herein in its entirety).

Moreover, compounds of this invention can also inhibit neovascularization by acting as antagonists of the integrin receptor, αvβ5. A monoclonal antibody for αvβ5 has been shown to inhibit VEGF-induced angiogenesis in rabbit cornea and the chick chorioallantoic membrane model (See M. C. Friedlander, et al., *Science* 270: 1500–1502 (1995), which is incorporated by reference herein in its entirety). Thus, compounds that antagonize αvβ5 are useful for treating and preventing macular degeneration, diabetic retinopathy, viral disease, cancer, and metastatic tumor growth.

Additionally, compounds of the instant invention can inhibit angiogenesis and inflammation by acting as antagonists of αv integrin receptors associated with other β subunits, suh as αvβ6 and αvβ8 (See, for example, Melpo Christofidou-Solomidou, et al., "Expression and Function of Endothelial Cell αv Integrin Receptors in Wound-Induced Human Angiogenesis in Human Skin/SCID Mice Chimeras," *American Journal of Pathology*, 151: 975–83 (1997) and Xiao-Zhu Huang, et al., "Inactivation of the Integrin β6 Subunit Gene Reveals a Role of Epithelial Integrins in Regulating Inflammation in the Lungs and Skin," *Journal of Cell Biology*, 133: 921–28 (1996), which are incorporated by reference herein in their entirety).

In addition, certain compounds of this invention antagonize both the αvβ3 and αvβ5 receptors. These compounds, referred to as "dual αvβ3/αvβ5 antagonists," are useful for inhibiting bone resorption, treating and preventing osteoporosis, and inhibiting vascular restenosis, diabetic retinopathy, macular degeneration, angiogenesis, atherosclerosis, inflammatory arthritis, cancer, and metastatic tumor growth.

Peptidyl as well as peptidomimetic antagonists of the αvvβ3 integrin receptor have been described both in the scientific and patent literature. For example, reference is made to W. J. Hoekstra and B. L. Poulter, *Curr. Med. Chem.* 5: 195–204 (1998) and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; EP 853084; EP 854140; EP 854145; and U.S. Pat. No. 5,780,426. Evidence of the ability of αvβ3 integrin receptor antagonists to prevent bone resorption in vitro and in vivo has been presented (see V. W. Engleman et al., "A Peptidomimetic Antagonist of the αvβ3 Integrin Inhibits Bone Resorption in Vitro and Prevents Osteoporosis in Vivo," *J. Clin. Invest.* 99: 2284–2292 (1997); S. B. Rodan et al., "A High Affinity Non-Peptide αvβ3 Ligand Inhibits Osteoclast Activity In Vitro and In Vivo," *J. Bone Miner. Res.* 11: S289 (1996); J. F. Gourvest et al., "Prevention of OVX-Induced Bone Loss With a Non-peptidic Ligand of the αvβ3 Vitronectin Receptor," *Bone* 23: S612 (1998); M. W. Lark et al., "An Orally Active Vitronectin Receptor αvβ3 Antagonist Prevents Bone Resorption In Vitro and In Vivo in the Ovariectomized Rat," *Bone* 23: S219 (1998)).

The αvβ3 integrin receptor recognizes the Arg-Gly-Asp (RGD) tripeptide sequence in its cognate matrix and cell surface glycoproteins (see J. Samanen, et al., "Vascular Indications for Integrin αv Antagonists," *Curr. Pharmaceut. Design* 3: 545–584 (1997)). A benzazepine nucleus has been employed among others by Genentech and SmithKline Beecham as a conformationally constrained Gly-Asp mimetic to elaborate nonpeptide αvβ3 integrin receptor antagonists substituted at the N-terminus with heterocyclic arginine mimetics (see R. M. Keenan et al., "Discovery of Potent Nonpeptide Vitronectin Receptor (αvβ3) Antagonists," *J. Med. Chem.* 40: 2289–2292 (1997); R. M. Keenan et al., "Benzimidazole Derivatives As Arginine Mimetics in 1,4-Benzodiazepine Nonpeptide Vitronectin Receptor (αvβ3) Antagonists," *Bioorg. Med. Chem. Lett.* 8: 3165–3170 (1998); and R. M. Keenan et al., "Discovery of an Imidazopyridine-Containing 1,4-Benzodiazepine Nonpeptide Vitronectin Receptor (αvβ3) Antagonist With Efficacy in a Restenosis Model," *Bioorg. Med. Chem. Lett.* 8: 3171–3176 (1998). Patents assigned to SmithKline Beecham that disclose such benzazepine, as well as related benzodiazepine and benzocycloheptene, αvβ3 integrin receptor antagonists include WO 96/00574, WO 96/00730, WO 96/06087, WO 96/26190, WO 97/24119, WO 97/24122, WO 97/24124, WO 98/15278, WO 99/05107, WO 99/06049, WO 99/15170, and WO 99/15178, and to Genentech include WO 97/34865. The dibenzocycloheptene, as well as dibenzoxazepine, nucleus has also been employed as a Gly-Asp mimetic to afford αvβ3 antagonists (see WO 97/01540, WO 98/30542, WO 99/11626, and WO 99/15508 all assigned to SmithKline Beecham).

Other integrin receptor antagonists featuring backbone conformational ring constraints have been described in WO 99/30709; WO 99/30713; WO 99/31099; U.S. Pat. No. 5,919,792; U.S. Pat. No. 5,925,655; and U.S. Pat. No. 5,981,546.

However, there still remains a need for small-molecule, non-peptidic selective αv integrin receptor antagonists that display improved potency, pharmacodynamic, and pharmacokinetic properties, such as oral bioavailability and duration of action, over already described compounds. Such compounds would prove to be useful for the treatment, prevention, or suppression of various pathologies enumerated above that are mediated by αv integrin receptor binding and cell adhesion and activation.

In U.S. Ser. No. 09/212,082, (PCT application WO 99/31061, published Jun. 24, 1999), we disclosed a series of 3-substituted straight-chain alkanoic acid derivatives which are potent αvβ3 integrin receptor antagonists. In the present invention, we describe novel straight-chain alkanoic acid derivatives, which are substituted at the N-terminus with novel optionally substituted heterocycles and at C-3 with an optionally substituted aryl group. The compounds of the present invention exhibit improved in vivo pharmacokinetic and/or pharmacodynamic properties over the prior art compounds.

It is therefore an object of the present invention to provide novel straight-chain alkanoic acid derivatives which are useful as αv integrin receptor antagonists.

It is another object of the present invention to provide novel straight-chain alkanoic acid derivatives which are useful as αvβ3 receptor antagonists.

It is another object of the present invention to provide novel straight-chain alkanoic acid derivatives which are useful as αvβ5 receptor antagonists.

It is another object of the present invention to provide novel straight-chain alkanoic acid derivatives which are useful as dual αvβ3/αvβ5 receptor antagonists.

It is another object of the present invention to provide pharmaceutical compositions comprising αv integrin receptor antagonists.

It is another object of the present invention to provide methods for making the pharmaceutical compositions of the present invention.

It is another object of the present invention to provide methods for eliciting an αv integrin receptor antagonizing effect in a mammal in need thereof by administering the compounds and pharmaceutical compositions of the present invention.

It is another object of the present invention to provide compounds and pharmaceutical compositions useful for inhibiting bone resorption, restenosis, atherosclerosis, inflammatory arthritis, diabetic retinopathy, macular degeneration, angiogenesis, cancer, and metastatic tumor growth.

It is another object of the present invention to provide compounds and pharmaceutical compositions useful for treating osteoporosis.

It is another object of the present invention to provide methods for inhibiting bone resorption, restenosis, atherosclerosis, inflammatory arthritis, diabetic retinopathy, macular degeneration, angiogenesis, cancer, and metastatic tumor growth.

5

It is another object of the present invention to provide methods for treating osteoporosis.

These and other objects will become readily apparent from the detailed description which follows.

SUMMARY OF THE INVENTION

The present invention relates to novel alkanoic acid derivatives represented by structural formula (I), or a pharmaceutically acceptable salt thereof, which are useful as αv integrin receptor antagonists.

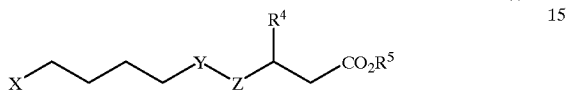

(I)

The present invention also relates to pharmaceutical compositions comprising the compounds of the present invention and a pharmaceutically acceptable carrier.

The present invention also relates to methods for making the pharmaceutical compositions of the present invention.

The present invention also relates to methods for eliciting an αv integrin receptor antagonizing effect in a mammal in need thereof by administering the compounds and pharmaceutical compositions of the present invention.

The present invention also relates to methods for inhibiting bone resorption, restenosis, atherosclerosis, inflammatory arthritis, diabetic retinopathy, macular degeneration, angiogenesis, cancer, and metastatic tumor growth by administering the compounds and pharmaceutical compositions of the present invention.

The present invention also relates to methods for treating osteoporosis by administering the compounds and pharmaceutical compositions of the present invention.

DETAILED DESCRIPTION OF THE INVENTION

The present invention relates to alkanoic acid derivatives useful as αv integrin receptor antagonists. Representative compounds of the present invention are described by the following structural formula (I):

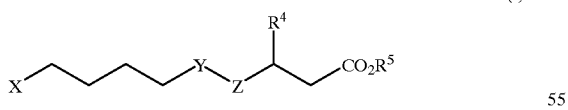

(I)

or a pharmaceutically acceptable salt thereof, wherein

X is selected from the group consisting of

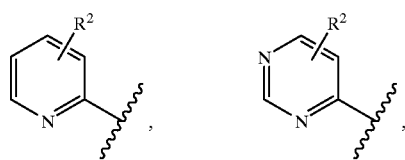

-continued

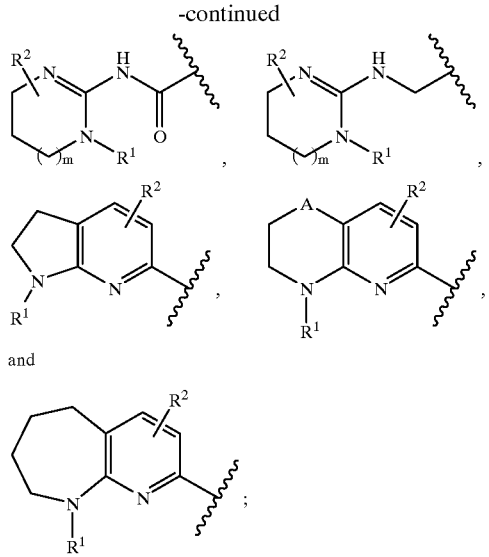

and

Y—Z is —$CH_2CH_2$— or —$CONR^3$—;

A is O or $NR^1$;

m is 0 or 1;

$R^1$ is hydrogen or $C_{1-3}$ alkyl;

each non-aromatic ring carbon atom is unsubstituted or independently substituted with one or two $R^2$ substituents and each aromatic ring carbon atom is unsubstituted or independently substituted with one $R^2$ substituent selected from the group consisting of $C_{1-8}$ alkyl, $C_{3-8}$ cycloalkyl, $C_{3-8}$ cycloheteroalkyl, $C_{3-8}$ cycloalkyl-$C_{1-6}$ alkyl, $C_{3-8}$ cycloheteroalkyl-$C_{1-6}$ alkyl, aryl, aryl-$C_{1-6}$ alkyl, amino, amino-$C_{1-6}$ alkyl, $C_{1-3}$ acylamino, $C_{1-3}$ acylamino-$C_{1-6}$ alkyl, ($C_{1-6}$ alkyl)$_{1-2}$ amino, $C_{3-6}$ cycloalkyl-$C_{0-2}$ amino, ($C_{1-6}$ alkyl)$_{1-2}$ amino-$C_{1-6}$ alkyl, $C_{1-6}$ alkoxy, $C_{1-4}$ alkoxy-$C_{1-6}$ alkyl, hydroxycarbonyl, hydroxycarbonyl-$C_{1-6}$ alkyl, $C_{1-3}$ alkoxycarbonyl, $C_{1-3}$ alkoxycarbonyl-$C_{1-6}$ alkyl, hydroxy, hydroxy-$C_{1-6}$ alkyl, nitro, cyano, trifluoromethyl, trifluoromethoxy, trifluoroethoxy, $C_{1-8}$ alkyl-$S(O)_{0-2}$, ($C_{1-8}$ alkyl)$_{0-2}$ aminocarbonyl, $C_{1-8}$ alkyloxycarbonylamino, ($C_{1-8}$ alkyl)$_{1-2}$ aminocarbonyloxy, (aryl $C_{1-3}$ alkyl)$_{1-2}$ amino, (aryl)$_{1-2}$ amino, aryl-$C_{1-3}$ alkylsulfonylamino, and $C_{1-8}$ alkylsulfonylamino;

or two $R^2$ substituents, when on the same non-aromatic carbon atom, are taken together with the carbon atom to which they are attached to form a carbonyl group; or two $R^2$ substituents, together with the carbon atoms to which they are attached, join to form a 3- to 6-membered saturated spiro-carbocyclic ring;

$R^3$ is hydrogen or $C_{1-4}$ alkyl;

$R^4$ is aryl wherein the aryl group is selected from the group consisting of (1) phenyl,
(2) naphthyl,
(3) pyridinyl,
(4) furyl, (5) thienyl,
(6) pyrrolyl,
(7) oxazolyl,
(8) thiazolyl,
(9) imidazolyl,
(10) pyrazolyl,
(11) isoxazolyl,
(12) isothiazolyl,
(13) pyrimidinyl,
(14) pyrazinyl,
(15) pyridazinyl,
(16) quinolyl,
(17) isoquinolyl,
(18) benzimidazolyl,
(19) benzofuryl,
(20) benzothienyl,
(21) indolyl,
(22) benzthiazolyl,
(23) benzoxazolyl,
(24) dihydrobenzofuryl,
(25) benzo(1,3)dioxolanyl,
(26) benzo(1,4)dioxanyl, and
(27) quinoxalinyl;

and mono, di, and tri-substituted aryl wherein aryl is as defined above and the substituents are independently hydrogen, hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino-$C_{1-6}$ alkyl, di($C_{1-6}$)alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl-$C_{1-6}$ alkyl, $C_{1-5}$ alkylcarbonyloxy, cyano, trifluoromethyl, 1,1,1-trifluoroethyl, trifluoromethoxy, trifluoroethoxy, or nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl; and $R^5$ is hydrogen or $C_{1-3}$ alkyl.

In one embodiment of the present invention, X is selected from the group consisting of

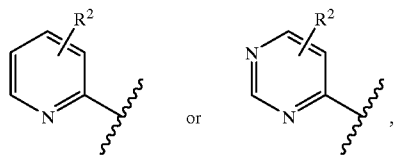

and Y is —$CH_2CH_2$—.

In a second embodiment of the present invention, $R^4$ is mono- or di-substituted
phenyl,
pyridinyl,
quinolyl,
pyrimidinyl,
pyrazinyl,
quinoxalinyl, or
dihydrobenzofuryl;
wherein the substituents are independently hydrogen, hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino-$C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino $C_{1-6}$ alkyl, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl $C_{1-6}$ alkyl, $C_{1-5}$ alkylcarbonyloxy, cyano, trifluoromethyl, 1,1,1-trifluoroethyl, trifluoromethoxy, trifluoroethoxy, or nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl.

In a class of this second embodiment of the present invention, $R^4$ is mono- or di-substituted
pyridinyl,
quinolyl,
pyrimidinyl,
pyrazinyl,
quinoxalinyl, or
dihydrobenzofuryl;
wherein the substituents are independently hydrogen, halogen, phenyl, $C_{1-4}$ alkyl, $C_{3-6}$ cycloalkyl, $C_{1-3}$ alkoxy, amino, $C_{1-3}$ alkylamino, di($C_{1-3}$) alkylamino, hydroxy, cyano, trifluoromethyl, 1,1,1-trifluoroethyl, trifluoromethoxy, or trifluoroethoxy.

In a third embodiment of the present invention, $R^2$ is selected from the group consisting of
hydrogen,
amino,
$C_{1-4}$ alkylamino,
$C_{3-6}$ cycloalkyl-$C_{0-2}$ alkylamino
cyano,
$C_{1-4}$ alkyl,
cyclopropyl,
aryl $C_{1-3}$ alkyl,
$C_{1-4}$ acylamino,
$C_{1-4}$ alkoxy,
$C_{1-4}$ alkylthio,
aminocarbonyl,
($C_{1-6}$ alkyl)$_{1-2}$ aminocarbonyl,
$C_{1-4}$ alkoxycarbonyl,
trifluoromethyl, and
trifluoromethoxy.

In a class of this third embodiment of the present invention, $R^2$ is selected from the group consisting of
hydrogen,
amino,
$C_{1-3}$ alkylamino,
$C_{3-6}$ cycloalkylmethylamino,
$C_{1-4}$ alkyl,
cyclopropyl,
trifluoromethyl, and
trifluoromethoxy.

Illustrative but nonlimiting examples of compounds of the present invention that are useful as αv integrin receptor antagonists are the following:

{[5-(2,4-Diaminopyrimidin-6-yl)pentanoyl]-(N-methyl) amino}-3-(6-methoxypyridin-3-yl)-propanoic acid;

{[5-(2,4-Diaminopyrimidin-6-yl)pentanoyl]-(N-methyl) amino-3(R)-(6-methoxypyridin-3-yl)-propanoic acid;

{[5-(2,4-Diaminopyrimidin-6-yl)pentanoyl]-(N-methyl)amino-3(S)-(6-methoxypyridin-3-yl)-propanoic acid;
{[5-(3-Amino-5,6,7,8-tetrahydroisoquinolin-1-yl)pentanoyl]-(N-methyl)amino}-3-(6-methoxypyridin-3-yl)-propanoic acid;
{[5-(3-Amino-5,6,7,8-tetrahydroisoquinolin-1-yl)pentanoyl]-(N-methyl)amino}-3(R)-(6-methoxypyridin-3-yl)-propanoic acid;
{[5-(3-Amino-5,6,7,8-tetrahydroisoquinolin-1-yl)pentanoyl]-(N-methyl)amino}-3(S)-(6-methoxypyridin-3-yl)-propanoic acid;
3-(5-3,4-Dihydro-2H-pyrido[3,2-b][1,4]oxazin-6-yl-pentanoylamino)-3-(quinolin-3-yl)-propionic acid;
3-(5-3,4-Dihydro-2H-pyrido[3,2-b][1,4]oxazin-6-yl-pentanoylamino)-3(R)-(quinolin-3-yl)-propionic acid;
3-(5-3,4-Dihydro-2H-pyrido[3,2-b][1,4]oxazin-6-yl-pentanoylamino)-3(S)-(quinolin-3-yl)-propionic acid;
3-(Quinolin-3-yl)-3-(5-1,2,3,4-tetrahydro-pyrido[2,3-b]pyrazin-6-yl-pentanoylamino)-propionic acid;
3(R)-(Quinolin-3-yl)-3-(5-1,2,3,4-tetrahydro-pyrido[2,3-b]pyrazin-6-yl-pentanoylamino)-propionic acid;
3(S)-(Quinolin-3-yl)-3-(5-1,2,3,4-tetrahydro-pyrido[2,3-b]pyrazin-6-yl-pentanoylamino)-propionic acid;
9-(6-Methylamino-pyridin-2-yl)-3-(pyrimidin-5-yl)-nonanoic acid;
9-(6-Methylamino-pyridin-2-yl)-3(R)-(pyrimidin-5-yl)-nonanoic acid;
9-(6-Methylamino-pyridin-2-yl)-3(S)-(pyrimidin-5-yl)-nonanoic acid;
9-(2,4-Diaminopyrimidin-6-yl)-3-(quinolin-3-yl)-nonanoic acid;
9-(2,4-Diaminopyrimidin-6-yl)-3(R)-(quinolin-3-yl)-nonanoic acid;
9-(2,4-Diaminopyrimidin-6-yl)-3(S)-(quinolin-3-yl)-nonanoic acid;
3(2-Methyl-pyrimidin-5-yl)-9-(6,7,8,9-tetrahydro-5H-pyrido[2,3-b]azepin-2-yl)-nonanoic acid;
3(R)-(2-Methyl-pyrimidin-5-yl)-9-(6,7,8,9-tetrahydro-5H-pyrido[2,3-b]azepin-2-yl)-nonanoic acid;
3(S)-(2-Methyl-pyrimidin-5-yl)-9-(6,7,8,9-tetrahydro-5H-pyrido[2,3-b]azepin-2-yl)-nonanoic acid;
3-Pyrimidin-5-yl-9-(6,7,8,9-tetrahydro-5H-pyrido [2,3-b]azepin-2-yl)-nonanoic acid;
3(R)-Pyrimidin-5-yl-9-(6,7,8,9-tetrahydro-5H-pyrido[2,3-b]azepin-2-yl)-nonanoic acid;
3(S)-Pyrimidin-5-yl-9-(6,7,8,9-tetrahydro-5H-pyrido[2,3-b]azepin-2-yl)-nonanoic acid;
(2-Methyl-pyrimidin-5-yl)-9-(1,4,5,6-tetrahydro-pyrimidin-2-ylcarbamoyl)-nonanoic acid;
3(R)-(2-Methyl-pyrimidin-5-yl)-9-(1,4,5,6-tetrahydro-pyrimidin-2-ylcarbamoyl)-nonanoic acid;
3(S)-(2-Methyl-pyrimidin-5-yl)-9-(1,4,5,6-tetrahydro-pyrimidin-2-ylcarbamoyl)-nonanoic acid;
9-(6-Methylamino-pyridin-2-yl)-3-(2-methyl-pyrimidin-5-yl)-nonanoic acid;
9-(6-Methylamino-pyridin-2-yl)-3(R)-(2-methyl-pyrimidin-5-yl)-nonanoic acid;
9-(6-Methylamino-pyridin-2-yl)-3(S)-(2-methyl-pyrimidin-5-yl)-nonanoic acid;
3-(2-Methoxy-pyrimidin-5-yl)-9-(6-methylamino-pyridin-2-yl)-nonanoic acid;
3(R)-(2-Methoxy-pyrimidin-5-yl)-9-(6-methylamino-pyridin-2-yl)-nonanoic acid;
3(S)-(2-Methoxy-pyrimidin-5-yl)-9-(6-methylamino-pyridin-2-yl)-nonanoic acid;
3-(2-Ethoxy-pyrimidin-5-yl)-9-(6-methylamino-pyridin-2-yl)-nonanoic acid;
3(R)-(2-Ethoxy-pyrimidin-5-yl)-9-(6-methylamino-pyridin-2-yl)-nonanoic acid;
3(S)-(2-Ethoxy-pyrimidin-5-yl)-9-(6-methylamino-pyridin-2-yl)-nonanoic acid;
9-(6-Ethylamino-pyridin-2-yl)-3-(2-methyl-pyrimidin-5-yl)-nonanoic acid;
9-(6-Ethylamino-pyridin-2-yl)-3(R)-(2-methyl-pyrimidin-5-yl)-nonanoic acid;
9-(6-Ethylamino-pyridin-2-yl)-3(S)-(2-methyl-pyrimidin-5-yl)-nonanoic acid;
3-(2-Methoxy-pyrimidin-5-yl)-9-(6-ethylamino-pyridin-2-yl)-nonanoic acid;
3(R)-(2-Methoxy-pyrimidin-5-yl)-9-(6-ethylamino-pyridin-2-yl)-nonanoic acid;
3(S)-(2-Methoxy-pyrimidin-5-yl)-9-(6-ethylamino-pyridin-2-yl)-nonanoic acid;
3-(2-Ethoxy-pyrimidin-5-yl)-9-(6-ethylamino-pyridin-2-yl)-nonanoic acid;
3(R)-(2-Ethoxy-pyrimidin-5-yl)-9-(6-ethylamino-pyridin-2-yl)-nonanoic acid;
3(S)-(2-Ethoxy-pyrimidin-5-yl)-9-(6-ethylamino-pyridin-2-yl)-nonanoic acid;
9-(4-Amino-2-ethylaminopyrimidin-6-yl)-3-(dihydrobenzofuran-6-yl)-nonanoic acid;
9-(4-Amino-2-ethylaminopyrimidin-6-yl)-3 (R)-(dihydrobenzofuran-6-yl)-nonanoic acid;
9-(4-Amino-2-ethylaminopyrimidin-6-yl)-3 (S)-(dihydrobenzofuran-6-yl)-nonanoic acid;
9-(4-Amino-2-ethylaminopyrimidin-6-yl)-3-(6-methoxypyridin-3-yl)nonanoic acid;
9-(4-Amino-2-ethylaminopyrimidin-6-yl)-3(R)-(6-methoxypyridin-3-yl)nonanoic acid;
9-(4-Amino-2-ethylaminopyrimidin-6-yl)-3(S)-(6-methoxypyridin-3-yl)nonanoic acid;
9-(4-Amino-2-ethylaminopyrimidin-6-yl)-3-(2-methoxypyrimidin-5-yl)nonanoic acid;
9-(4-Amino-2-ethylaminopyrimidin-6-yl)-3(R)-(2-methoxypyrimidin-5-yl)nonanoic acid;
9-(4-Amino-2-ethylaminopyrimidin-6-yl)-3(S)-(2-methoxypyrimidin-5-yl)nonanoic acid;
9-(4-Amino-2-ethylaminopyrimidin-6-yl)-3-(2-ethoxypyrimidin-5-yl)nonanoic acid;
9-(4-Amino-2-ethylaminopyrimidin-6-yl)-3(R)-(2-ethoxypyrimidin-5-yl)nonanoic acid;
9-(4-Amino-2-ethylaminopyrimidin-6-yl)-3(S)-(2-ethoxypyrimidin-5-yl)nonanoic acid;
9-(4-Amino-2-ethylaminopyrimidin-6-yl)-3-(2-methylpyrimidin-5-yl)nonanoic acid;
9-(4-Amino-2-ethylaminopyrimidin-6-yl)-3(R)-(2-methoylpyrimidin-5-yl)nonanoic acid;
9-(4-Amino-2-ethylaminopyrimidin-6-yl)-3(S)-(2-ethylpyrimidin-5-yl)nonanoic acid;
9-(4-Amino-2-ethylaminopyrimidin-6-yl)-3-(quinoxalin-2-yl)nonanoic acid;
9-(4-Amino-2-ethylaminopyrimidin-6-yl)-3(R)-(quinoxalin-2-yl)nonanoic acid;
9-(4-Amino-2-ethylaminopyrimidin-6-yl)-3(S)-(quinoxalin-2-yl)nonanoic acid;
9-(2-Amino-4-ethylaminopyrimidin-6-yl)-3-(2-ethoxypyrimidin-5-yl)nonanoic acid;
9-(2-Amino-4-ethylaminopyrimidin-6-yl)-3(R)-(2-ethoxypyrimidin-5-yl)nonanoic acid;
9-(2-Amino-4-ethylaminopyrimidin-6-yl)-3(S)-(2-ethoxypyrimidin-5-yl)nonanoic acid;
9-(4-Amino-2-aminopyrimidin-6-yl)-3-(2-methylpyrimidin-5-yl)nonanoic acid;
9-(4-Amino-2-aminopyrimidin-6-yl)-3(R)-(2-methylpyrimidin-5-yl)nonanoic acid;

9-(4-Amino-2-aminopyrimidin-6-yl)-3(S)-(2-methylpyrimidin-5-yl)nonanoic acid;
9-(2-Ethylaminopyrimidin-6-yl)-3-(2-ethoxypyrimidin-5-yl)nonanoic acid;
9-(2-Ethylaminopyrimidin-6-yl)-3(R)-(2-ethoxypyrimidin-5-yl)nonanoic acid;
9-(2-Ethylaminopyrimidin-6-yl)-3(S)-(2-ethoxypyrimidin-5-yl)nonanoic acid;
9-(6-Methylamino-pyridin-2-yl)-3-quinoxalin-2-yl-nonanoic acid;
3(R)-9-(6Methylamino-pyridin-2-yl)-3-quinoxalin-2-yl-nonanoic acid;
3(S )-9-(6-Methylamino-pyridin-2-yl)-3-quinoxalin-2-yl-nonanoic acid;
9-(2,3-Dihydro-1H-pyrrolo[2,3-b]pyridin-6-yl)-3(2-methyl-pyrimidin-5-yl)-nonanoic acid;
3(R)-9-(2,3-Dihydro-1H-pyrrolo[2,3-b]pyridin-6-yl)-3-(2-methyl-pyrimidin-5-yl)-nonanoic acid;
3(S)-9-(2,3-Dihydro-1H-pyrrolo[2,3-b]pyridin-6-yl)-3-(2-methyl-pyrimidin-5-yl)-nonanoic acid; and
3-(2-Methyl-pyrimidin-5-yl)-10-(1,4,5,6-tetrahydro-pyrimidin-2-ylamino)-decanoic acid;
or a pharmaceutically acceptable salt thereof.

Further illustrative of the compounds of the present invention are the following:
{[5-(2,4-Diaminopyrimidin-6-yl)pentanoyl]-(N-methyl)amino-3(R)-(6-methoxypyridin-3-yl)-propanoic acid;
{[5-(2,4-Diaminopyrimidin-6-yl)pentanoyl]-(N-methyl)amino-3(S)-(6-methoxypyridin-3-yl)-propanoic acid;
{[5-(3-Amino-5,6,7,8-tetrahydroisoquinolin-1-yl)pentanoyl]-(N-methyl)amino}-3(R)-(6-methoxypyridin-3-yl)-propanoic acid;
{[5-(3-Amino-5,6,7,8-tetrahydroisoquinolin-1-yl)pentanoyl]-(N-methyl)amino}-3(S)-(6-methoxypyridin-3-yl)-propanoic acid;
3-(5-3,4-Dihydro-2H-pyrido[3,2-b][1,4]oxazin-6-yl-pentanoylamino)-3(R)-(quinolin-3-yl)-propionic acid;
3-(5-3,4-Dihydro-2H-pyrido[3,2-b][1,4]oxazin-6-yl-pentanoylamino)-3(S)-(quinolin-3-yl)-propionic acid;
3(R)-(Quinolin-3-yl)-3-(5-1,2,3,4-tetrahydro-pyrido[2,3-b]pyrazin-6-yl-pentanoylamino)-propionic acid;
3(S)-(Quinolin-3-yl)-3-(5-1,2,3,4-tetrahydro-pyrido[2,3-b]pyrazin-6-yl-pentanoylamino)-propionic acid;
9-(6-Methylamino-pyridin-2-yl)-3(R)-(pyrimidin-5-yl)-nonanoic acid;
9-(6-Methylamino-pyridin-2-yl)-3(S)-(pyrimidin-5-yl)-nonanoic acid;
9-(2,4-Diaminopyrimidin-6-yl)-3(R)-(quinolin-3-yl)-nonanoic acid;
9-(2,4-Diaminopyrimidin-6-yl)-3(S)-(quinolin-3-yl)-nonanoic acid;
3(R)-(2-Methyl-pyrimidin-5-yl)-9-(6,7,8,9-tetrahydro-5H-pyrido[2,3-b]azepin-2-yl)-nonanoic acid;
3(S)-(2-Methyl-pyrimidin-5-yl)-9-(6,7,8,9-tetrahydro-5H-pyrido[2,3-b]azepin-2-yl)-nonanoic acid;
3(R)-Pyrimidin-5-yl-9-(6,7,8,9-tetrahydro-5H-pyrido[2,3-b]azepin-2-yl)-nonanoic acid;
3(S)-Pyrimidin-5-yl-9-(6,7,8,9-tetrahydro-5H-pyrido[2,3-b]azepin-2-yl)-nonanoic acid;
3(R)-(2-Methyl-pyrimidin-5-yl)-9-(1,4,5,6-tetrahydro-pyrimidin-2-ylcarbamoyl)-nonanoic acid;
3(S)-(2-Methyl-pyrimidin-5-yl)-9-(1,4,5,6-tetrahydro-pyrimidin-2-ylcarbamoyl)-nonanoic acid;
9-(6-Methylamino-pyridin-2-yl)-3 (R)-(2-methyl-pyrimidin-5-yl)-nonanoic acid;
9-(6-Methylamino-pyridin-2-yl)-3(S)-(2-methyl-pyrimidin-5-yl)-nonanoic acid;
3(R)-(2-Methoxy-pyrimidin-5-yl)-9-(6-methylamino-pyridin-2-yl)-nonanoic acid;
3(S)-(2-Methoxy-pyrimidin-5-yl)-9-(6-methylamino-pyridin-2-yl)-nonanoic acid;
3(R)-(2-Ethoxy-pyrimidin-5-yl)-9-(6-methylamino-pyridin-2-yl)-nonanoic acid;
3(S)-(2-Ethoxy-pyrimidin-5-yl)-9-(6-methylamino-pyridin-2-yl)-nonanoic acid;
9-(6-Ethylamino-pyridin-2-yl)-3(R)-(2-methyl-pyrimidin-5-yl)-nonanoic acid;
9-(6-Ethylamino-pyridin-2-yl)-3(S)-(2-methyl-pyrimidin-5-yl)-nonanoic acid;
3(R)-(2-Methoxy-pyrimidin-5-yl)-9-(6-ethylamino-pyridin-2-yl)-nonanoic acid;
3(S)-(2-Methoxy-pyrimidin-5-yl)-9-(6-ethylamino-pyridin-2-yl)-nonanoic acid;
3(R)-(2-Ethoxy-pyrimidin-5-yl)-9-(6-ethylamino-pyridin-2-yl)-nonanoic acid;
3(S)-(2-Ethoxy-pyrimidin-5-yl)-9-(6-ethylamino-pyridin-2-yl)-nonanoic acid;
9-(4-Amino-2-ethylaminopyrimidin-6-yl)-3(R)-(dihydrobenzofuran-6-yl)-nonanoic acid;
9-(4-Amino-2-ethylaminopyrimidin-6-yl)-3(S)-(dihydrobenzofuran-6-yl)-nonanoic acid;
9-(4-Amino-2-ethylaminopyrimidin-6-yl) -3(R)-(6-methoxypyridin-3-yl)nonanoic acid;
9-(4-Amino-2-ethylaminopyrimidin-6-yl)-3(S)-(6-methoxypyridin-3-yl)nonanoic acid;
9-(4-Amino-2-ethylaminopyrimidin-6-yl)-3(R)-(2-methoxypyrimidin-5-yl)nonanoic acid;
9-(4-Amino-2-ethylaminopyrimidin-6-yl)-3(S)-(2-methoxypyrimidin-5-yl)nonanoic acid;
9-(4-Amino-2-ethylaminopyrimidin-6-yl)-3(R)-(2-ethoxypyrimidin-5-yl)nonanoic acid;
9-(4-Amino-2-ethylaminopyrimidin-6-yl)-3(S)-(2-ethoxypyrimidin-5-yl)nonanoic acid;
9-(4-Amino-2-ethylaminopyrimidin-6-yl)-3(R)-(2-methylpyrimidin-5-yl)nonanoic acid;
9-(4-Amino-2-ethylaminopyrimidin-6-yl)-3(S)-(2-methylpyrimidin-5-yl)nonanoic acid;
9-(4-Amino-2-ethylaminopyrimidin-6-yl)-3(R)-(quinoxalin-2-yl)nonanoic acid; 2-methylpyrimidin-5-yl) nonanoic acid;
9-(4-Amino-2-ethylaminopyrimidin-6-yl)-3(S)-(quinoxalin-2-yl)nonanoic acid;
9-(2-Amino-4-ethylaminopyrimidin-6-yl)-3(R)-(2-ethoxypyrimidin-5-yl)nonanoic acid;
9-(2-Amino-4-ethylaminopyrimidin-6-yl)-3(S)-(2-ethoxypyrimidin-5-yl)nonanoic acid;
9-(4-Amino-2-aminopyrimidin-6-yl)-3(R)-(2-methylpyrimidin-5-yl)nonanoic acid;
9-(4-Amino-2-aminopyrimidin-6-yl)-3(S)-(2-methylpyrimidin-5-yl)nonanoic acid;
9-(2-Ethylaminopyrimidin-6-yl)-3(R)-(2-ethoxypyrimidin-5-yl)nonanoic acid;
9-(2-Ethylaminopyrimidin-6-yl)-3(S)-(2-ethoxypyrimidin-5-yl)nonanoic acid;
3(R)-9-(6-Methylamino-pyridin-2-yl)-3-quinoxalin-2-yl-nonanoic acid;
3(S)-9-(6-Methylamino-pyridin-2-yl)-3-quinoxalin-2-yl-nonanoic acid;
3(R)-9-(2,3-Dihydro-1H-pyrrolo[2,3-b]pyridin-6-yl)-3-(2-methyl-pyrimidin-5-yl)-nonanoic acid; and
3(S)-9-(2,3-Dihydro-1H-pyrrolo[2,3-b]pyridin-6-yl)-3-(2-methyl-pyrimidin-5-yl)-nonanoic acid;
or a pharmaceutically acceptable salt thereof.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts of basic compounds encompassed within the term "pharmaceutically acceptable salts" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The compounds of the present invention can have chiral centers and can thus occur as racemates, racemic mixtures, single enantiomers, diastereomeric mixtures, and individual diastereomers, with all isomeric forms being included in the present invention. Therefore, where a compound is chiral, the separate enantiomers or diastereomers, substantially free of the other, are included within the scope of the invention; further included are all mixtures of the two enantiomers.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form, known as keto-enol tautomers. The individual tautomers as well as mixtures thereof are encompassed within the compounds of the present invention.

Compounds of the present invention may be separated into diastereoisomeric pairs of enantiomers by, for example, fractional crystallization from a suitable solvent, for example, methanol or ethyl acetate or a mixture thereof. The pair of enantiomers thus obtained may be separated into individual stereoisomers by conventional means, for example, by the use of an optically active acid as a resolving agent, or by HPLC using a chiral stationary phase. Alternatively, any enantiomer of a compound of the present invention may be obtained by stereospecific synthesis using optically pure starting materials or reagents of known configuration.

Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "$\alpha v$ integrin receptor antagonist," as used herein, refers to a compound which binds to and antagonizes either the $\alpha v \beta 3$ receptor or the $\alpha v \beta 5$ receptor, or a compound which binds to and antagonizes a combination of these receptors (for example, a dual $\alpha v \beta 3/\alpha v \beta 5$ receptor antagonist).

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O, or S. Examples of cycloheteroalkyl groups include, but are not limited to piperidinyl, pyrrolidinyl, azetidinyl, morpholinyl, piperazinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or bicyclic system comprising at least one aromatic ring, wherein the monocylic or bicyclic system contains 0, 1, 2, 3, or 4 heteroatoms chosen from N, O, or S, and wherein the monocylic or bicylic system is either unsubstituted or substituted with one or more groups independently selected from hydrogen, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino $C_{1-6}$ alkyl, $C_{1-6}$ alkylamino, $C_{1-6}$ alkylamino $C_{1-6}$ alkyl, di($C_{1-6}$) alkylamino, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, trifluoromethoxy, oxo or $C_{1-5}$ alkylcarbonyloxy. Examples of aryl include, but are not limited to, phenyl, naphthyl, pyridyl, pyrrolyl, pyrazolyl, pyrazinyl, pyrimidinyl, imidazolyl, benzimidazolyl, benzthiazolyl, benzoxazolyl, indolyl, thienyl, furyl, dihydrobenzofuryl, benzo(1,3)dioxolanyl, benzo(1,4)dioxanyl, oxazolyl, isoxazolyl, thiazolyl, and isothiazolyl, which are either unsubstituted or substituted with one or more groups independently selected from hydrogen, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino $C_{1-6}$ alkyl, $C_{1-6}$ alkylamino, $C_{1-6}$ alkylamino $C_{1-6}$ alkyl, di($C_{1-6}$) alkylamino, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, trifluoromethoxy, oxo, or $C_{1-5}$ alkylcarbonyloxy. Preferably, the aryl group is unsubstituted, mono-, di-, or tri-substituted with one to three of the above-named substituents; more preferably, the aryl group is unsubstituted, mono- or di-substituted with one to two of the above-named substituents.

Whenever the term "alkyl" or "aryl" or either of their prefix roots appears in a name of a substituent (e.g., aryl $C_{0-8}$ alkyl), it shall be interpreted as including those limitations given above for "alkyl" and "aryl." Designated numbers of carbon atoms (e.g., $C_{1-8}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

In the compounds of the present invention, two $R^2$ substituents, when on the same carbon atom, can be taken together with the carbon atom to which they are attached to form a carbonyl group.

The term "halogen" shall include iodine, bromine, chlorine, and fluorine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nonmenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

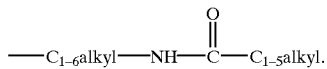

In choosing compounds of the present invention, one of ordinary skill in the art will recognize that the various substituents, i.e. X, Y, Z, $R^1$, $R^2$, $R^3$, $R^4$, and $R^5$ are to be chosen in conformity with well-known principles of chemical structure connectivity.

Representative compounds of the present invention typically display submicromolar affinity for the αv integrin receptors, particularly the αvβ3 and αvβ5. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the αvβ3 receptor where such treatment is needed, as, for example, in the prevention or treatment of osteoporosis.

Illustrating the invention is the method wherein the αv integrin receptor antagonizing effect is an αvβ3 antagonizing effect. More particularly, the αvβ3 antagonizing effect is selected from inhibition of: bone resorption, restenosis, angiogenesis, diabetic retinopathy, macular degeneration, inflammatory arthritis, cancer, or metastatic tumor growth. In one embodiment of the method, the αvβ3 antagonizing effect is the inhibition of bone resorption.

Another example of the invention is the method wherein the αv integrin receptor antagonizing effect is an αvβ5 antagonizing effect. More specifically, the αvβ5 antagonizing effect is selected from inhibition of restenosis, angiogenesis, diabetic retinopathy, macular degeneration, inflammation, cancer, or metastatic tumor growth.

Further illustrating the invention is the method wherein the αv integrin receptor antagonizing effect is a dual αvβ3/αvβ5 antagonizing effect. More particularly, the dual αvβ3/αvβ5 antagonizing effect is selected from inhibition of: bone resorption, restenosis, angiogenesis, diabetic retinopathy, macular degeneration, inflammatory arthritis, cancer, or metastatic tumor growth.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating and/or preventing a condition mediated by antagonism of an αv integrin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammatory arthritis, cancer, tumor growth, and metastasis. More preferably, the condition is selected from osteoporosis and cancer. Most preferably, the condition is osteoporosis.

More specifically exemplifying the invention is a method of eliciting an αv integrin antagonizing effect in a mammal in need thereof, comprising administering to the mammal a therapeutically effective amount of any of the compounds or any of the pharmaceutical compositions described above. Preferably, the αv integrin antagonizing effect is an αvβ3 antagonizing effect; more specifically, the αvβ3 antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammatory arthritis, or inhibition of cancer or metastatic tumor growth. Most preferably, the αvβ3 antagonizing effect is inhibition of bone resorption. Alternatively, the αv integrin antagonizing effect is an αvβ5 antagonizing effect or a dual αvβ3/αvβ5 antagonizing effect. Examples of αvβ5 antagonizing effects are inhibition of restenosis, atherosclerosis, angiogenesis, diabetic retinopathy, macular degeneration, inflammatory arthritis, cancer, or metastatic tumor growth.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions described above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of bone resorption, metastatic tumor growth, cancer, restenosis, atherosclerosis, diabetic retinopathy, macular degeneration, inflammatory arthritis, and/or angiogenesis.

Also exemplifying the invention are compositions further comprising an active ingredient selected from the group consisting of a) an organic bisphosphonate or a pharmaceutically acceptable salt or ester thereof, b) an estrogen receptor modulator, c) an androgen receptor modulator, d) a cytotoxic/antiproliferative agent, e) a matrix metalloproteinase inhibitor, f) an inhibitor of epidermal-derived, fibroblast-derived, or platelet-derived growth factors, g) an inhibitor of VEGF, h) an antibody to a growth factor or to a growth factor receptor, i) an inhibitor of Flk-1/KDR, Flt-1, Tck/Tie-2, or Tie-1, j) a cathepsin K inhibitor, k) a growth hormone secretagogue, l) an inhibitor of osteoclast proton ATPase, m) an inhibitor of urokinase plasminogen activator (u-PA), n) a tumor-specific antibody-interleukin-2 fusion protein, o) an inhibitor of HMG-CoA reductase, and p) a prenylation inhibitor, such as a farnesyl transferase inhibitor or a geranylgeranyl transferase inhibitor or a dual farnesyl/geranylgeranyl transferase inhibitor;

and mixtures thereof.

(See, B. Millauer et al., "Dominant-Negative Inhibition of Flk-1 Suppresses the Growth of Many Tumor Types in Vivo", *Cancer Research,* 56, 1615–1620 (1996), which is incorporated by reference herein in its entirety).

Preferably, the active ingredient is selected from the group consisting of:

a) an organic bisphosphonate or a pharmaceutically acceptable salt or ester thereof, b) an estrogen receptor modulator, c) an androgen receptor modulator, d) an inhibitor of osteoclast proton ATPase, e) an inhibitor of IMG-CoA reductase, and f) a cathepsin K inhibitor; and mixtures thereof.

Nonlimiting examples of such bisphosphonates include alendronate, etidronate, pamidronate, risedronate, ibandronate, and pharmaceutically acceptable salts and esters thereof. A particularly preferred bisphosphonate is alendronate, especially alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

Members of the class of HMG-CoA reductase inhibitors, known as the "statins," have been found to trigger the growth of new bone, replacing bone mass lost as a result of osteoporosis (see *The Wall Street Journal,* Friday, Dec. 3, 1999, page B1). Therefore, the statins hold promise for the treatment of bone resorption. Nonlimiting examples of statins are lovastatin, simvastatin, atorvastatin, and pravastatin.

Evidence for crucial role of the urokinase-urokinase receptor (u-PA-u-PAR) in angiogenesis, tumor invasion, inflammation, and matrix remodeling during wound healing and development has been presented [see Y. Koshelnick et al., "Mechanisms of signaling through Urokinase Receptor and the Cellular Response," *Thrombosis and Haemostasis* 82: 305–311 (1999) and F. Blasi, "Proteolysis, Cell Adhesion, Chemotaxis, and Invasiveness Are Regulated by the u-PA-u-PAR-PAI-1 System," *Thrombosis and Haemostasis* 82: 298–304 (1999)]. Thus, specific antagonists of the binding of u-PA to u-PAR inhibit cell-surface plasminogen activation, tumor growth, and angiogenesis in both in vitro and in vivo models.

H. N. Lode and coworkers in *PNAS USA* 96: 1591–1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth.

The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases (see C. Farina et al., "Selective inhibitors of the osteoclast vacuolar proton ATPase as novel bone antiresorptive agents," *DDT,* 4:163–172 (1999)).

Evidence has been presented that androgenic steroids play a physiological role in the development of bone mass in men and women and that androgens act directly on bone. Androgen receptors have been demonstrated in human osteoblast-like cell lines and androgens have been shown to directly stimulate bone cell proliferation and differentiation. For a discussion, reference is made to S. R. Davis, "The therapeutic use of androgens in women," *J. Steroid Biochem. Mol. Biol.,* 69: 177–184 (1999) and K. A. Hansen and S. P. T. Tho, "Androgens and Bone Health," *Seminars in Reproductive Endocrinology,"* 16: 129–134 (1998). Thus, androgen receptor modulators may have utility in the treatment and prevention of bone loss in women.

Activators of the peroxisome proliferator-activated receptor-γ (PPARγ), such as the thiazolidinediones (TZD's), inhibit osteoclast-like cell formation and bone resorption in vitro. Results reported by R. Okazaki et al. in *Endocrinology,* 140, pp 5060–5065, (1999) point to a local mechanism on bone marrow cells as well as a systemic one on glucose metabolism. Nonlimiting examples of PPARγ activators include troglitazone, pioglitazone, rosiglitazone, and BRL 49653.

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate, an estrogen receptor modulator, an androgen receptor modulator, a cathepsin K inhibitor, an HMG-CoA reductase inhibitor, a PPARγ activator, or an inhibitor of the osteoclast proton ATPase.

Additional illustrations of the invention are methods of treating cancer or metastatic tumor growth in a mammal in need thereof, comprising administering to the mammal a therapeutically effective amount of a compound described above and one or more agents known to be cytotoxic/antiproliferative. Also, the compounds of the present invention can be administered in combination with radiation therapy for treating cancer and metastatic tumor growth.

In addition, the integrin αvβ3 antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid-induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an αvβ3 receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the Schemes and Examples below, various reagent symbols and abbreviations have the following meanings:

| | |
|---|---|
| AcOH: | Acetic acid. |
| Ar: | Argon |
| BH$_3$.DMS: | Borane.dimethylsulfide. |
| BOC(Boc): | t-Butyloxycarbonyl. |
| BOP: | Benzotriazol-1-yloxytris(dimethylamino)-phosphonium hexafluorophosphate. |
| CBZ(Cbz): | Carbobenzyloxy or benzyloxycarbonyl. |
| CDI: | Carbonyldiimidazole. |
| CH$_2$Cl$_2$: | Methylene chloride. |
| CH$_3$CN: | Acetonitrile |
| CHCl$_3$: | Chloroform. |
| DEAD: | Diethyl azodicarboxylate. |
| DIAD: | Diisopropyl azodicarboxylate. |
| DIBAH or DIBAL-H: | Diisobutylaluminum hydride. |
| DIPEA: | Diisopropylethylamine. |
| DMAP: | 4-Dimethylaminopyridine. |
| DME: | 1,2-Dimethoxyethane. |
| DMF: | N,N-Dimethylformamide. |
| DMSO: | Dimethylsulfoxide. |
| DPFN: | 3,5-Dimethyl-1-pyrazolylformamidine nitrate. |
| DPPF: | 1,1'-Bis(diphenylphosphino)-ferrocene. |
| EDC: | 1-(3-Dimethylaminopropyl)-3-ethylcarbodiimide.HCl |
| EtOAc: | Ethyl acetate. |
| (EtO)$_3$CMe: | Triethyl orthoacetate. |
| EtOH: | Ethanol. |
| HOAc: | Acetic acid. |
| HOAT: | 1-Hydroxy-7-azabenzotriazole |
| HOBT: | 1-Hydroxybenzotriazole. |
| HPLC: | High-performance liquid chromatography |
| IBCF: | Isobutylchloroformate |
| LDA: | Lithium diisopropylamide. |
| MeOH: | Methanol. |
| MNNG: | 1,1-methyl-3-nitro-1-nitrosoguanidine |
| NEt$_3$: | Triethylamine. |
| NMM: | N-methylmorpholine. |
| PCA.HCl: | Pyrazole carboxamidine hydrochloride. |
| PCTLC: | Preparative centrifugal thin-layer chromatography. |
| Pd(PPh$_3$)$_2$Cl$_2$: | Dichlorobis(triphenylphosphine)palladium (II) |
| Pd/C: | Palladium on activated carbon catalyst. |
| Ph: | Phenyl. |
| PMB: | para-Methoxybenzyl |
| PyCLU: | Chloro-N,N,N',N'-(tetramethylene)-formamidinium hexafluorophosphate. |
| pTSA | p-Toluenesulfonic acid. |
| TEA: | Triethylamine. |
| TFA: | Trifluoroacetic acid. |
| THF: | Tetrahydrofuran. |
| TLC: | Thin Layer Chromatography. |
| TMEDA: | N,N,N',N'-Tetramethylethylenediamine. |
| TMS: | Trimethylsilyl. |

The novel compounds of the present invention can be prepared according to the procedures of the following reaction Schemes and Examples, or modifications thereof, using readily available starting materials, reagents, and, where appropriate, conventional synthetic procedures. In these procedures, it is also possible to make use of variants which are themselves known to those of ordinary skill in the organic synthetic arts, but are not mentioned in greater detail.

The following Examples are illustrative of the more preferred compounds of the present invention. They are not, however, to be construed as forming the only genus that is considered as the invention. The Examples further illustrate details for preparation of the compounds of the present invention. Those skilled in the art will readily understand that known variations of the conditions and processes of the following preparative procedures can be used to prepare these compounds. Unless stated otherwise, all operations were carried out at room or ambient temperature, and all temperatures are degrees Celsius.

SCHEME 1

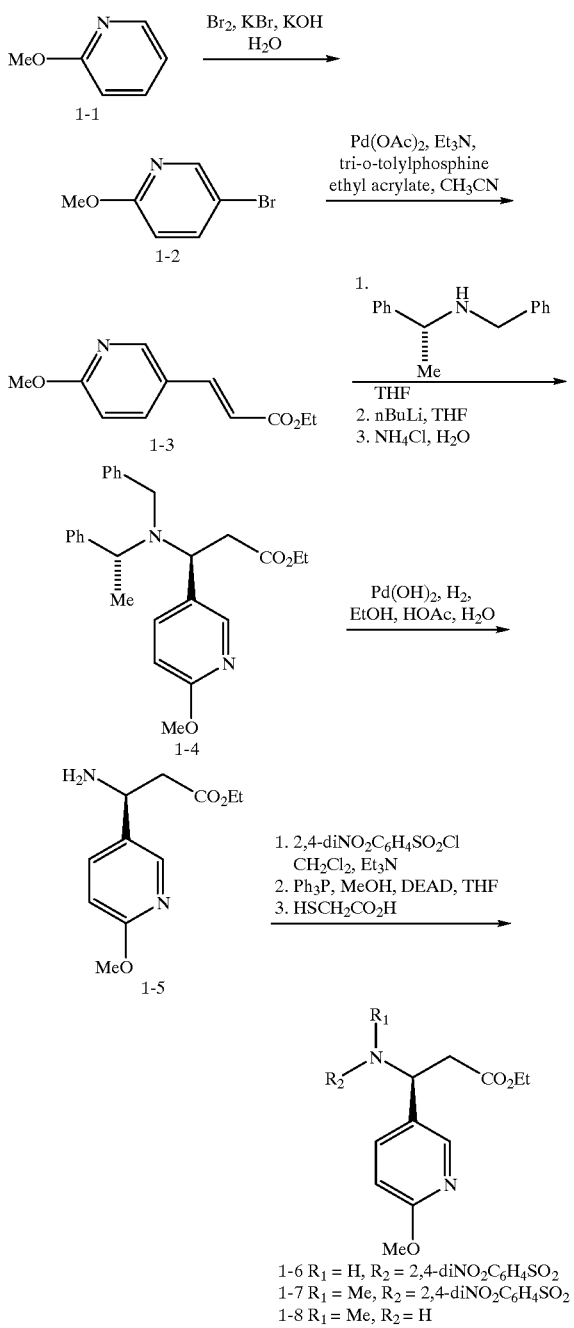

1-6 R₁ = H, R₂ = 2,4-diNO₂C₆H₄SO₂
1-7 R₁ = Me, R₂ = 2,4-diNO₂C₆H₄SO₂
1-8 R₁ = Me, R₂ = H

5-Bromo-2-methoxypyridine (1-2)

To a solution of KOH (4.2 g, 0.075 mol) in water (750 mL) was added 2-methoxypyridine (1-1) (16.4 g, 0.15 mol) followed by a dropwise addition of bromine (24 g, 0.15 mol) in 1N aqueous KBr (750 mL) and the resulting solution was stirred at room temperature for 5 hr. Solid NaHCO₃ was added until basic and the solution was extracted with CHCl₃ (3×500 mL). The organic layer was washed with 10% NaHSO₃, then brine, dried over Na₂SO₄, filtered, and the solvent removed in vacuo. The resulting dark brown oil was predominantly the desired compound 1-2 and was used as such in the next step.

$^1$H NMR (300 MHz, CDCl₃): δ3.91 (3H, s), 6.66 (1H, d), 7.62 (1H, dd), 8.20 (1H, dd).

Ethyl 3-(6-methoxypyridin-3-yl)acrylate (1-3)

A solution of the 5-bromo-2-methoxypyridine (1-2) (74.3 g, 0.4 mol), ethyl acrylate (150 mL, 1.4 mol), triethylamine (150 mL, 1.08 mol), palladium acetate (10 g, 0.045 mol) and tri-o-tolylphosphine (20 g, 0.066 mol) in 100 mL acetonitrile was degassed with argon for 10 minutes. The mixture was heated at 90° C. for 12 hr, then the volatiles were removed in vacuo. Toluene (300 mL) was added and the mixture concentrated again. Diethyl ether (300 mL) was added and the mixture filtered through a pad of silica gel eluting with 800 mL of diethyl ether. After removal of the diethyl ether, the residue was chromatographed on silica gel eluting with EtOAc/hexane, 1:19 then 1:14 then 1:9 to give 1-3 as a yellow solid.

$^1$H NMR (300 MHz, CDCl₃): δ1.34 (3H, t), 3.97 (3H, s), 4.26 (2H, q), 6.34 (1H, d), 6.76 (1H, d), 7.63 (1H, d), 7.77 (1H, dd), 8.27 (1H, d).

N-Benzyl-(R)-α-methylbenzyl-3(S)-(6-methoxypyridin-3-yl)-β-alanine ethyl ester (1-4)

To a solution of N-benzyl-(R)-α-methylbenzylamine (97.5 g, 462 mmol) in THF (750 mL) at 0° C. was added n-butyllithium (2.5M in hexanes; 178.5 mL, 446 mmol). The dark violet solution was stirred at 0° C. for 20 minutes, cooled to −78° C., and the ester 1-3 (63.7 g, 308 mmol) in THF (250 mL) was added over 60 minutes. The resulting solution was stirred at −78° C. for 1 hr, then cannulated into saturated NH₄Cl and extracted with EtOAc, washed with water, then brine, dried and concentrated in vacuo to give an oil. Column chromatography (silica gel; hexane/EtOAc 9:1 then 4:1) gave 1-4 as an oil contaminated with N-benzyl-(R)-α-methylbenzylamine. This oil was taken up in 5% AcOH in water and extracted with diethyl ether (4×). The organic layers were dried over MgSO₄ and the solvent removed to give the title compound 1-4.

$^1$H NMR (300 MHz, CDCl₃): δ1.08 (3H, t), 1.27 (3H, d), 2.52 (1H, dd), 2.62 (1H, dd), 3.66 (1H, d), 3.70 (1H, d), 3.93 (3H, s), 3.95 (2H, m), 4.41 (1H, dd), 6.74 (1H, d), 7.15–7.45 (10H, m), 7.64 (1H, dd), 8.15 (1H, d).

3(S)-(6-methoxypyridin-3-yl)-β-alanine ethyl ester (1-5)

To a degassed (argon) solution of the ester 1-4 (70 g) in EtOH (250 mL), HOAc (25 mL) and water (2 mL) was added 20% Pd(OH)₂ on carbon. The mixture was placed under hydrogen gas using a balloon and the resulting mixture was stirred for 24 hr. After filtration through celite (washing with EtOAc), the solvent was removed in vacuo to afford a waxy solid. This was dissolved in 200 mL water and extracted with diethyl ether (2×200 mL). The aqueous layer was then treated with solid K₂CO₃ until fully saturated and extracted with EtOAc (4×200 mL). After drying over MgSO₄, the solvent was removed in vacuo to give the title compound 1-5 as an oil which solidified in the freezer.

$^1$H NMR (300 MHz, CDCl₃): δ1.23 (3H, t), 2.61 (1H, dd), 2.68 (1H, dd), 3.92 (3H, s), 4.15 (2H, q), 4.41 (1H, dd), 6.93 (1H, d), 7.62 (1H, dd), 8.13 (1H, d).

3(S)-(6-Methoxy-pyridin-3-yl)-3-(4-nitro-benzenesulfonylamino)-propionic acid ethyl ester (1-6)

A solution of aminoester 1-5 (3.0 g, 13.0 mmol) in $CH_2Cl_2$ (20 mL) was treated with aq $NaHCO_3$ (4.4 g in 20 mL $H_2O$). 2,4-Dinitrobenzenesulfonyl chloride (4.3 g, 16 mmol) was added and the reaction mixture stirred for 12 h. The solution was extracted with $CH_2Cl_2$ (3×40 mL) and the combined organic solutions washed with satd aq $NaHCO_3$ (40 mL) and brine (40 mL). The solution was dried over $MgSO_4$, filtered, and concentrated. The residue was purified by flash chromatography (97:3 $CH_2Cl_2$/MeOH) to give the desired product 1-6.

TLC Rf=0.45 (5% methanol/dichloromethane).

3(S)-(6-Methoxy-pyridin-3-yl)-3-[methyl-(4-nitro-benzenesulfonyl)-amino]-propionicacid ethyl ester (1-7)

Triphenylphosphine (3.9 g, 15 mmol) was added to a solution of sulfonamide 1-6 (4.5 g, 10 mmol) in THF (30 mL). To this solution was added a solution of diethyl azodicarboxylate (2.4 mL, 15 mmol) in THF/MeOH (10 mL/2.02 mL). A vigorous exotherm occurred and the reaction was stirred overnight at room temperature. The dark mixture was concentrated. The dark oily residue was purified by flash chromatography (40% EtOAc/hexanes) to give the desired product 1-7.

TLC Rf=0.37 (40% ethyl acetate/hexanes).

3(S)-(6-Methoxy-pyridin-3-yl)-3-methylamino-propionic acid ethyl ester (1-8)

A solution of sulfonamide 1-7 (4.7 gm, 10 mmol) in $CH_2Cl_2$ (50 mL) was treated with triethylamine (2.8 mL, 20 mmol) and mercaptoacetic acid (1.04 mL, 15 mmol). The reaction was stirred for 90 min at room temperature. The green solution was diluted with EtOAc (500 mL) and washed with satd aqueous $NaHCO_3$ (150 mL), water (3×100 mL), and brine (3×100 mL). The solution was dried over $Na_2SO_4$, filtered and concentrated to a black oil. The residue was purified by flash chromatography (5% MeOH/$CH_2Cl_2$) to give the desired product 1-8.

$^1$HNMR (300 MHz, $CDCl_3$): δ8.07 (d, J=2.4 Hz, 1H), 7.57 (m, 1H), 6.73 (m, 1H), 4.11 (q, J=7.3 Hz, 2H), 3.93 (s, 3H), 2.72 (m, 2H), 1.21 (t, J=7.3 Hz, 3H) ppm.

Scheme 2

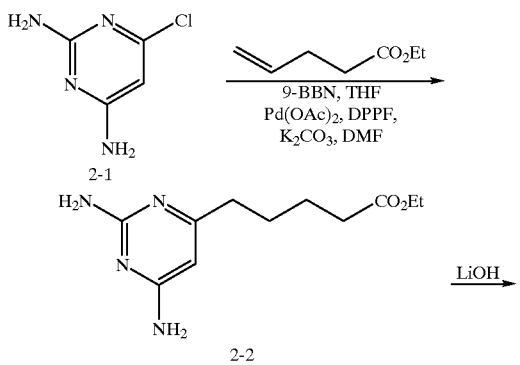

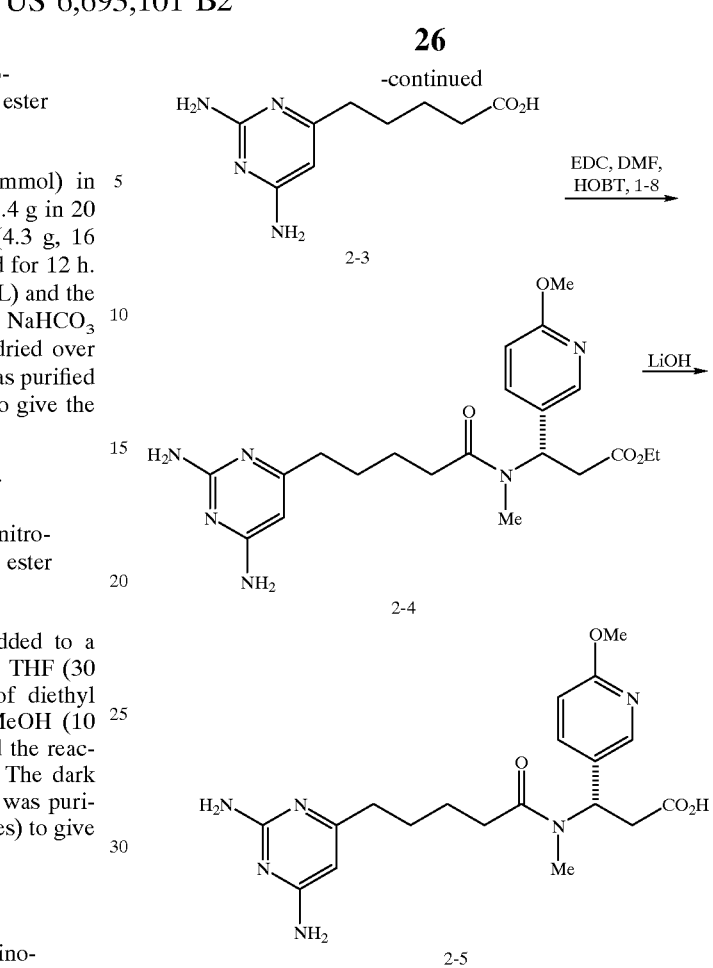

EXAMPLE 1

3(S)-{[5-(2,4-Diaminopyrimidin-6-yl)pentanoyl]-(N-methyl)amino}-3-(6-methoxypyridin-3-yl)-propanoic acid (2-5)

Step A: 5-(2,4-diaminopyrimid-6-yl)pentanoic acid ethyl ester (2-2)

Ethyl 4-pentenoate (4.93 gm, 38.4 mmol) was treated with 9-BBN (92.2 mL, 46.1 mmol; 0.5M in THE) at room temperature for 16 hours. To this solution was added Pd(OAc)$_2$ (863 mg, 3.84 mmol), 6-chloro-2,4-diaminopyrimidine (2-1, 5.0 g, 34.6 mmol), $K_2CO_3$ (7.95 g, 57.6 mmol), 1,1'-bis(diphenylphosphino)-ferrocene (2.13 g, 3.84 mmol) and DMF (100 mL). The mixture was degassed with argon for 10 minutes then heated to 90° C. for 24 hours. The reaction mixture was cooled and stirred with ethanolamine (10 mL) for 1 hour. The volatiles were removed in vacuo and the black tarry residue was partitioned between water and EtOAc. After extraction with EtOAc (4×), the organic layers were washed with water (4×), then brine, dried (MgSO$_4$) and concentrated. Purification by silica gel chromatography (5% MeOH in CHCl$_3$) afforded the title compound 2-2 as an oil.

$^1$H NMR (300 MHz, CDCl$_3$): δ5.72 (s, 1H), 4.97 (brs, 2H), 4.84 (brs, 2H), 4.12 (q, 2H), 2.43 (t, 2H), 2.32 (t, 2H), 1.67 (m, 4H), 1.25 (t, 3H) ppm.

Step B: 5-(2,4-diaminopyrimid-6-yl)pentanoic acid (2-3)

The ethyl ester 2-2 (190 mg, 0.8 mmol) in THF (10 mL) and water (10 mL) was treated with 1 N NaOH (1.6 mL, 1.6 mmol). After stirring at room temperature for 16 hours, the solution was neutralized with 1N HCl and then the solvents removed in vacuo. The residue, 2-3 was used as such in the next step.

Step C: 3(S)-{[5-(2,4-diaminopyrimidin-6-yl)pentanoyl]-(N-methyl)amino}-3-(6-methoxypyridin-3-yl)-propanoic acid (2-5)

The acid 2-3 (168 mg, 0.8 mmol), amine 1-8 (221 mg, 0.88 mmol), EDC (230 mg, 1.2 mmol) and HOAt (131 mg, 0.96 mmol) were dissolved in DMF (5 mL) and stirred at room temperature for 16 hours. The solution was partitioned between saturated NaHCO$_3$ solution and EtOAc, washed with brine, dried (MgSO$_4$) and concentrated in vacuo. The residue was purified by silica gel chromatography (20% MeOH in CHCl$_3$) to give the ester 2-4 as an oil which was used as such in the next step.

The ester 2-4 (180 mg, 0.42 mmol) in TBF (10 mL) and water (10 mL) was treated with 1 N NaOH (1.0 mL, 1.0 mmol). After stirring at room temperature for 16 hours, the solution was concentrated to 10 mL and purified by reverse phase HPLC (preppak C-18 column; water/acetonitrile/ 0.1% TFA gradient). After lyophilization, the title compound 2-5 (TFA salt) was obtained as a white powder. Mass spectrum: exact mass calculated for C$_{19}$H$_{27}$N$_6$O$_4$ (M+H) is 403.2088; found 403.2075.

Scheme 3

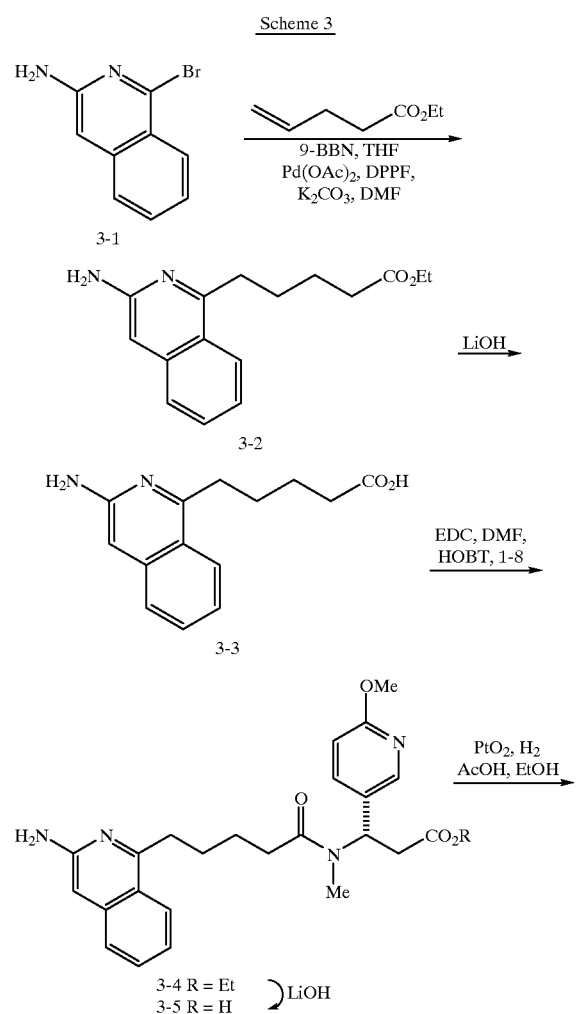

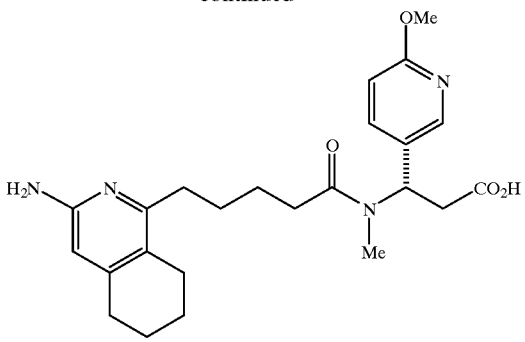

3-6

EXAMPLE 2

3(S)-{[5-(3-amino-5,6,7,8-tetrahydroisoquinolin-1-yl)pentanoyl]-(N-methyl)amino}-3-(6-methoxypyridin-3-yl)-propanoic acid (3-6)

Step A: 3(S)-{[5-(3-aminoisoquinolin-1-yl)pentanoyl]-(N-methyl)amino}-3-(6-methoxypyridin-3-yl)-propanoic acid (3-5)

Following the procedure described in Scheme 2 for the synthesis of 2-5, but using 3-amino-1-bromoisoquinoline as starting material, the title compound 3-5 was prepared.

Mass spectrum: exact mass calculated for C$_{24}$H$_{29}$7N$_4$O$_4$ (M+H) is 437.2183; found 437.2178.

Step B: 3(S)-{[5-(3-amino-5,6,7,8-tetrahydroisoquinolin-1-yl)pentanoyl]-(N-methyl)amino}-3-(6-methoxypyridin-3-yl)-propanoic acid (3-6)

A solution of the acid 3-5 (150 mg, 0.34 mmol) in EtOH (30 mL) and acetic acid (4 mL) was degassed with argon. PtO$_2$ (25 mg) was added and the mixture placed under an atmosphere of hydrogen gas (balloon) for 16 hours. The mixture was filtered through celite, the solvent removed and the residue purified by reverse phase HPLC (preppak C-18 column; water/acetonitrile/0.1% TFA gradient). After lyophilization, the title compound 3-6 was obtained as a light yellow powder. Mass spectrum: exact mass calculated for C$_{24}$H$_{33}$N$_4$O$_4$ (M+H) is 441.2496; found 441.2493.

Scheme 4

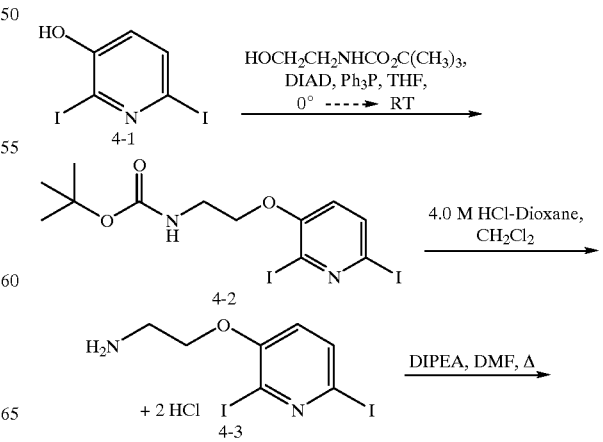

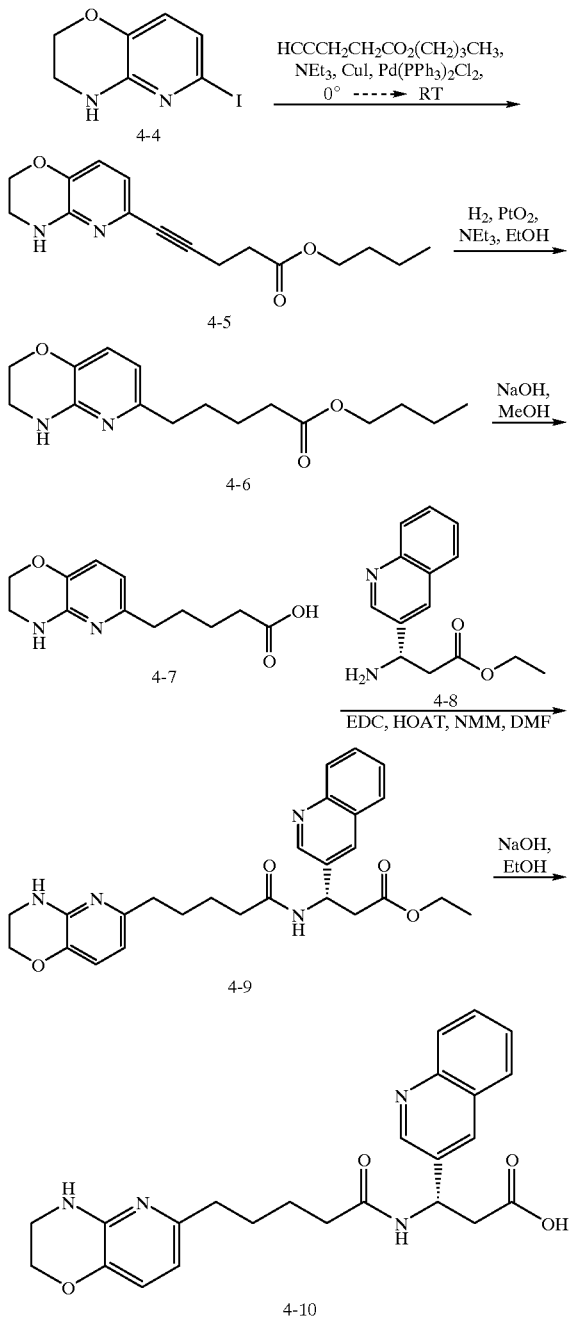

water, and brine, then dried with MgSO$_4$ and concentrated. Flash chromatography (silica, 30% EtOAc in hexanes) yielded a clear, colorless oil.

$^1$H-NMR (CDCl$_3$): δ7.54 (d, J=8.32 Hz, 1H), δ6.70 (d, J=8.32 Hz, 1H), δ5.03 (br s, 1H), δ4.06 (t, J=5.1 Hz, 2H), δ3.59 (dt, J=5.6, 5.5 Hz, 2H), δ1.45 (s, 9H). MS (M$^+$+H) 490.6.

Step B: 2-(2,6-Diiodo-pyridin-3-yloxy)-ethylamine (4-3)

To a solution of 4-2 (2.18 g, 4.45 mmol) in dichloromethane (5.0 mL) at room temperature under Ar was added 4.0 M HCl-dioxane solution (25 mL). A white precipitate formed immediately. After two hours the reaction was concentrated and dried to yield a white solid.

$^1$H-NMR (d$_6$-DMSO): δ8.24 (br s, 2H), δ7.76 (d, J=8.4 Hz, 1H), δ7.22 (d, J=8.4 Hz, 1H), δ4.30 (t, J=5.4 Hz, 2H), δ3.22 (dt, J=5.6, 5.5 Hz, 2H). MS (M$^+$+H) 390.8.

Step C: 6-Iodo-3,4-dihydro-2H-pyrido[3,2-b][1,4]oxazine (4-4)

A solution of 4-3 (1.32 g, 2.85 mmol) and DIPEA (1.29 g, 9.98 mmol) in DMEF (30 mL) under Ar was heated to 120° C. for ten hours. The mixture was concentrated and the residue partitioned between EtOAc and saturated NaHCO$_3$ solution. The organic phase was washed with sat. NaHCO$_3$ solution, water, and brine, then dried with MgSO$_4$ and concentrated. Flash chromatography (silica, 35% EtOAc-hexanes) yielded a clear, yellowish oil.

$^1$H-NMR (CDCl$_3$): δ6.91 (d, J=8.0 Hz, 1H), δ6.64 (d, J=8.0, 1H), δ5.16 (br s, 1H), δ4.19 (t, J=4.4, 2H), δ3.55 (m, 2H). MS (M$^+$+H) 262.8.

Step D: 5-(3,4-Dihydro-2H-pyrido[3,2-b][1,4]oxazin-6-yl)-pent-4-ynoic acid butyl ester (4-5)

A suspension of 4-4 (0.113 g, 0.431 mmol) and n-butyl 4-pentynoate (0.0731 g, 0.474 mmol) in triethylamine (3.0 mL) was purged with Ar, then cooled to 0° C. Copper iodide (0.0021 g, 0.0108 mmol) and Pd(PPh$_3$)$_2$Cl$_2$ (0.0076 g, 0.0108 mmol) were added, the ice bath was removed after ten minutes, and the resulting suspension was stirred overnight. The mixture was then partitioned between EtOAc and saturated NaHCO$_3$ solution. The organic phase was washed with sat. NaHCO$_3$ solution, water, and brine, then dried with MgSO$_4$ and concentrated. Flash chromatography (silica, 45% EtOAc-Hexanes) yielded a clear, yellowish oil.

$^1$H-NMR (CDCl$_3$): δ6.88 (d, J=7.9 Hz, 1H), δ6.69 (d, J=8.0 Hz, 1H), δ5.07 (br s, 1H), δ4.22 (t, J=4.4, 2H), δ4.10 (t, J=6.7 Hz, 2H), δ3.54 (m, 2H), δ2.70 (m, 2 H), δ2.61 (m, 2H), δ1.61 (m, 2H), δ1.38 (m, 2H), δ0.92 (t, J=7.4 Hz, 3H). MS (M$^+$+H) 289.1.

Step E: 5-(3,4-Dihydro-2H-pyrido[3,2-b][1,4]oxazin-6-yl)-pentanoic acid butyl ester (4-6)

A mixture of 4-5 (0.0643 g, 0.223 mmol), triethylamine (0.0169 g, 0.167 mmol), and PtO$_2$ (0.0064 g) in EtOH (3.0 mL) was stirred under a hydrogen balloon for four hours. The reaction was filtered through Celite and concentrated to yield a cloudy, colorless oil.

$^1$H-NMR (CDCl$_3$): δ6.88 (d, J=7.9 Hz, 1H), δ6.39 (d, J=7.8 Hz, 1H), δ4.69 (br s, 1H), δ4.20 (t, J=4.3 Hz, 2H), δ4.06 (t, J=6.7 Hz, 2H), δ3.54 (m, 2H), δ2.56 (br t, J=7.0 Hz, 2H), δ2.32 (m, 2H), δ1.56–1.69 (m, 6H), δ1.37 (m, 2H), δ0.93 (t, J=7.4 Hz, 3H). MS (M$^+$+H) 293.0.

Step F: 5-(3,4-Dihydro-2H-pyrido[3,2-b][1,4]oxazin-6-yl)-pentanoic acid (4-7)

A solution of 4-6 (0.223 mmol) and 1.0 N NaOH solution (0.268 mL, 0.268 mmol) in MeOH (1.5 mL) was stirred overnight. The reaction was neutralized by adding 1.0 N HCl solution (0.268 mL, 0.268 mmol) then concentrated and used in Step G without further purification.

EXAMPLE 3

3-(5–3,4-Dihydro-2H-pyrido[3,2-b][1,4]oxazin-6-yl-pentanoylamino)-3-(quinolin-3-yl)-propionic acid (4-10)

Step A: [2-(2,6-Diiodo-pyridin-3-yloxy)-ethyl]-carbamic acid tert-butyl ester (4-2)

To a solution of 2,5-diiodo-3-hydroxypyridine (4-1) (1.76 g, 5.07 mmol), N-BOC-ethanolamine (0.981 g, 6.08 mmol), and Ph$_3$P (1.86 g, 7.10 mmol) in dry TBF at 0° C. under Ar was added diisopropyl azodicarboxylate (1.54 g, 7.61 mmol) dropwise. The ice bath was removed after ten minutes and the reaction stirred overnight. The mixture was then partitioned between EtOAc and saturated NaHCO$_3$ solution. The organic phase was washed with sat. NaHCO$_3$ solution,

MS (M⁺+H) 237.1.

Step G: 3-(5–3,4-Dihydro-2H-pyrido [3,2-b][1,4]oxazin-6-yl-pentanoylamino)-3-(quinolin-3-yl)-propionic acid ethyl ester (4-9)

To a solution of 4-7 (0.223 mmol), 3(S)-(quinolin-3-yl)-3-aminopropionic acid dihydrochloride (4-8; preparation described in WO 99/31061, published Jun. 24, 1999) (0.0743 g, 0.234 mmol) in degassed DMF (2 mL) under Ar was added N-methylmorpholine (0.0902 g, 0.892 mmol), HOAT (0.0395 g, 0.290 mmol), and EDC (0.0556 g, 0.290 mmol). The reaction was stirred overnight then concentrated. The residue was partitioned between EtOAc and saturated NaHCO₃ solution. The organic phase was washed with sat. NaHCO₃ solution, water, and brine, then dried with MgSO₄ and concentrated. Flash chromatography (silica, 10% 20:1:1 EtOH/NH₄OH/H₂O-90% EtOAc) yielded a clear, colorless oil.

¹H-NMR (CDCl₃) δ8.91 (d, J=2.3 Hz, 1H), δ8.07 (m, 2H), δ7.76 (d, J=8.2 Hz, 1H), δ7.70 (dt, J=7.7, 1.5 Hz, 1H), δ7.54 (dt, J=7.5, 1.1 Hz, 1H), δ6.98 (d, J=8.4 Hz, 1H), δ6.86 (d, J=7.9 Hz, 1H), δ6.36 (d, J=7.9 Hz, 1H), δ5.66 (m, 1H), δ5.06 (br s, 1H), δ4.18 (t, J=4.4 Hz, 2H), δ4.07 (q, J=7.1 Hz, 2H), δ3.52 (m, 2 H), δ2.99 (m, 2H), δ2.56 (br t, 6.9 Hz, 2H), δ2.30 (br t, J=6.9 Hz, 2H), δ1.70 (m, 4H), δ1.15 (t, J=7.1 Hz, 3H). MS (M⁺+H) 463.4.

Step H: 3-(5-3,4-Dihydro-2H-pyrido[3,2-b][1,4]oxazin-6-yl-pentanoylamino)-3-quinolin-3-yl-propionic acid (4-10)

A solution of 4-8 (0.0657 g, 0.142 mmol) and 1.0 N NaOH solution (0.170 mL, 0.170 mmol) in EtOH (2.0 mL) was stirred overnight. The reaction was neutralized by adding 1.0 N HCl solution (0.170 mL, 0.170 mmol) then concentrated. Flash chromatography (silica, 75% 20:1:1 EtOH/NH₄OH/H₂O-25% EtOAc) yielded an off-white solid.

¹H-NMR (d₆-DMSO): δ8.88 (d, J=2.2 Hz, 1H), δ8.62 (d, J=7.8 Hz, 1H), δ8.18 (d, J=1.8 Hz, 1H), δ7.99 (d, J=8.4 Hz, 1H), δ7.90 (d, J=7.9 Hz, 1H), δ7.72 (t, J=7.7 Hz, 1H), δ7.59 (t, J=7.5 Hz, 1H), δ6.76 (d, J=7.8 Hz, 1H), δ6.59 (br s, 1H), δ6.22 (d, J=7.8 Hz, 1H), δ5.33 (m, 1H), δ4.05 (t, J=4.4 Hz, 2H), δ3.47–3.34 (m, 2H), δ2.78 (d, J=7.2 Hz, 2H), δ2.40 (br t, J=6.6 Hz, 2H), δ2.13 (br t, J=6.8 Hz, 2H), δ1.50 (m, 4H). MS (M⁺+H) 435.1.

Scheme 5

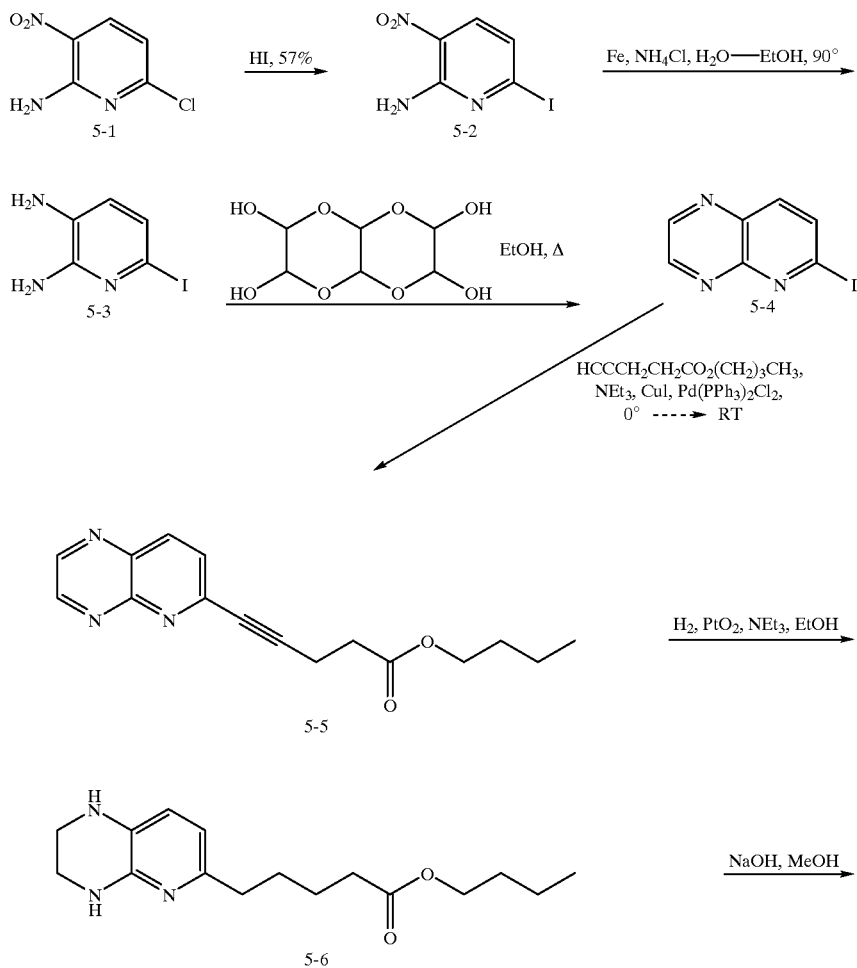

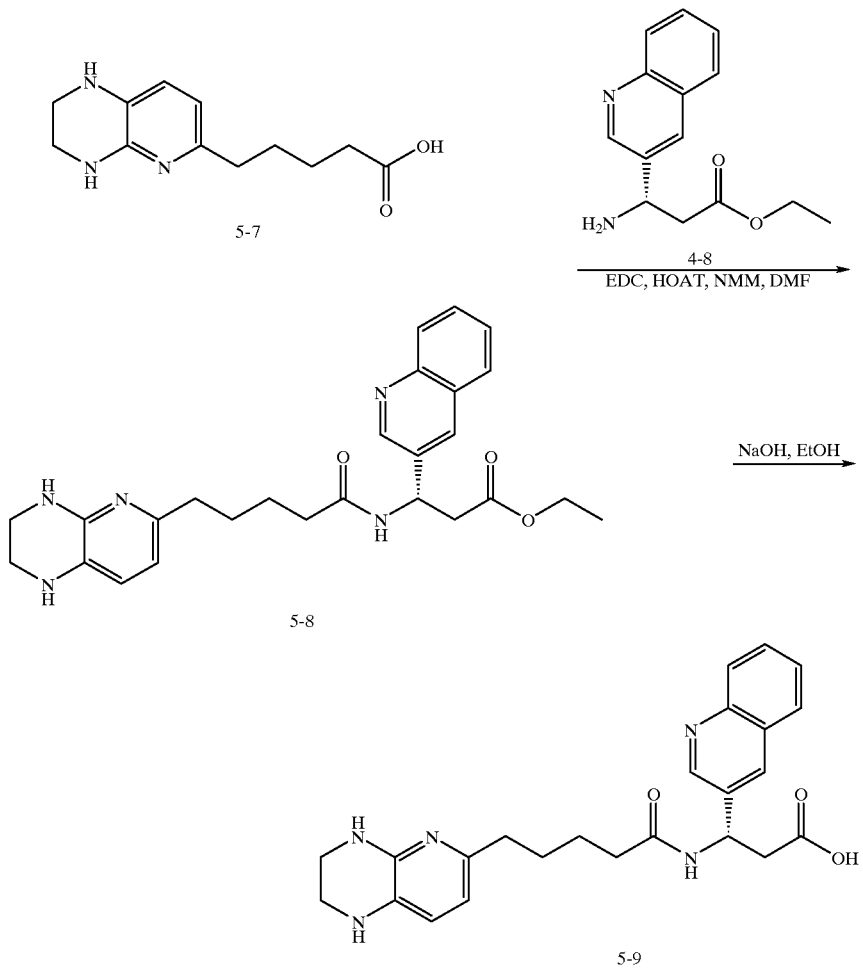

EXAMPLE 4

3-(Quinolin-3-yl)-3-(5–1,2,3,4-tetrahydro-pyrido[2,3-b]pyrazin-6-yl-pentanoylamino)-propionic acid (5-9)

Step A: 6-Iodo-3-nitro-pyridin-2-ylamine (5-2)

A mixture of 2-amino-6-chloro-3-nitropyridine (5-1) (5.00 g, 28.8 mmol) and 57% HI (100 mL) was stirred for 48 hours at RT. The red-orange colored suspension was filtered to collect the precipitate which was washed with a small amount of water. The resulting yellow solid was suspended in CH$_2$Cl$_2$ (100 mL) and water (50 mL), and triethylamine (5.0 mL) was added while stirring. The layers were separated and the aqueous phase was reextracted with 4:1 CHCl$_3$-isopropanol. The organic layers were combined and concentrated to yield a yellow solid.

$^1$H-NMR (d$_6$-DMSO): δ8.17 (br s, 2H), δ7.97 (d, J=8.5 Hz, 1H), δ7.13 (d, J=8.5 Hz, 1H). MS (M$^+$+H) 265.9.

Step B: 6-Iodo-pyridine-2,3-diamine (5-3)

To a solution of 5-2 (2.0 g, 7.55 mmol) and NH$_4$Cl (0.202 g, 3.78 mmol) in 2:1 EtOH-H$_2$O (37.8 mL) at 90° C. was added iron powder (2.11 g, 37.8 mmol) in three equal portions over ten minutes. The reaction turned very dark in color. After sixty minutes the hot mixture was filtered through Celite then concentrated. The residue was partitioned between EtOAc and saturated NaHCO$_3$ solution. The organic phase was washed with sat. NaHCO$_3$ solution and brine, then dried with MgSO$_4$ and concentrated to yield a brown solid.

$^1$H-NMR (CDCl$_3$): δ6.99 (d, J=7.7 Hz, 1H), δ6.59 (d, J=7.8 Hz, 1H), δ4.33 (br s, 2H), δ3.25 (br s, 2H). MS (M$^+$+H) 235.9.

Step C: 6-Iodo-pyrido[2,3-b]pyrazine(5-4)

A solution of 5-3 (1.66 g, 7.06 mmol) and glyoxal trimeric dihydrate (0.519 g, 2.47 mmol) in EtOH (35 mL) under Ar was heated to reflux for two hours on a timer, then sat for an additional 14 hours at room temperature without stirring. Resumption of stirring momentarily dissolved a dark brown solid in the solution, and a light brown precipitate formed almost immediately. The precipitate was filtered, washed with cold (0° C.) EtOH, then dried under vacuum. The liquid was concentrated to yield a brownish solid which was nearly as pure as the filtered precipitate.

$^1$H-NMR (CDCl$_3$): δ9.05 (d, J=1.7 Hz, 1H), δ8.97 (d, J=1.7 Hz, 1H), δ8.09 (d, J=8.5 Hz, 1H), δ8.06 (d, J=8.6 Hz, 1H). MS (M$^+$+H) 258.0.

Step D: 5-Pyrido[2,3-b]pyrazin-6-yl-pent-4-ynoic acid butyl ester (5-5)

A suspension of 5-4 (1.0 g, 3.89 mmol) and n-butyl 4-pentynoate (0.660 g, 4.28 mmol) in triethylamine (19.5 mL) was purged with Ar, then cooled to 0° C. Copper iodide (0.0185 g, 0.0973 mmol) and Pd(PPh$_3$)$_2$Cl$_2$ (0.0683 g, 0.0973 mmol) were added, the ice bath was removed after ten minutes, and the resulting suspension was stirred overnight. The mixture was then partitioned between EtOAc and saturated NaHCO$_3$ solution. The organic phase was washed with sat. NaHCO$_3$ solution, water, and brine, then dried with MgSO₄ and concentrated. Flash chromatography (silica, 65% EtOAc-Hexanes) yielded a dark reddish oil.

¹H-NMR (CDCl₃): δ9.07 (d, J=1.7 Hz, 1H), δ8.89 (d, J=1.7 Hz, 1H), δ8.39 (d, J=8.6 Hz, 1H), δ7.75 (d, J=8.6 Hz, 1H), δ4.14 (t, J=6.7 Hz, 2H), δ2.86 (t, J=7.8 Hz, 2H), δ2.71 (t, J=7.5 Hz, 2H), δ1.64 (m, 2H), δ1.40 (m, 2H), δ0.93 (t, J=7.4 Hz, 3H). MS (M⁺+H) 284.1.

Step E: 5-(1,2,3,4-Tetrahydro-pyrido[2,3-b]pyrazin-6-yl)-pentanoic acid butyl ester (5-6)

A mixture of 5-5 (0.83 g, 2.93 mmol), triethylamine (0.222 g, 2.20 mmol), and PtO₂·H₂O (0.083 g) in EtOH (15 mL) was stirred under a hydrogen balloon for four hours. The reaction was filtered through Celite and concentrated to yield a dark brown oil.

¹H-NMR (CDCl₃): δ6.58 (d, J=7.6 Hz, 1H), δ6.30 (d, J=7.6 Hz, 1H), δ4.67 (br s, 1H), δ4.05 (t, J=6.7 Hz, 2H), δ3.56 (br s, 1H), δ3.52 (m, 2H), δ3.36 (t, J=4.7 Hz, 2H), δ2.52 (m, 2H), δ2.32 (m, 2H), δ1.66 (m, 2H), δ1.59 (m, 2H), δ1.37 (m, 2H), 6.93 (t, 7.4 Hz, 3H). MS (M⁺+H) 292.2.

Step F: 5-(1,2,3,4-Tetrahydro-pyrido[2,3-b]pyrazin-6-yl)-pentanoic acid (5-7)

A solution of 5-6 (2.93 mmol) and 1.0 N NaOH solution (4.40 mL, 4.40 mmol) in MeOH (15 mL) was stirred overnight. The reaction was neutralized by adding 1.0 N HCl solution (4.40 mL, 4.40 mmol) then concentrated to yield a dark brown foam used as is in the next reaction.

¹H-NMR (d₆-DMSO): δ6.50 (d, J=7.6 Hz, 1H), δ6.26 (br s, 1H), δ6.17 (d, J=7.3 Hz, 1H), δ5.44 (br s, 1H), δ3.35 (m, 2H), δ3.17 (m, 2H), δ2.37 (t, J=6.9 Hz, 2H), δ2.20 (t, J=6.7 Hz, 2H), δ1.50 (m, 4H). MS (M⁺+H) 236.1.

Step G: 3-(Quinolin-3-yl)-3-(5-1,2,3,4-tetrahydro-pyrido[2,3-b]pyrazin-6-yl-pentanoylamino)-propionic acid ethyl ester (5-8)

To a solution of 5-7 (0.756 mmol), 3(S)-(quinolin-3-yl)-3-aminopropionic acid dihydrochloride (4-8) (0.200 g, 0.630 mmol) in degassed DMF (3 mL) under Ar was added N-methylmorpholine (0.255 g, 2.52 mmol), HOAT (0.111 g, 0.819 mmol), and EDC (0.157 g, 0.819 mmol). The reaction was stirred overnight then concentrated. The residue was partitioned between EtOAc and saturated NaHCO₃ solution. The organic phase was washed with sat. NaHCO₃ solution, water, and brine, then dried with MgSO₄ and concentrated. Flash chromatography (silica, 20% 20:1:1 EtOH/NH₄OH/H₂O-80% EtOAc) yielded a clear, yellowish oil.

¹H-NMR (CDCl₃): δ8.90 (t, J=2.3 Hz, 1H), δ8.07 (m, 2H), δ7.77 (d, J=8.0 Hz, 1H), δ7.69 (m, 1H), δ7.54 (t, J=7.5 Hz, 1H), δ7.00 (d, J=8.2 Hz, 1H), δ6.56 (d, J=7.6 Hz, 1H), δ6.27 (d, J=7.6 Hz, 1H), δ5.65 (m, 1H), δ4.95 (brs, 1H), δ4.07 (q, J=7.1 Hz, 2H), δ3.50 (m, 2H), δ3.34 (m, 2H), δ3.00 (m, 2H), δ2.52 (t, J=7.0 Hz, 2H), δ2.29 (t, J=7.0 Hz, 2H), δ1.68 (m, 4H), δ1.15 (t, J=7.1 Hz, 3H). MS (M⁺+H) 462.2.

Step H: 3-(Quinolin-3-yl)-3-(5–1,2,3,4-tetrahydro-pyrido[2,3-b]pyrazin-6-yl-pentanoylamino)-propionic acid (5-9)

A solution of 5-8 (0.141 g, 0.305 mmol) and 1.0 N NaOH solution (0.367 mL, 0.367 mmol) in EtOH (1.5 mL) was stirred overnight. The reaction was neutralized by adding 1.0 N HCl solution (0.0.367 mL, 0.367 mmol) then concentrated. Preparative HPLC followed by lyophilization yielded a yellow solid.

¹H-NMR (d6-DMSO): δ8.94 (d, J=2.4 Hz, 1H), δ8.58 (d, J=7.9 Hz, 1H), δ8.31 (d, J=1.5 Hz, 1H), δ8.00 (m, 2H), δ7.79 (m, 2H), δ7.65 (t, J=6.9 Hz, 1H), δ6.84 (d, J=7.6 Hz, 1H), δ6.41 (d, J=7.6 Hz, 1H), δ5.37 (m, 1H), δ3.47 (br t, J=4.9 Hz, 2H), δ3.21 (br t, J=4.7 Hz, 2H), δ2.88 (d, J=7.6 Hz, 2 H), 62.15 (m, 2H), δ1.47 (br s, 4H). MS (M⁺+H) 434.3.

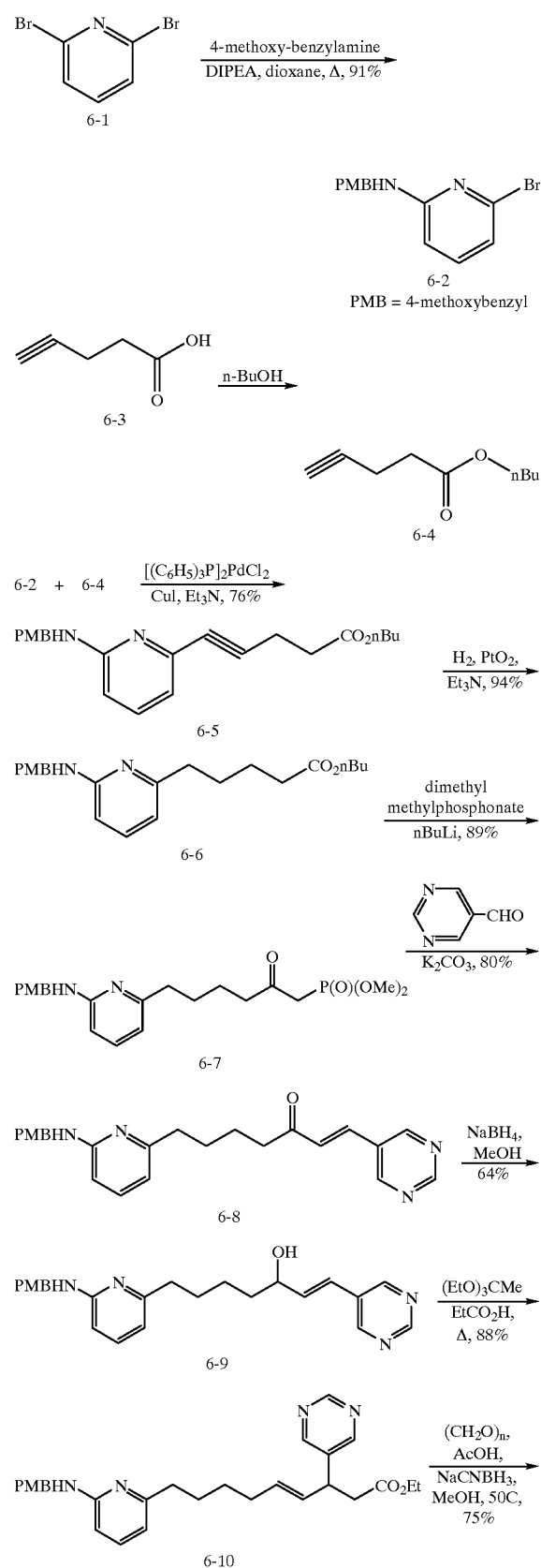

Scheme 6

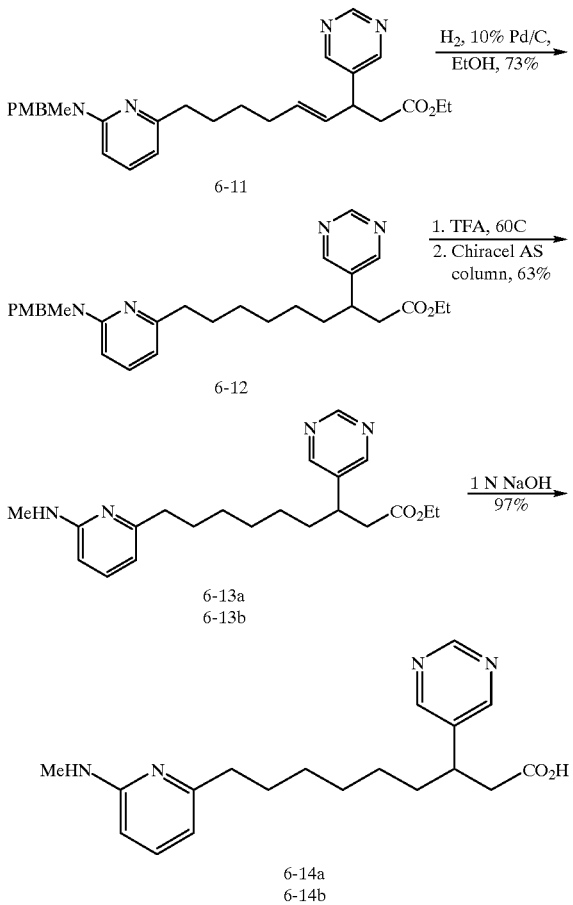

6-11

6-12

6-13a
6-13b 6-14a
6-14b

EXAMPLE 5

3(S or R)-9-(6-Methylamino-pyridin-2-yl)-3-(pyrimidin-5-yl)-nonanoic acid (6-4a)

Step A: (6-Bromo-pyridin-2-yl)-(4-methoxy-benzyl)-amine (6-2)

A solution of 2,6-dibromopyridine 6-1 (37.3 g, 157 mmol), 4-methoxybenzylamine (21.6 g, 157 mmol), and diisopropylethylamine (22.4 g, 173 mmol) in 1,4-dioxane (150 mL) was heated at reflux for 24 h. The reaction mixture was cooled, concentrated in vacuo, and the residue was partitioned between EtOAc (100 mL) and saturated aqueous $NaHCO_3$ (125 mL). The organic layer was washed with water (100 mL) followed by brine (100 mL) and dried ($Na_2SO_4$). The organic layer was filtered, concentrated in vacuo, and purified by flash chromatography (silica, 10% to 40% EtOAc/hexanes) affording 42 g of amine 6-2 as a white solid in 91% yield.

$^1$H NMR (300 MHz, $CDCl_3$) δ7.26–7.22 (m, 3H), 6.88–6.86 (m, 2H), 6.75–6.73 (d, 1H), 6.27–6.25 (d, 1H), 4.98–4.96 (br s, 1H), 4.39–4.37 (d, 2H), 3.80 (s, 3H).

Step B: Pent-4-ynoic acid butyl ester (6-4)

HCl was bubbled into a n-butanol solution (200 mL) of pent-4-ynoic acid 6-3 (10 g, 102 mmol) for ten minutes. The solution was stirred overnight at room temperature. The solvent was removed in vacuo providing the crude ester 6-4 as a yellow liquid in quantitative yield.

$^1$H NMR (400 MHz, $CDCl_3$) δ4.12–4.09 (t, 2H), 2.55–2.50 (m, 4H), 1.98–1.96 (t, 1H), 1.63–1.60 (m, 2H), 1.41–1.35 (m, 2H), 0.95–0.91 (t, 3H).

Step C: 5-[6-(4-Methoxy-benzylamino)-pyridin-2-yl]-pent-4-ynoic acid butyl ester (6-5)

To a mixture of 6-2 (8.64 g, 29.48 mmol) and 6-4 (5.0 g, 32.4 mmol) in $Et_3N$ (50 mL) at 0° was added CuI (0.14 g, 0.74). The solution was purged with argon and [$(C_6H_5)_3$P]$_2PdCl_2$ (0.52 g, 0.74 mmol) was added. After 1 h the cooling bath was removed and the solution was stirred for an additional 12 h. The solution was diluted with diethyl ether (250 mL) and washed with water (4×100 ml) followed by brine (100 mL). The etheral layer was dried ($Na_2SO_4$), concentrated, and chromatographed (silica gel, 30% ethyl acetate/hexanes) to give 8.6 g of 6-5.

$^1$H NMR (400 MHz, $CDCl_3$) δ7.34–7.30 (t, 1H), 7.26–7.24 (m, 2H), 6.87–6.85 (m, 2H), 6.72–6.70 (d, 1H), 6.29–6.27 (d, 1H), 4.91–4.88 (t, 1H), 4.40–4.38 (d, 2H), 4.13–4.11 (t, 2H), 3.79 (s, 3H), 2.74–2.72 (m, 2H), 2.66–2.64 (m, 2H), 1.66–1.55 (m, 2H), 1.42–1.34 (m, 2H), 0.94–0.90 (t, 3H).

Step D: 5-[6-(4-Methoxy-benzylamino)-pyridin-2-yl]-pentanoic acid butyl ester (6-6)

A mixture of 6-5 (6.54 g, 17.8 mmol), $Et_3N$ (1.85 mL, 13.3 mmol), and $PtO_2$ (0.405 g, 1.78) in EtOH (150 mL) was stirred under a balloon of hydrogen for 6 h. Filtration through celite and evaporative removal of the solvent afforded 6.23 g of 6-6 as a colorless oil. The crude product was used directly in the next step without purification.

$^1$H NMR (400 MHz, $CDCl_3$) δ7.34–7.27 (m, 3H), 6.87–6.85 (m, 2H), 6.45–6.43 (d, 1H), 6.19–6.17 (d, 1H), 4.79–4.76 (t, 1H), 4.38–4.37 (d, 2H), 4.07–4.05 (t, 2H), 3.79 (s, 3H), 2.64–2.59 (m, 2H), 2.35–2.31 (m, 2H), 1.76–1.68 (m, 4H), 1.62–1.55 (m, 2H), 1.42–1.33 (m, 2H), 0.94–0.92 (t, 3H).

Step E: {6-[6-(4-Methoxy-benzylamino)-pyridin-2-yl]-2-oxo-hexyl}-phosphonic acid dimethyl ester (6-7)

A solution of dimethyl methylphosphonate (2.48 g, 20 mmol) in anhydrous THF (30 mL) was cooled to –78° and treated dropwise with 2.5 M n-BuLi (8.0 mL). After stirring at –78° for 45 min, a solution of ester 6-6 (1.85 g, 5.0 mmol) in THF (10 mL) was added dropwise and the resulting solution stirred for 30 min at –78°, quenched with sat. $NH_4Cl$ (25 mL), then extracted with ethyl acetate (3×75 mL). The combined organic extracts were dried ($Na_2SO_4$), filtered, and concentrated to afford a yellow oil. Chromatography on silica gel (5% MeOH/$CH_2Cl_2$) afforded 6-7 as a yellow oil in 89% yield.

$^1$H NMR (400 MHz, $CDCl_3$) δ7.33–7.26 (m, 3H), 6.87–6.85 (m, 2H), 6.44–6.43 (d, 1H), 6.19–6.17 (d, 1H), 4.83–4.79 (t, 1H), 4.38–4.37 (d, 2H), 3.79 (s, 3H), 3.78 (s, 3H), 3.76 (s, 3H), 3.13–3.04 (m, 2H), 2.66–2.58 (m, 4H), 1.70–1.64 (m, 4H).

Step F: 7-[6-(4-Methoxy-benzylamino)-pyridin-2-yl]-1-pyrimidin-4-yl-hept-1-en-3-one (6-8)

To a solution of 6-7 (1.87 g, 4.44 mmol), pyrimidine-5-carbaldehyde (0.480 g, 4.44 mmol) in 15 mL DMF was added $K_2CO_3$ (0.922 g, 6.67 mmol). The mixture was stirred at ambient temperature for 15 hr, and concentrated to a paste. The residue was diluted with water, extracted with ethyl acetate, and dried over sodium sulfate. Following concentration, the residue was chromatographed on silica gel (5% MeOH/$CH_2Cl_2$) to give 1.44 g of 6-8 as a white solid.

$^1$H NMR (300 MHz, $CDCl_3$) δ9.19 (s, 1H), 8.88 (s, 2H), 7.47–7.29 (m, 4H), 6.87–6.82 (m, 3H), 6.47–6.45 (d, 1H), 6.21–6.18 (d, 1H), 4.82–4.78 (t, 1H), 4.39–4.37 (d, 2H), 3.79 (s, 3H), 2.73–2.62 (m, 4H), 1.77–1.74 (m, 4H).

Step G: 7-[6-(4-Methoxy-benzylamino)-pyridin-2-yl]-1-pyrimidin-4-yl-hept-1-en-3-ol (6-9)

A solution of the enone 6-8 (3.0 g, 7.45 mmol) in MeOH (30 mL) at 0° was treated with NaBH$_4$. The ice bath was removed and the solution was stirred at room temperature for 1 hr. The reaction was quenched with water (25 mL) and extracted with EtOAc (3×125 mL). The organics were combined, dried (Na$_2$SO$_4$), concentrated in vacuo, and purified on silica gel (5% MeOH/CH$_2$Cl$_2$) to afford 1.94 g of 6-9.

$^1$H NMR (300 MHz, CDCl$_3$) δ9.06 (s, 1H), 8.72 (s, 2H), 7.37–7.18 (m, 3H), 6.87–6.84 (m, 2H), 6.57–6.36 (m, 3H), 6.21–6.19 (d, 1H), 5.52–5.46 (br s, 1H), 4.41–4.36 (m, 3H), 3.79 (s, 3H), 2.67–2.62 (t, 2H), 2.08 (s, 1H), 1.80–1.64 (m, 4H), 1.56–1.47 (m, 2H).

Step H: (±) 9-[6-(4-Methoxy-benzylamino)-pyridin-2-yl]-3-pyrimidin-5-yl-non-4-enoic acid ethyl ester (6-10)

A solution of the allylic alcohol 6-9 (1.6 g, 3.37 mmol) in (EtO)$_3$CMe (10 mL) was treated with 100 uL of a 1 mL solution of (EtO)$_3$CMe containing 10 uL of propionic acid. The yellow solution was heated at 150° for 90 minutes. The solution was cooled to room temperature and poured into 1N HCl/brine. The mixture was extracted with CHCl$_3$, dried, concentrated, and purified on silica gel (5%MeOH/CHCl$_3$) to give 2.01 g of 6-10.

$^1$H NMR (300 MHz, CDCl$_3$) δ9.02 (s, 1H), 8.62 (s, 2H), 7.37–7.28 (m, 3H), 6.87–6.85 (d, 2H), 6.43–6.40 (d, 1H), 6.20–6.17 (d, 1H), 5.56–5.53 (m, 2H), 4.38–4.36 (d, 2H), 4.10–4.02 (q, 2H), 3.87–3.84 (m, 1H), 3.79 (s, 3H), 2.82–2.56 (m, 5H), 2.12–2.03 (m, 3H), 1.47–1.36 (m, 2H), 1.19–1.14 (t, 3H).

Step I: (±)-9-{6-[(4-Methoxy-benzyl)-methyl-amino]-pyridin-2-yl}-3-pyrimidin-5-yl-non-4-enoic acid ethyl ester (6-11)

To a solution of 6-10 (1.6 g, 3.37 mmol) in methanol (30 mL) was added paraformaldehyde (0.80 g) and acetic acid (0.96 mL, 16.8 mmol). After stirring at 50° C. for 15 minutes, NaCNBH$_3$ (0.275 g, 4.38 mmol) was added and the mixture stirred for an additional 30 minutes at 50° C. Evaporation of the solvents and purification on silica gel (5% MeOH/CHCl$_3$) afforded 6-10 in 75% yield.

$^1$H NMR (300 MHz, CDCl$_3$) δ9.08 (s, 1H), 8.59 (s, 2H), 7.36–7.16 (m, 3H), 6.84–6.81 (d, 2H), 6.39–6.36 (d, 1H), 6.31–6.28 (d, 1H), 5.55–5.52 (m, 2H), 4.75 (s, 2H), 4.10–4.02 (q, 2H), 3.85–3.81 (m, 1H), 3.78 (s, 3H), 2.82–2.58 (m, 5H), 1.75–1.64 (m, 3H), 1.45–1.36 (m, 2H), 1.19–1.14 (t, 3H).

Step J: (±)-9-{6-[(4-Methoxy-benzyl)-methyl-amino]-pyridin-2-yl}-3-pyrimidin-5-yl-nonanoic acid ethyl ester (6-12)

A mixture of 6-11 (1.23 g, 2.51 mmol) and 10% Pd/C (0.200 g) in EtOH (25 mL) was stirred under a balloon of hydrogen for 2 days. Filtration through celite and evaporative removal of the solvent followed by purification on silica gel (70:25:5 CHCl$_3$:EtOAc:MeOH) afforded 0.900 g of 6-12.

$^1$H NMR (400 MHz, CDCl$_3$) δ9.08 (s, 1H), 8.57 (s, 2H), 7.36–7.30 (m, 1H), 7.18–7.16 (d, 2H), 6.83–6.81 (d, 2H), 6.39–6.36 (d, 1H), 6.31–6.28 (d, 1H), 4.75 (s, 2H), 4.06–4.01 (q, 2H), 3.78 (s, 3H), 3.10–3.04 (m, 1H), 2.98 (s, 3H), 2.73–2.53 (m, 5H), 1.72–1.62 (m, 3H), 1.54–1.24 (m, 6H), 1.16–1.12 (t, 3H).

Step K: 3(S or R)-9-(6-Methylamino-pyridin-2-yl)-3-(pyrimidin-5-yl)-nonanoic acid ethyl ester (6-13a)

A solution of 12 (0.900 g, 1.83 mmol) in trifluoroacetic acid (5 mL) was stirred at 60° C. for 15 minutes. The solvent was evaporated and the residue was azeotroped (2×25 ml toluene). Purification on silica gel (90:10:1 CHCl$_3$:MeOH:NH$_4$OH) gave 6-13, which was resolved on a chiral AS column, 60 ml/min, 4:1 Hexane:isopropanol (0.1% diethylamine) to give enantiomers 6-13a (faster-eluting) and 6-13b (slower eluting).

$^1$H NMR (400 MHz, CDCl$_3$) δ9.09 (s, 1H), 8.59 (s, 2H), 7.41–7.35 (m, 1H), 6.43–6.40 (d, 1H), 6.22–6.19 (d, 1H), 4.73–4.66 (br s, 2H), 4.08–4.00 (q, 2H), 3.15–3.04 (m, 1H), 2.89–2.87 (d, 3H), 2.76–2.67 (m, 1H), 2.61–2.53 (m, 3H), 1.74–1.57 (m, 4H), 1.33–1.24 (m, 6H), 1.54–1.24 (m, 6H), 1.17–1.12 (t, 3H).

Step L: 3(S or R)-9-(6-Methylamino-pyridin-2-yl)-3-(pyrimidin-5-yl)-nonanoic acid (6-14a)

To a solution of 6-13a (0.215 g, 0.580 mmol) in TBf/MeOH/H$_2$O 3:1:1 (10 mL)) was added NaOH (1.16 mL of 1N solution in water, 1.16 mmol). After 30 minutes, the mixture was neutralized with HCl (1.16 mL of 1N solution in water, 1.16 mmol) and the solvents were evaporated. The residue chromatographed on silica gel (15% MeOH/CHCl$_3$) to give 6-14a as a white solid.

$^1$H NMR (300 MHz, CDCl$_3$) δ9.06 (s, 1H), 8.63 (s, 2H), 7.62–7.55 (t, 1H), 6.40–6.37 (d, 2H), 3.30–3.21 (m, 1H), 2.87 (s, 3H), 2.80–2.56 (m, 4H), 1.93–1.85 (m, 1H), 1.70–1.59 (m, 4H), 1.55–1.49 (m, 1H), 1.36–1.22 (m, 5H).

EXAMPLE 6

3(R or S)-9-(6-Methylamino-pyridin-2-yl)-3-(pyrimidin-5-yl)-nonanoic acid (6-14b)

Enantiomer 6-14b was obtained from 6-13b utilizing the same method described for the preparation of 6-14a. Its 300 MHz NMR spectrum in CDCl$_3$ was identical to that of its enantiomer 6-14a.

Scheme 7

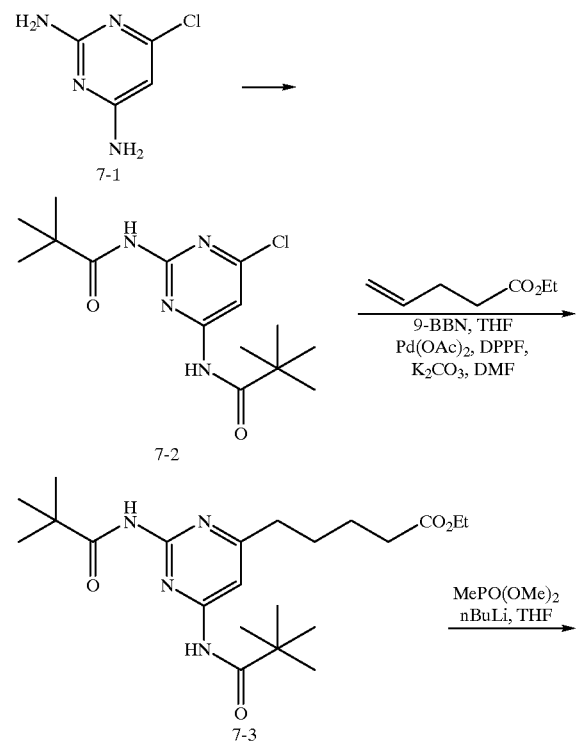

-continued

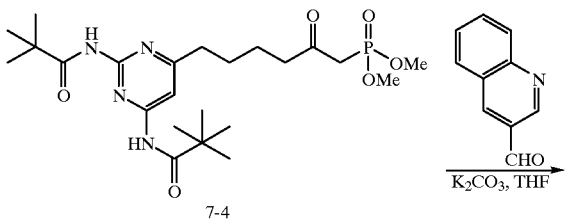

7-4

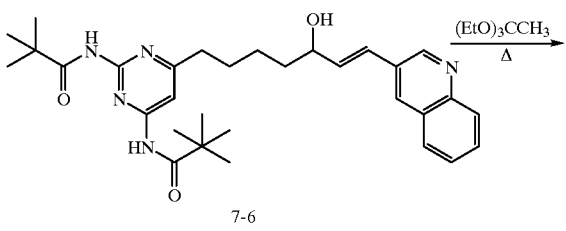

7-5

7-6

7-7

7-8

-continued

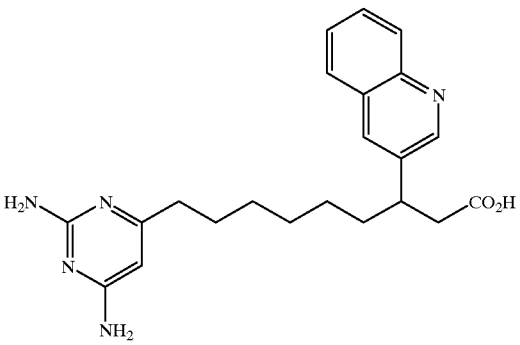

7-9

EXAMPLE 7

9-(2,4-Diaminopyrimidin-6-yl)-3-(quinolin-3-yl)-nonanoic acid (7-9)

Step A: 4-Chloro-2,6-dipivaloylaminopyrimidine (7-2)

A solution of 4-chloro-2,6-diaminopyrimidine 7-1 (5.0 g, 34.6 mmol), trimethylacetyl chloride (12.8 mL, 104 mmol) and triethylamine (19.2 mL, 138 mmol) in THF (100 mL) was stirred at room temperature for 48 hours. The mixture was poured into water, extracted with EtOAc (2×), washed with water, then brine, dried (MgSO$_4$) and concentrated to give an oil. Purification by silica gel chromatography (hexane:EtOAc 2:1) afforded the title compound 7-2 as a white solid.

$^1$H NMR (300 MHz, CDCl$_3$) δ8.75 (bs, 1H), 8.03 (s, 2H), 1.31 (s, 9H), 1.30 (s, 9H) ppm Step B: 5-(2,4-Dipivaloylaminopyrimidin-6-yl)pentanoic acid ethyl ester (7-3)

Ethyl 4-pentenoate (1.0 g, 7.8 mmol) was treated with 9-BBN (18.72 mL, 9.36 mmol; 0.5M in THF) at room temperature for 16 hours. To this solution was added Pd(OAc)$_2$ (175 mg, 0.78 mmol), pyrimidine 7-2 (2.44 mg, 7.8 mmol), K$_2$CO$_3$ (2.15 g, 15.6 mmol), 1,1'-bis(diphenylphosphino)-ferrocene (DPPF) (433 mg, 0.78 mmol) and DMF (25 mL). The mixture was degassed with argon for 10 minutes then heated to 80° C. for 24 hours. The reaction mixture was cooled and stirred with ethanolamine (10 mL) for 3 hours. The mixture was partitioned between saturated NaHCO$_3$ and EtOAc, washed with brine, dried (MgSO$_4$) and concentrated. Purification by silica gel chromatography (hexane:EtOAc 2:1) afforded the title compound 7-3 as a solid.

$^1$H NMR (300 MHz, CDCl$_3$) δ9.12 (s, 1H), 8.04 (s, 1H), 7.84 (s, 1H), 4.12 (q, 2H), 2.65 (t, 2H), 2.33 (t, 2H), 1.7 (m, 4H), 1.33 (s, 9H), 1.31 (s, 9H), 1.26 (t, 3H) ppm.

Step C: 7-(2,4-Dipivaloylaminopyrimidin-6-yl)-1-(quinolin-3-yl)-3-oxo-hept-1-ene (7-5)

Dimethyl methylphosphonate (4.28 g, 34.5 mmol) in THF (25 mL) at −78° C. was treated with n-butyllithium (2.5 M in hexanes; 13.8 mL, 34.5 mmol) dropwise over 15 minutes. To this was added the ester 7-3 (2 g, 4.93 mmol) in THF (5 mL) and the solution stirred a further 30 minutes at −78° C. before being quenched with saturated NH₄Cl. The mixture was partitioned between water and EtOAc. After extraction with EtOAc (4×), the organic layers were washed with water then brine, dried (MgSO₄) and filtered through celite. Concentration in vacuo afforded the phosphonate 7-4 as an oil which was used as such in the next step.

The phosphonate 7-4 (1 g, 2.46 mmol), 3-quinolinecarbaldehyde (387 mg, 2.46 mmol) and K₂CO₃ (3.74 mg, 2.71 mmol) in THF (15 mL) was stirred at 50° C. for 16 hours. The mixture was partitioned between saturated NaHCO₃ and EtOAc. After extraction with EtOAc, the organic layers were dried (MgSO₄), filtered through celite and concentrated. Purification by silica gel chromatography (EtOAc) yielded the title compound 7-5.

Mass spectrum: calculated for $C_{30}H_{38}N_5O_3$ (M+H) is 516.7; found 516.1.

Step D: 9-(2,4-Dipivaloylaminopyrimidin-6-yl)-3-(quinolin-3-yl)-4-noneneoic acid ethyl ester (7-7)

The enone 7-5 (1 g, 1.94 mmol) in MeOH (50 mL) at −30° C. was treated with NaBH₄ (80 mg, 2.14 mmol) and stirred for 1 hour. The mixture was quenched with water then partitioned between saturated NaHCO₃ and EtOAc. After extraction with EtOAc, the organic layers were washed with brine, dried (MgSO₄) and filtered through celite. Concentration in vacuo afforded the alcohol 7-6 as an oil which was used as such in the next step.

The alcohol 7-6 (900 mg, 1.74 mmol), propionic acid (6.5 mg, 0.09 mmol) and triethyl orthoacetate (10 mL) were heated at 150° C. for 2.5 hours. The mixture was cooled, concentrated and purified by silica gel chromatography (hexane: EtOAc 1:1) to afford the title compound 7-7.

Mass spectrum: calculated for $C_{34}H_{46}N_5O_4$ (M+H) is 588.8; found 588.2.

Step E: 9-(2,4-Dipivaloylaminopyrimidin-6-yl)-3-(quinolin-3-yl)-nonanoic acid ethyl ester (7-8)

The alkene 7-7 (1.02 g, 1.74 mmol) was dissolved in EtOH (50 mL) and degassed with argon. Palladium on carbon (10%; 100 mg) was added and the mixture stirred under an atmosphere of hydrogen gas (balloon) for 3 hours. The mixture was filtered through celite and the solvent removed to give the title compound 7-8 which was used as such in the next step.

Mass spectrum: calculated for $C_{34}H_{48}N_5O_4$ (M+H) is 590.8; found 590.2.

Step F: 9-(2,4-Diaminopyrimidin-6-yl)-3-(quinolin-3-yl)-nonanoic acid (7-9)

The ester 7-8 (1 g, 1.7 mmol) was dissolved in TBF (20 mL) and water (20 mL) and treated with 1N LiOH (7 mL) at room temperature for 16 hours. After neutralization with 3N HCl, the solution was concentrated in vacuo, filtered through a bed of silica gel (EtOH:H₂O:NH₄OH 10:1:1) and the residue purified by reverse phase HPLC (preppak C-18 column; water/acetonitrile/0.1% TFA gradient). After lyophilization, the title compound 7-9 (TFA salt) was obtained as a white powder.

¹H NMR (300 MHz, CD₃OD) δ9.11 (d, 1H), 8.88 (s, 1H), 8.18 (m, 2H), 8.03 (t, 1H), 7.88 (t, 1H), 5.88 (s, 1H), 3.45 (m, 1H), 2.9 (d, 1H), 2.7 (d, 1H), 2.46 (t, 2H), 1.9 (m, 2H), 1.6 (m, 2H) 1.1–1.5 (m, 6H) ppm.

Mass spectrum: calculated for $C_{22}H_{28}N_5O_2$ (M+H) is 394.5; found 394.0.

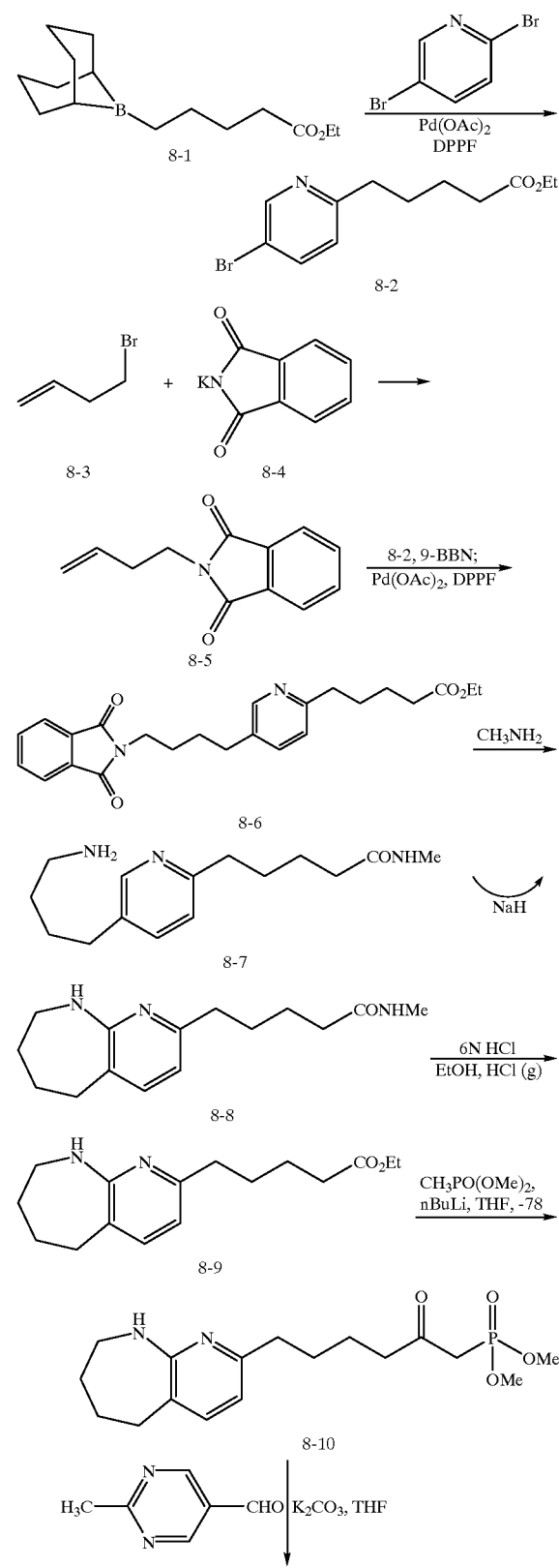

Scheme 8

45

-continued

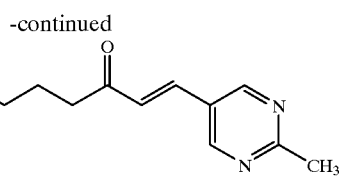
8-11

NaBH₄;
Chiralpak AD chromatography

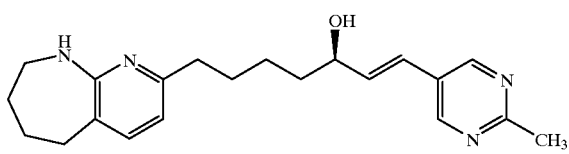
8-12

CH₃C(OEt)₃,
cat. propionic acid

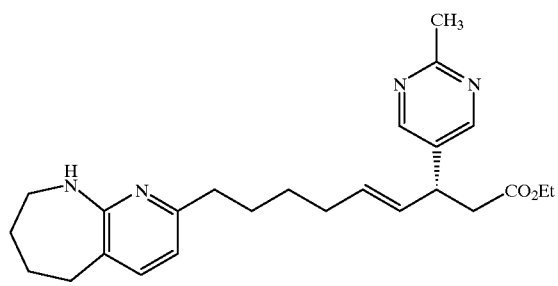
8-13

H₂, Pd/C

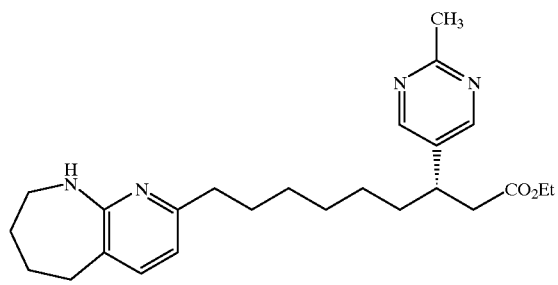
8-14

NaOH

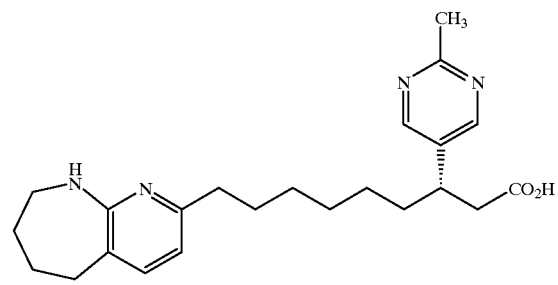
8-15

EXAMPLE 8

3(S)-(2-Methyl-pyrimidin-5-yl)-9-(6,7,8,9-tetrahydro-5H-pyrido[2,3-b]azepin-2-yl) nonanoic acid (8-15)

Example 8-15 was prepared as shown in Scheme 8 following procedures (Scheme 9) disclosed in U.S. Pat. No. 6,048,861 (Apr. 11, 2000) for the preparation of 3(S)-(2-methyl-pyrimidin-5-yl)-9-(5,6,7,8-tetrahydro-[1,8]-naphthyridin-2-yl)-nonanoic acid (9-4) and related structures. Resolution of the enantiomeric pair can be carried out by chiral BPLC chromatography at either the allylic alcohol intermediate stage (9-2) to give the resolved (R)- and (S)-alcohols or at the reduced ester stage (9-3) to give the resolved (R)- and (S)-esters, which can then be hydrolyzed to afford the enantiomerically pure final products.

Scheme 9

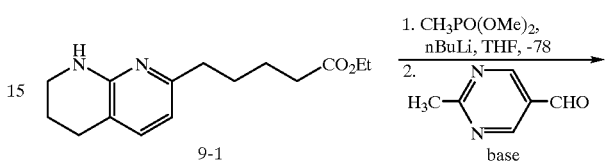
9-1

1. CH₃PO(OMe)₂, nBuLi, THF, -78
2. H₃C-pyrimidine-CHO, base
3. DIBALH or NaBH₄

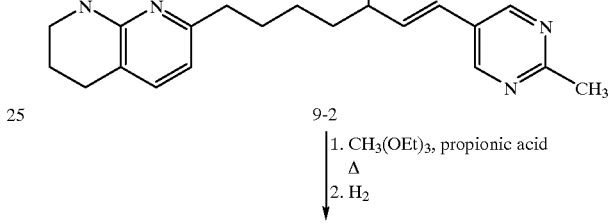
9-2

1. CH₃(OEt)₃, propionic acid Δ
2. H₂

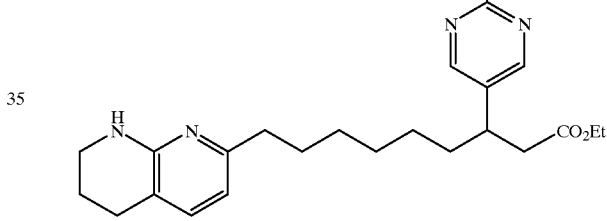
9-3 aq. base

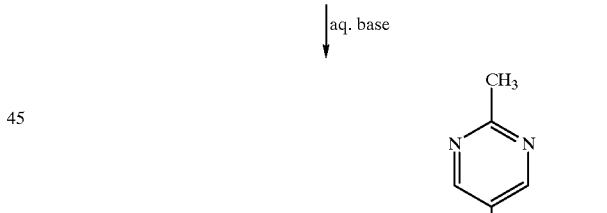
9-4

Step A: 5-(5-Bromo-pyridin-2-yl)-pentanoic acid ethyl ester (8-2)

To a stirred solution of ethyl-1-pentenoic acid (10 g, 78 mmol) in degassed THF (80 mL) at 0° C. was added dropwise a solution of 9-BBN (187 mL of 0.5 M in TBF, 94 mmol) and the mixture stirred for 18 hours at ambient temperature to produce 8-1. K₂CO₃ (18.4 g, 133 mmol) and 2,5-dibromopyridine (18.5 g, 78 mmol) were added, followed by a premixed and aged (70° C. for 30 min) suspension of Pd(OAc)₂ (2.0 g, 8.9 mmol) and DPPF (5.4 g, 9.8 mmol) in degassed DMF (80 mL). The resulting mixture was stirred for 18 hours at 70° C., cooled, diluted with ethyl acetate, washed with water and brine, dried over MgSO$_4$, and concentrated. To the stirring residue dissolved in THF (400 mL) was added water (150 mL) and NaHCO$_3$ (33 g) and after 10 minutes, NaBO$_3$.H$_2$O (48 g). After vigorous stirring for 30 minutes, the mixture was diluted with ethyl acetate, washed with water and brine, dried over MgSO$_4$, and concentrated to an oil. The residue was chromatographed on silica gel (10–20% EtOAc/hexane) to give 8-2 as a colorless oil.

TLC R$_f$=0.75 (silica, 40% EtOAc/hexane).

$^1$H NMR (400 MHz, CDCl$_3$): δ8.57 (s, 1H), 7.70 (m, 1H), 7.05 (d, 1H, J=8 Hz), 4.15 (q, 2H, J=6 Hz), 2.77 (t, 2H, J=7 Hz), 2.34 (t, 2H, J=7 Hz), 1.7 (m, 4H), 1.26 (t, 3H, J=6 Hz).

Step B: 2-But-3-enyl-isoindole-1,3-dione (8-5)

To a stirred solution of 4-bromo-1-butene (8-3, 20 g, 148 mmol) in DMF (150 mL) was added potassium phthalimide (8-4, 25 g, 133 mmol) and the mixture stirred for 18 hours at 70° C. After cooling to RT, the mixture was diluted with ether, washed with water and brine, dried over MgSO$_4$, and concentrated to give 8-5 as a white solid.

$^1$H NMR (400 MHz, CDCl$_3$): δ7.85 (m, 2H), 7.72 (m, 2H), 5.82 (m, 1H), 5.08 (m, 2H), 3.77 (t, 2H, J=7 Hz), 2.44 (m, 2H).

Step C: 5-{5-[4-(1,3-Dioxo-1,3-dihydro-isoindol-2-yl)-butyl]-pyridin-2-yl}-pentanoic acid ethyl ester (8-6)

To a stirred solution of 8-5 (4.23 g, 21 mmol) in degassed THF (20 mL) at 0° C. was added dropwise a solution of 9-BBN (50.4 mL of 0.5 M in TBF, 25.2 mmol) and the mixture stirred for 18 hours at ambient temperature. K$_2$CO$_3$ (5.0 g, 35.8 mmol) and 8-2 (5.0 g, 17.4 mmol) were added, followed by a premixed and aged (70° C. for 30 min) suspension of Pd(OAc)$_2$ (0.54 g, 2.4 mmol) and DPPF (1.45 g, 2.6 mmol) in degassed DMF (20 mL). The resulting mixture was stirred for 18 hours at 70° C., cooled, diluted with ethyl acetate, washed with water and brine, dried over MgSO$_4$, and concentrated. To the stirring residue dissolved in THF (200 mL) was added water (75 mL) and NaHCO$_3$ (16.5 g) and after 10 minutes, NaBO$_3$.H$_2$O (24 g). After vigorous stirring for 30 minutes, the mixture was diluted with ethyl acetate, washed with water and brine, dried over MgSO$_4$, and concentrated to an oil. The residue was chromatographed on silica gel (20–40% EtOAc/hexane) to give 8-6 as a yellow solid.

TLC R$_f$=0.31 (silica, 50% EtOAc/hexane). $^1$H NMR (400 MHz, CDCl$_3$): δ8.37 (s, 1H), 7.84 (m, 2H), 7.75 (m, 2H), 7.40 (m, 1H), 7.05 (m, 1H), 4.12 (q, 2H, J=7 Hz), 3.71 (m, 2H), 2.78 (t, 2H, J=7 Hz), 2.61 (t, 2H, J=7 Hz), 2.33 (t, 2H, J=7 Hz), 1.64 (m, 8H), 1.23 (t, 3H, J=6 Hz).

Step D: 5-[5-(4-Amino-butyl)-pyridin-2-yl]-pentanoic acid methylamide (8-7)

A mixture of 8-6 (45 g, 110 mmol) and a saturated solution of methylamine in methanol (300 mL) in a sealed tube was heated at 70° C. for 12 hours. The mixture was cooled and concentrated to an oil. The residue was chromatographed on silica gel (10:10:1:1 EtOAc/EtOH/NHOH/H$_2$O) to give 8-7 as a yellow oil.

TLC R$_f$=0.16 (silica, 10:10:1:1 EtOAc/EtOH/NH$_4$OH/H$_2$O). $^1$H NMR (400 MHz, CDCl$_3$): δ8.32 (s, 1H), 7.41 (m, 1H), 7.07 (m, 1H), 2.74 (m, 7H), 2.59 (t, 2H, J=6 Hz), 2.21 (t, 2H, J=6 Hz), 1.69 (m, 6H), 1.48 (m, 2H).

Step E: 5-(6,7,8,9-Tetrahydro-5H-pyrido[2,3-b]azepin-2-yl)-pentanoic acid methylamide (8-8)

A mixture of 8-7 (24 g, 91.2 mmol) and NaH (10.9 g of a 60% weight dispersion in mineral oil, 273 mmol) in xylenes (500 mL) was purged with argon for 30 min, and then heated at reflux for 72 hours. The mixture was cooled, quenched with ethanol, diluted with 10% aqueous potassium carbonate and extracted with ethyl acetate. The organics were dried over MgSO$_4$, and concentrated to an oil. The residue was chromatographed on silica gel (70:25:5 CHCl$_3$/EtOAc/MeOH/H$_2$O) to give 8-8 as a white solid.

TLC R$_f$=0.15 (silica, 70:25:5 CHCl$_3$/EtOAc/MeOH). $^1$H NMR (400 MHz, CDCl$_3$): δ7.24 (d, 1H, J=7 Hz), 6.53 (d, 1H, J=7 Hz), 5.43 (br s, 1H), 4.62 (br s, 1H), 3.12 (m, 2H), 2.79 (d, 3H, J=5 Hz), 2.63 (m, 4H), 2.18 (m, 2H), 1.81 (m, 2H), 1.68 (m, 6 Hz).

Step F: 5-(6,7,8,9-Tetrahydro-5H-pyrido[2,3-b]azepin-2-yl)-pentanoic acid ethyl ester (8-9)

A mixture of 8-8 (3 g, 11.5 mmol) and 6 M HCl (100 mL) in a sealed tube was heated at 70° C. for 12 hours. The mixture was cooled and concentrated to an oil. The residue was azeotroped from ethanol (50 mL) twice, then dissolved in 4 M HCl in ethanol (100 mL) and heated at 70° C. for 1 hour. The mixture was cooled and concentrated to an oil. The residue was diluted with ethyl acetate, washed with 10% aqueous potassium carbonate and brine, dried over MgSO$_4$, and concentrated to give 8-9 as a brown oil.

TLC R$_f$=0.44 (silica, 70:25:5 CHCl$_3$/EtOAc/MeOH). $^1$H NMR (400 MHz, CDCl$_3$): δ7.22 (d, 1H, J=7 Hz), 6.53 (d, 1H, J=7 Hz), 4.63 (br s, 1H), 4.11 (q, 2H, J=7 Hz), 3.12 (m, 2H), 2.66 (m, 2H), 2.62 (t, 2H, J=6 Hz), 2.33 (t, 2H, J=6 Hz), 1.70 (m, 2H), 1.63 (m, 6H), 1.27 (t, 3H, J=7 Hz).

Step G: 1-(2-Methyl-pyrimidin-5-yl)-7-(6,7,8,9-tetrahydro-5H-pyrido[2,3-b]azepin-2-yl)-hept-1-en-3(R)-ol (8-12)

8-9 was converted into 8-11 in a similar fashion as 7-4 was converted into 7-5. To a stirred solution of 8-11 (1.4 g, 3.99 mmol) in methanol (20 mL) at 0° C. was added NaBH$_4$ (0.166 g, 4.4 mmol) and the mixture stirred for 15 minutes. Concentrated HCl (aq) was added dropwise until the effervescence ceased (~10 drops). The mixture was then diluted with ethyl acetate, washed with water and brine, dried over MgSO$_4$, and concentrated. The residue was chromatographed on a Chiralpak AD 100 mm×500 mm column (50 (0.1% diethylamine in hexanes)/50 isopropanol) to give 8-12 as a white solid.

TLC R$_f$=0.19 (silica, 50% EtOAc/hexane). $^1$H NMR (400 MHz, CDCl$_3$) δ8.60 (s, 2H), 7.23 (d, 1H, J=8 Hz), 6.51 (m, 2H), 6.32 (m, 1H), 4.68 (br s, 1H), 4.37 (m, 1H), 3.13 (m, 2H), 2.73 (s, 3H), 2.64 (m, 4H), 1.91–1.43 (m, 11H).

Step H: 3(R)-(2-Methyl-pyrimidin-5-yl)-9-(6,7,8,9-tetrahydro-5H-pyrido[2,3-b]azepin-2-yl)-non-4-enoic acid ethyl ester (8-13)

A mixture of 8-12 (0.48 g, 1.36 mmol), triethyl orthoacetate (10 mL), and propionic acid (0.001 mL) was heated at 150° C. for 4 hours. Concentration gave 8-13, which was used directly in the next reaction.

TLC R$_f$=0.41 (silica, 70:20:10 CHCl$_3$/EtOAc/MeOH).

Step I: 3 (S)-(2-Methyl-pyrimidin-5-yl)-9-(6,7,8,9-tetrahydro-5H-pyrido[2,3-b]azepin-2-yl)-nonanoic acid ethyl ester (8-14)

A mixture of 8-13 (0.48 g, 1.36 mmol), 10% Pd/C (10 mL), and ethanol (10 mL) was stirred under a balloon of hydrogen for 4 hours. Filtration and concentration gave 8-14 as a yellow oil.

$^1$H NMR (400 MHz, CDCl$_3$) δ8.47 (s, 2H), 7.22 (d, 1H, J=8 Hz), 6.51 (d, 1H, J=8 Hz), 4.67 (br s, 1H), 4.03 (m, 2H), 3.49 (m, 2H), 3.08 (m, 3H), 2.63 (m, 7H), 2.52 (m, 3H), 1.78 (m, 4H), 1.61 (m, 7H), 1.28 (t, 3H, J=7 Hz).

Step J: 3(S)-(2-Methyl-pyrimidin-5-yl)-9-(6,7,8,9-tetrahydro-5H-pyrido[2,3-b]azepin-2-yl)-nonanoic acid (8-15)

To a solution of 8-14 (0.50 g, 1.36 mmol) in ethanol (10 mL) was added 1N NaOH (1.5 mL), and the mixture stirred at 50° C. for 30 minutes, then concentrated. The residue was chromatographed on silica gel (25:10:1:1 to 15:10:1:1 EtOAc/EtOH/NH₄OH/H₂O) to give 8-15 as a yellow solid.

TLC R_f=0.21 (silica, 15:10:1:1 EtOAc/EtOH/NH₄OH/H₂O). $^1$H NMR (400 MHz, CD$_3$OD) δ8.58 (s, 2H), 7.42 (d, 2H, J=8 Hz), 6.58 (d, 1H, J=8 Hz), 3.27 (m, 2H), 3.13 (m, 1H), 2.75 (m, 2H), 2.63 (m, 8H), 1.82 (m, 4H), 1.61 (m, 3H), 1.32 (m, 6H).

Scheme 10

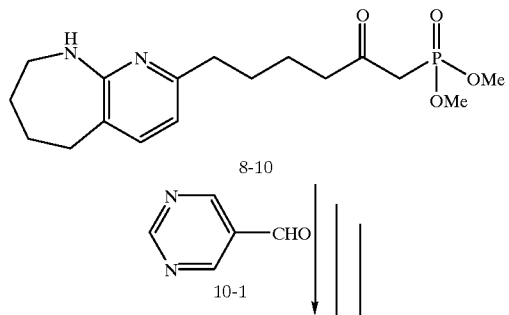

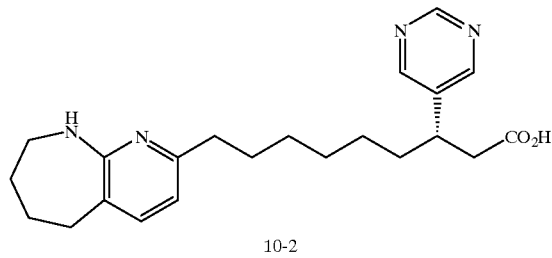

EXAMPLE 9

3(S)-Pyrimidin-5-yl-9-(6,7,8,9-tetrahydro-5H-pyrido[2,3-b]azepin-2-yl)-nonanoic acid (10-2)

Using the procedures shown in Scheme 8 above for the synthesis of 8-10 and its conversion into 8-15, 8-10 and 5-formyl-pyrimidine (10-1) were converted into 10-2.

TLC R_f=0.17 (silica, 15:10:1:1 EtOAc/EtOH/NH₄OH/H₂O). $^1$H NMR (400 MHz, CD$_3$OD) δ9.00 (s, 1H), 8.70 (s, 2H), 7.42 (d, 2H, J=8 Hz), 6.59 (d, 1H, J=8 Hz), 3.29 (m, 2H), 3.18 (m, 1H), 2.8–2.58 (m, 6H), 1.9–1.56 (m, 8H), 1.38–1.25 (m, 6H).

SCHEME 11

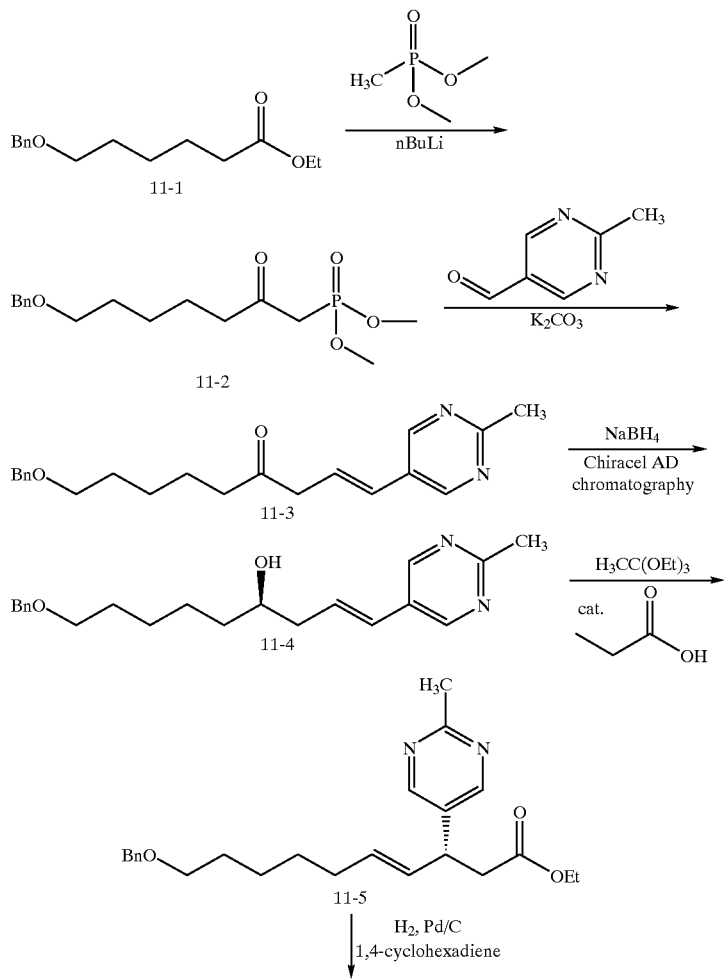

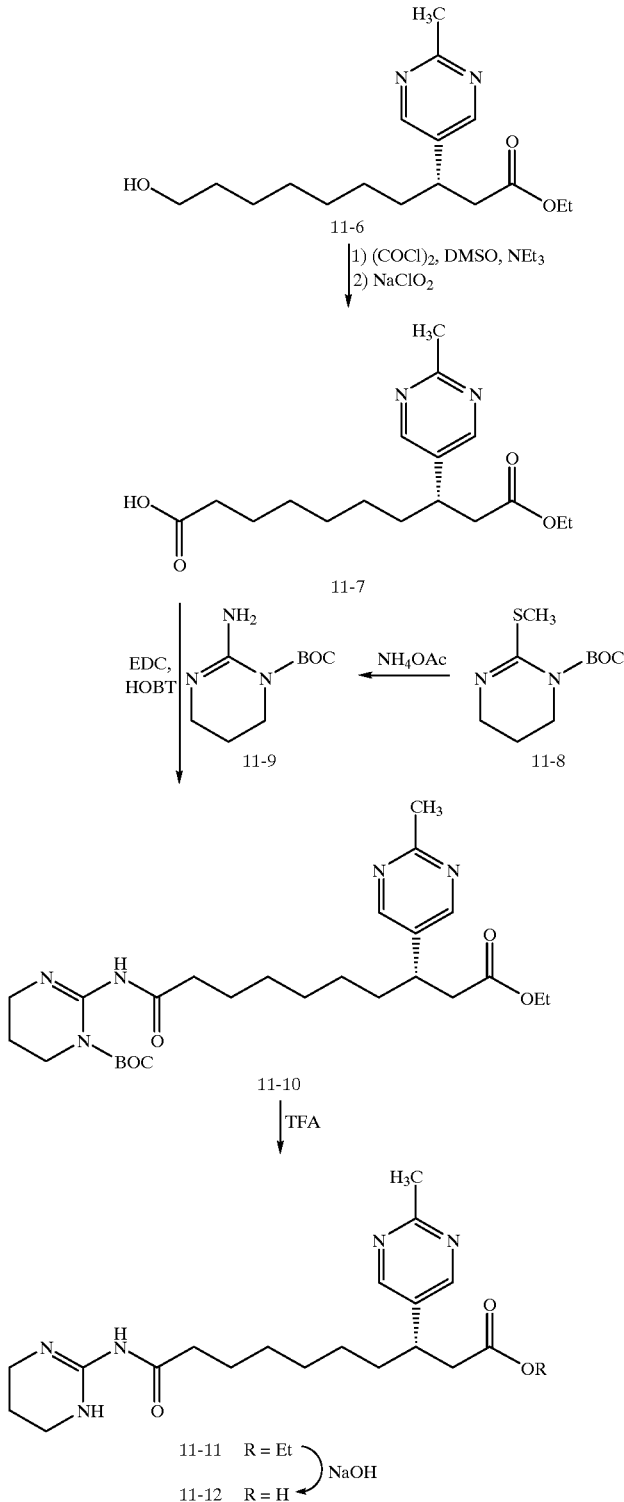

EXAMPLE 10

(7-Benzyloxy-2-oxo-heptyl)-phosphonic acid dimethyl ester (11-2)

To a solution of methyl dimethylphosphonate (18 mL, 166 mmol) in TBF (200 mL) at −78° C. was added n-butyllithium (66.3 mL 2.5 M in hexane, 66.3 mmol) over 30 minutes. After an additional hour, 6-benzyloxy-hexanoic acid ethyl ester (10.4 g, 41.5 mmol; for preparation see: Sime, et al, *J. Chem. Soc., Perkin Trans.* 1, 13 1653 (1992)) was added in 30 mL TIF over 15 minutes. The mixture was stirred for 1 hour, then quenched by the addition of saturated NH₄Cl (30 mL). Following warming, the THF was evaporated, and the residue diluted with water, and extracted with ethyl acetate. The extracts were then washed with water and brine, then dried over magnesium sulfate. Evaporation of the solvents gave 10.0 g (73%) of 11-2 as a yellow oil.

TLC $R_f$=0.18 (silica, EtOAc) $^1$H NMR (300 MHz, CDCl$_3$) δ7.31 (m, 5H), 4.47 (s, 2H), 3.77 (d, 6H, J=11 Hz), 3.42 (t, 2H), 3.08 (d, 2H, J=23 Hz), 2.60 (t, 2H), 1.61 (m, 4H), 1.37 (m, 2H).

9-Benzyloxy-1-(2-methyl-pyrimidin-5-yl)-non-1-en-4-one (11-3)

A mixture of 11-2 (4.4 g, 13.8 mmol), 2-methyl-pyrimidine-5-carbaldehyde (1.5 g, 12.5 mmol; for preparation, see J. Heterocyclic Chem., 28, 1281 (1991)) potassium carbonate (3.1 g, 25 mmol) and THF (200 mL) was heated at 60° C. for 3 hours. Following cooling, the mixture was diluted with ethyl acetate, washed with sat. NaHCO$_3$ and brine, and dried over magnesium sulfate. Evaporation of the solvents gave 4.0 g (100%) of 11-3 as a white solid.

TLC $R_f$=0.51 (silica, EtOAc) $^1$H NMR (300 MHz, CDCl$_3$) δ8.79 (s, 2H), 7.43 (d, 1H, J=16 Hz), 7.35 (m, 5H), 6.82 (d, 1H, J=16 Hz), 4.47 (s, sH), 3.46 (t, 2H), 2.77 (s, 3H), 2.63 (t, 2H), 1.67 (m, 4H), 1.39 (m, 2H).

9-Benzyloxy-1-(2-methyl-pyrimidin-5-yl)-non-1-en-4(R)-ol (11-4)

To a solution of 11-3 (4.0 g, 12.3 mmol) in methanol (150 mL) at −15° C. was added sodium borohydride (0.515 g, 13 mmol). After 10 minutes, conc. HCl was added until bubbling ceased, and then sat. NaHCO$_3$ was added to reach pH=10. The mixture was warmed to room temperature, the methanol removed, and the residue diluted with ethyl acetate, washed with sat. NaHCO$_3$ and brine, and dried over magnesium sulfate. Evaporation of the solvents gave a residue which was purified on a 10×50 cm Chiralpak AD column (flow=200 ml/min, A:B=20:80) (A=0.1% diethylamine/hexane, B=ethanol). Product 11-4 elutes at 21 minutes, providing 1.7 g of 11-4 (84% yield of theoretical); its enantiomer elutes at 45 minutes.

$^1$H NMR (300 MHz, CDCl$_3$) δ8.61 (s, 2H), 7.32 (m, 5H), 6.48 (d, 1H, J=16 Hz), 6.31 (dd, 1H, J=6, 16 Hz), 4.47 (s, 2H), 4.28 (m, 1H), 3.42 (t, 2H), 3.02 (s, 2H), 2.71 (s, 3H), 2.36 (s, 1H), 1.61 (m, 4H), 1.42 (m, 2H).

10-Benzyloxy-3(R)-(2-methyl-pyrimidin-5-yl)-dec-4-enoic acid ethyl ester (11-5)

A mixture of 11-4 (1.6 g, 4.9 mmol), triethylorthoacetate (50 mL), and propionic acid (0.004 mL) was heated at 150° C. for 6 hours. Following cooling and concentration, the mixture was diluted with ethyl acetate, washed with sat. NaHCO$_3$ and brine, and dried over magnesium sulfate. Evaporation of the solvents gave 1.2 g (97%) of 11-5 as a yellow oil.

TLC $R_f$=0.65 (silica, EtOAc) $^1$H NMR (300 MHz, CDCl$_3$) δ8.48 (s, 2H), 7.33 (m, 5H), 5.48 (m, 2H), 4.46 (s, 2H), 4.09 (q, 2H), 3.78 (m, 1H), 3.42 (m, 2H), 2.68 (m, 5H), 1.60 (m, 4H), 1.37 (m, 2H), 1.21 (t, 3H).

10-Hydroxy-3(S)-(2-methyl-pyrimidin-5-yl)-decanoic acid ethyl ester (11-6)

A mixture of 11-5 (1.2 g, 4.9 mmol), 10% Pd/C (1.0 g), 1,4-cyclohexadiene (10 mL), and acetic acid (30 mL) was purged with argon, and then heated at 80° C. for 6 hours. Following cooling, filtration and concentration, the mixture was diluted with ethyl acetate, washed with 10%. K$_2$CO$_3$ and brine, and dried over magnesium sulfate. Evaporation of the solvents gave 0.65 g (88%) of 11-6 as a yellow oil.

TLC $R_f$=0.19 (silica, EtOAc) $^1$H NMR (300 MHz, CDCl$_3$) δ8.48 (s, 2H), 4.08 (q, 2H), 3.62 (t, 2H), 3.04 (m, 1H), 2.68 (s, 3H), 7.61 (m, 2H), 1.63 (m, 6H), 1.28 (m, 6H), 1.21 (t, 3H).

3(S)-(2-Methyl-pyrimidin-5-yl)-decanedioic acid 1-ethyl ester (11-7)

To a mixture of oxalyl chloride (0.215 mL, 2.5 mmol) and dichloromethane (7 mL) at −78° C. was added DMSO (0.25 mL, 3.2 mmol) dropwise. After 15 minutes, 11-6 (0.55 g, 1.8 mmol) was added in 2 mL dichloromethane, and the resulting solution stirred for 30 minutes. Triethylamine was then added, and after 30 minutes, the mixture warmed to room temperature, diluted with ethyl acetate, washed with water and brine, and dried over magnesium sulfate. Evaporation of the solvents gave 0.45 g (82%) of the intermediate aldehyde as a yellow oil. To a solution of this oil in tert-butanol (3 mL), 2-methyl-2-butene (0.5 mL), and water (1 mL) was added a freshly prepared solution of NaH$_2$PO$_4$ (0.61 g, 4.5 mmol) and sodium chlorite (0.275 g, 2.8 mmol) in water (3 mL). After 30 minutes, the mixture was concentrated, and the residue chromatographed on silica gel (25:10:1:1 to 15:10:1:1 ethyl acetate/ethanol/NH$_4$OH/water) to give 11-7 as a white solid (0.24 g, 79%).

TLC $R_f$=0.35 (silica, 15:10:1:1 ethyl acetate/ethanol/ NH$_4$OH/water) $^1$H NMR (400 MHz, CD$_3$OD) δ8.60 (s, 2H), 4.01 (q, 2H), 3.12 (s, 1H), 2.71 (m, 2H), 2.64 (s, 3H), 2.22 (t, 2H), 1.73 (m, 2H), 1.56 (m, 2H), 1.29 (m, 6H), 1.10 (t, 3H).

2-Amino-5,6-dihydro-4H-pyrimidine-1-carboxylic acid tert-butyl ester (11-9)

A mixture of 2-methylsulfanyl-5,6-dihydro-4H-pyrimidine-1-carboxylic acid tert-butyl ester (14 g, 60.8 mmol; prepared according to Godlewski, et al, WO98/23595, PCT/US97/21646), ammonium acetate (14 g, 182 mmol) acetic acid (10 mL) and methanol (90 mL) was heated at 50° C. for 20 hours. Evaporation of the solvents at 50° C. and 10 mm Hg gave concomitant sublimation of some of the remaining ammonium acetate. The resulting residue was diluted with water (40 mL), adjusted to pH=10 with sat. K$_2$CO$_3$, saturated with NaCl, and extracted with 4×200 mL ethyl acetate. The organics were dried over magnesium sulfate, and concentrated to give 6.1 g (50%) of 11-9 as a white solid.

$^1$H NMR (400 MHz, CDCl$_3$) δ3.78 (t, 2H, J=6 Hz), 3.38 (t, 2H, J=6 Hz), 2.03 (m, 4H), 1.58 (s, 9H).

3(S)-(2-Methyl-pyrimidin-5-yl)-9-(1,4,5,6-tetrahydro-pyrimidin-2-ylcarbamoyl)-nonanoic acid (11-12)

A mixture of 11-7 (0.4 g, 1.2 mmol), 11-9 (0.33 g, 1.4 mmol), EDC (0.35 g, 1.4 mmol), and HOBT (0.19 g, 1.2 mmol) in DME (3 mL) was stirred for 18 hours. Following concentration, the mixture was diluted with ethyl acetate, washed with 20% K$_2$CO$_3$ and brine, and dried over magnesium sulfate. Evaporation of the solvents gave 0.70 g of crude 11-10 as a yellow oil. To a solution of this oil in dichloromethane (5 mL) was added TFA (5 mL). After 1 hour, the reaction was concentrated, the residue dissolved in ethyl acetate, washed with 10% K$_2$CO$_3$ and brine, and dried over magnesium sulfate. Evaporation of the solvents gave 0.55 g crude 11-11 as a yellow oil. To a solution of this oil in ethanol (5 mL) was added 1N NaOH (1.5 mL). After 1 hour, the reaction was concentrated, and the residue chromatographed on silica gel (25:10:1:1 to 15:10:1:1 ethyl acetate/ethanol/NH$_4$OH/water) to give 11-12 as a white solid (0.16 g, 36%).

TLC R$_f$=0.18 (silica, 10:10:1:1 ethyl acetate/ethanol/NH$_4$OH/water) $^1$H NMR (400 MHz, CD$_3$OD) δ8.58 (s, 2H), 3.42 (m, 4H), 3.18 (m, 1H), 2.62 (s, 3H), 2.57 (m, 1H), 2.43 (m, 2H), 2.34 (m, 1H), 1.94 (t, 2H), 1.78 (m, 1H), 1.63 (m, 3H), 1.43 (m, 1H), 1.26 (m, 4H). High resolution mass spectrum: calculated for C$_{19}$H$_{29}$N$_5$O$_3$, M+1=376.2343, measured 376.2344.

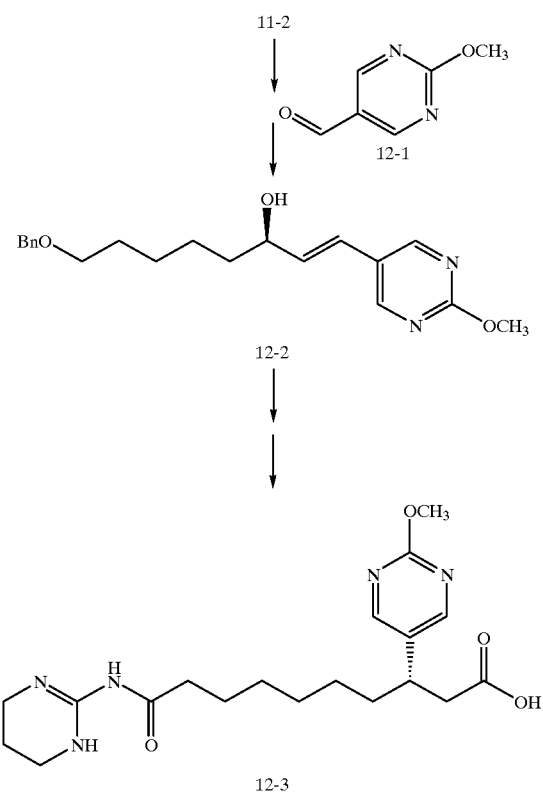

EXAMPLE 11

3(S)-(2-Methoxy-pyrimidin-5-yl)-9-(1,4,5,6-tetrahydro-pyrimidin-2-ylcarbamoyl)-nonanoic acid (12-3)

Utilizing the procedure for the preparation of 11-4, 11-2 and 12-1 [for preparation, see *J. Heterocycl. Chem.* (1991), 28, 1281)] were converted into 12-2, which was purified by chromatography on a Chiralcel AS column: 5×50 cm; flow= 100 mL/min, A:B=80:20 to 20:80 over 60 minutes (A=0.1% diethylamine/hexane, B=ethanol). Product 12-2 eluted first. 12-2 was then subjected to the procedure for the conversion of 11-4 to 11-12, resulting in 12-3.

TLC R$_f$=0.19 (silica, 10:10:1:1 ethyl acetate/ethanol/NH$_4$OH/water). $^1$H NMR (400 MHz, CD$_3$OD): δ8.42 (s, 2H), 3.97 (s, 3H), 3.96 (t, 4H), 3.17 (m, 1H), 2.60–2.35 (m, 4H), 2.04 (m, 2H), 1.78 (m, 2H), 1.63 (m, 3H), 1.46 (m, 1H), 1.36 (m, 4H).

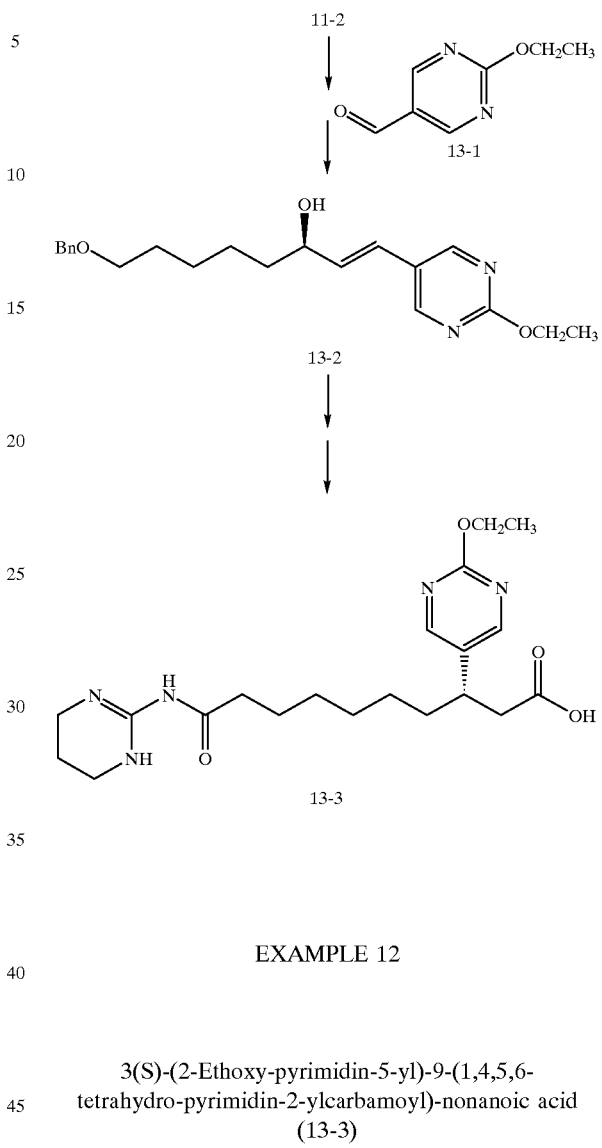

EXAMPLE 12

3(S)-(2-Ethoxy-pyrimidin-5-yl)-9-(1,4,5,6-tetrahydro-pyrimidin-2-ylcarbamoyl)-nonanoic acid (13-3)

Utilizing the procedure for the preparation of 11-4, 11-2 and 13-1 [for preparation, see *J. Heterocycl. Chem.* (1991), 28, 1281)] were converted into 13-2, which was purified by chromatography on a Chiralcel AS column: 5×50 cm; flow= 100 mL/min, A:B=80:20 to 20:80 over 60 minutes (A=0.1% diethylamine/hexane, B=ethanol). Product 13-2 eluted first. 13-2 was then subjected to the procedure for the conversion of 11-4 to 11-12, resulting in 13-3.

TLC R$_f$=0.32 (silica, 15:10:1:1 ethyl acetate/ethanol/NH$_4$OH/water). $^1$H NMR (400 MHz, CD$_3$OD): δ8.42 (s, 2H), 4.40 (q, 2H, J=7 Hz), 3.44 (t, 4H, J=6 Hz), 3.15 (m, 1H), 2.55 (m, 1H), 2.45 (m, 2H), 2.34 (m, 1H), 1.99 (m, 2H), 1.76 (m, 1H), 1.64 (m, 3H), 1.47 (m, 1H), 1.39 (t, 3H, J=7 Hz), 1.30 (m, 5H).

SCHEME 14

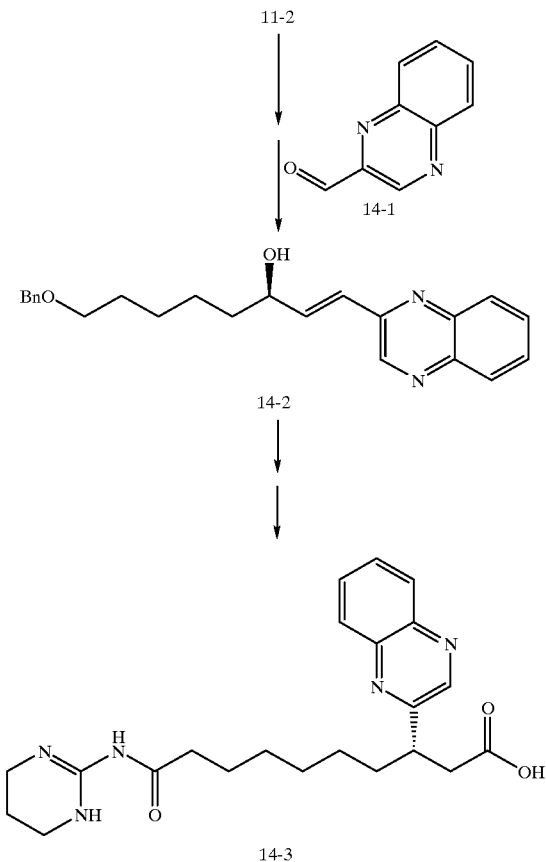

SCHEME 15

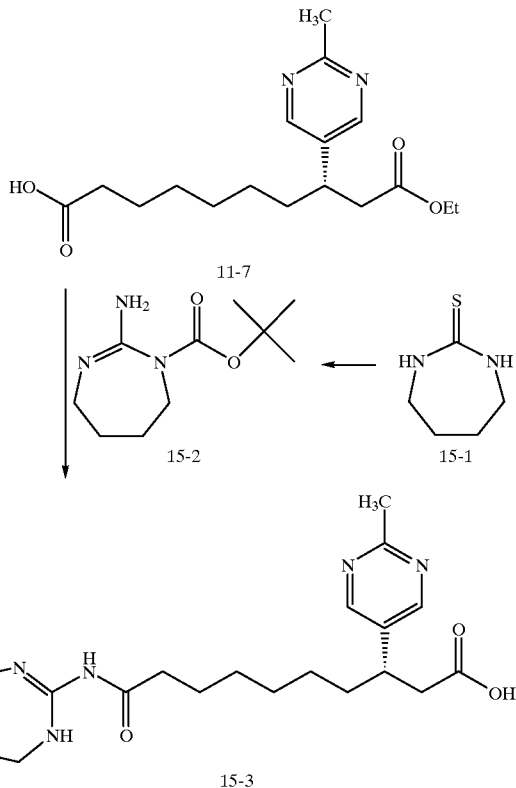

EXAMPLE 13

3(S)-Quinoxalin-2-yl-9-(1,4,5,6-tetrahydro-pyrimidin-2-ylcarbamoyl)-nonanoic acid (14-3)

Utilizing the procedure for the preparation of 11-4, 11-2 and 14-1 [for preparation, see *J. Org. Chem.* 1986, 51, 536)] were converted to 14-2, which was purified by chromatograph on a Chiralcel AD column: 10×50 cm; flow=240 mL/min, A:B: C=40:40:20 for 40 min, then 20:0:80 for 30 minutes (A=0.1% diethylamine/hexane, C=ethanol). Product 14-2 eluted during the first eluant mixture, and the enantiomer during the second. 14-2 was then subjected to the procedure for the conversion of 11-4 to 11-12, resulting in 14-3.

TLC $R_f$=0.27 (silica, 15:10:1:1 ethyl acetate/ethanol/NH$_4$OH/water).

$^1$H NMR (400 MHz, CD$_3$OD): δ8.81 (s, 1H), 8.02 (d, 2H, J=7 Hz), 7.75 (m, 2H), δ3.63 (m, 1H), 3.39 (t, 4H, J=6 Hz), 2.76 (m, 2H), 2.37 (m, 2H), 1.93 (m, 4H), 1.61 (m, 2H), 1.45 (m, 1H), 1.30 (m, 5H).

EXAMPLE 14

2-Amino-4,5,6,7-tetrahydro-[1,3]diazepine-1-carboxylic acid tert-butyl ester (15-2)

[1,3]Diazepane-2-thione (15-1) (prepared according to Tomcufcic, et al, U.S. Pat. No. 4,344,954) was converted into 15-2 utilizing the procedures of Godlewski, et al., published in WO98/23595.

$^1$H NMR (400 MHz, CDCl$_3$) δ6.18 (br s, 2H), 3.60 (m, 2H), 3.24 (m, 2H), 1.77 (m, 4H), 1.51 (s, 9H).

3(S)-(2-Methyl-pyrimidin-5-yl)-9-(4,5,6,7-tetrahydro-1H-[1,3]diazepin-2-ylcarbamoyl)-nonanoic acid (15-3)

11-7 and 15-2 were converted into 15-3 utilizing the procedure for the conversion of 11-7 to 11-12.

TLC $R_f$=0.26 (silica, 15:10:1:1 ethyl acetate/ethanol/NH$_4$OH/water). $^1$H NMR (400 MHz, CD$_3$OD) δ8.58 (s, 2H), 3.52 (m, 4H), 3.22 (m, 1H), 2.64 (s, 3H), 2.48 (m, 3H), 2.36 (m, 1H), 1.82 (m, 5H), 1.62 (m, 4H), 1.33 (m, 5H).

SCHEME 16
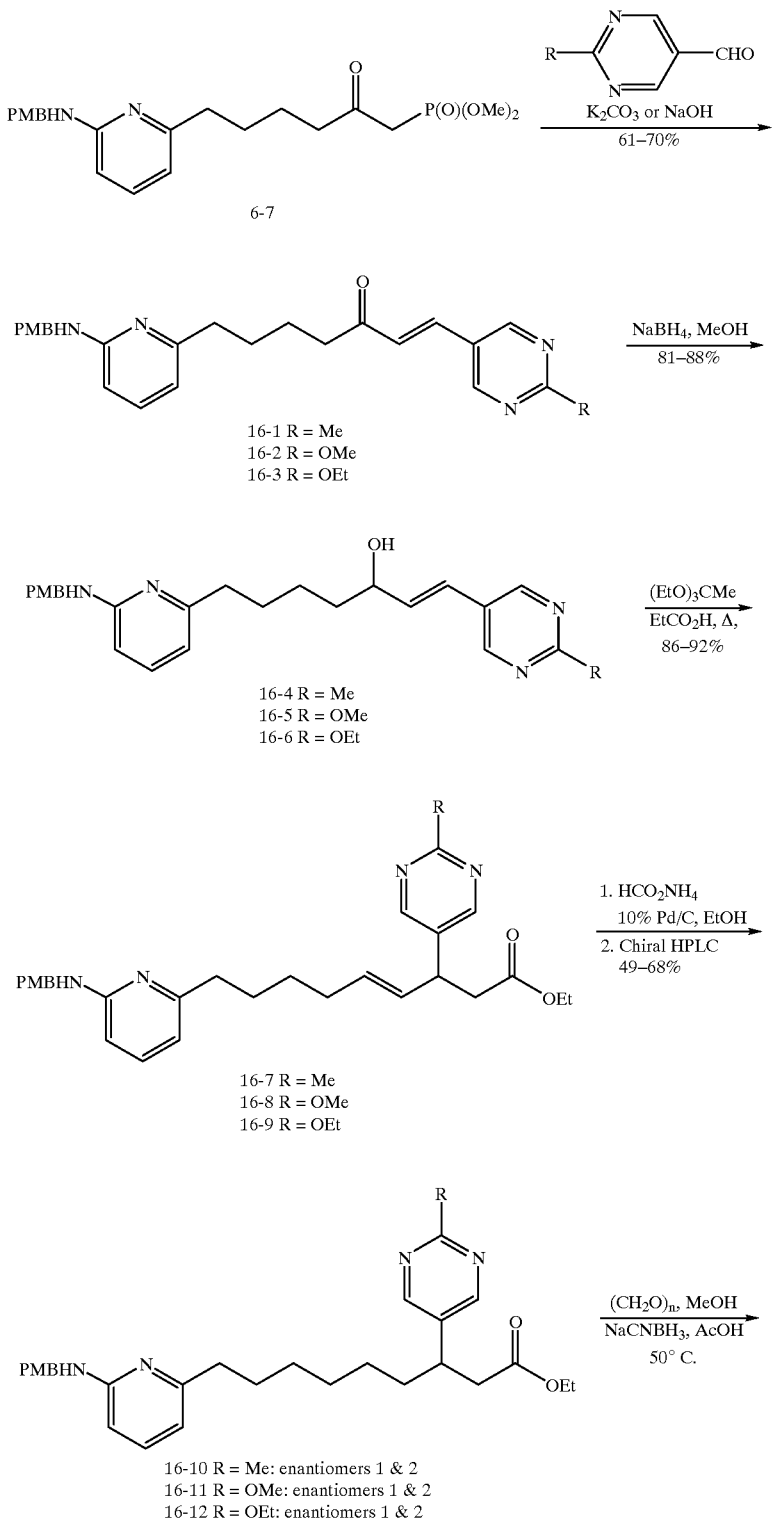

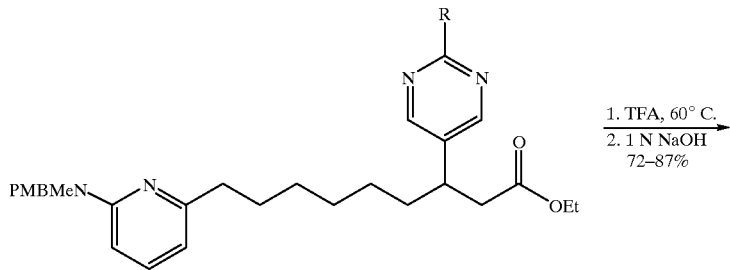

16-13 R = Me: enantiomers 1 & 2
16-14 R = OMe: enantiomers 1 & 2
16-15 R = OEt: enantiomers 1 & 2

1. TFA, 60° C.
2. 1 N NaOH
72–87%

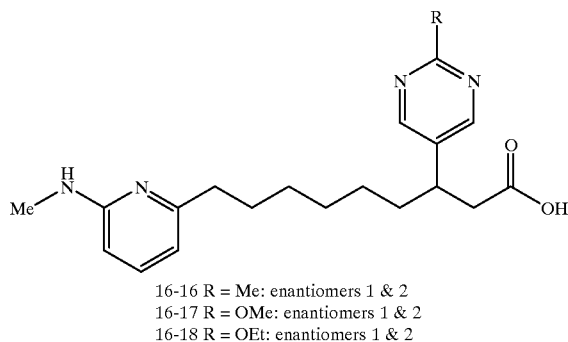

16-16 R = Me: enantiomers 1 & 2
16-17 R = OMe: enantiomers 1 & 2
16-18 R = OEt: enantiomers 1 & 2

EXAMPLES 15–17

3(R)- and 3(S)-9-(6-Methylamino-pyridin-2-yl)-3-(2-methyl-pyrimidin-5-yl)-nonanoic acid (1-16);

3(R)- and 3(S)-3-(2-Methoxy-pyrimidin-5-yl)-9-(6-methylamino-pyridin-2-yl)-nonanoic acid (16-17); and 3(R)- and 3(S)-3-(2-Ethoxy-pyrimidin-5-yl)-9-(6-methylamino-pyridin-2-yl)-nonanoic acid (16-18)

Step A: 7-[6-(4-Methoxy-benzylamino)-pyridin-2-yl]-1-(2-methyl-pyrimidin-5-yl)-hept-1-en-3-one (16-1)

To a solution of 6-7 (42.8 g, 102 mmol) and 2-methylpyrimidine-5-carbaldehyde (12.45 g, 102 mmol) in THF (250 mL) at 0° was added 4M NaOH (26.7 mL, 107 mmol) dropwise. After 15 minutes the ice bath was removed and the mixture stirred for an additional 10 minutes. The solution was diluted with water, extracted with ethyl acetate, and dried (Na$_2$SO$_4$). Following concentration, the residue was triturated with ether to give 27.7 g (61%) of 16-1 as a white solid.

$^1$H NMR (400 MHz, CDCl$_3$) 8.78 (s, 2H), 7.33 (m, 4H), 6.85 (m, 3H), 6.46 (d, J=7.1 Hz, 1H), 6.19 (d, J=8.3 Hz, 1H), 4.80 (br s, 1H), 4.39 (d, J=5.6 Hz, 2H), 3.80 (s, 3H), 2.78 (s, 3H), 2.67 (m, 4H), 1.76 (m, 4H). MS (M$^+$+H) 417.0.

7-[6-(4-Methoxy-benzylamino)-pyridin-2-yl]-1-(2-methoxy-pyrimidin-5-yl)-hept-1-en-3-one (16-2)

$^1$H NMR (400 MHz, CDCl$_3$) 8.67 (s, 2H), 7.33 (m, 4H), 6.78 (m, 3H), 6.46 (d, J=7.2 Hz, 1H), 6.19 (d, J=8.2 Hz, 1H), 4.78 (t, J=5.7 Hz, 1H), 4.37 (d, J=5.7 Hz, 2H), 4.06 (s, 3H), 3.79 (s, 3H), 2.66 (m, 4H), 1.75 (m, 4H). MS (M$^+$+H) 433.0.

1-(2-Ethoxy-pyrimidin-5-yl)-7-[6-(4-methoxy-benzylamino)-pyridin-2-yl]-hept-1-en-3-one (16-3)

$^1$H NMR (400 MHz, CDCl$_3$) 8.66 (s, 2H), 7.32 (m, 4H), 6.78 (m, 3H), 6.46 (d, J=7.2 Hz, 1H), 6.19 (d, J=8.2 Hz, 1H), 4.79 (t, J=5.7 Hz, 1H), 4.47 (q, J=7.1 Hz, 2H), 4.37 (d, J=5.7 Hz, 2H), 3.79 (s, 3H), 2.66 (m, 4H), 1.75 (m, 4H), 1.45 (t, J=7.1 Hz, 3H). MS (M$^+$+H) 447.0.

Step B: 7-[6-(4-Methoxy-benzylamino)-pyridin-2-yl]-1-(2-methyl-pyrimidin-5-yl)-hept-1-en-3-ol (16-4)

A solution of the enone 16-1 (2.65 g, 6.36 mmol) in MeOH (150 mL) at 0° was treated with NaBH$_4$ (0.264 g, 6.99 mmol). The ice bath was removed and the solution was stirred at room temperature for 1 hr. The reaction was quenched with water (25 mL) and extracted with EtOAc (3×125 mL). The organics were combined, dried (Na$_2$SO$_4$), concentrated in vacuo, and purified on silica gel (90:5:5 CHCl$_3$:EtOAc:MeOH) to afford 2.35 g of 16-4.

$^1$H NMR (400 MHz, CDCl$_3$) 8.61 (s, 2H), 7.28 (m, 3H), 6.86 (m, 2H), 6.47 (m, 2H), 6.32 (m, 1H), 6.18 (d, J=8.2 Hz, 1H), 4.88 (t, J=5.7 Hz, 1H), 4.35 (m, 3H), 3.79 (s, 3H), 2.72 (s, 3H), 2.63 (t, J=7.4 Hz, 2H), 1.71 (m, 7H). MS (M$^+$+H) 419.1.

7-[6-(4-Methoxy-benzylamino)-pyridin-2-yl]-1-(2-methoxy-pyrimidin-5-yl)-hept-1-en-3-ol (16-5)

$^1$H NMR (400 MHz, CDCl$_3$) 8.51 (s, 2H), 7.30 (m, 3H), 6.86 (m, 2H), 6.46 (m, 2H), 6.20 (m, 2H), 4.86 (t, J=5.7 Hz, 1H), 4.37 (m, 2H), 4.32 (m, 1H), 4.01 (s, 3H), 3.79 (s, 3H), 2.63 (t, J=7.5 Hz, 2H), 1.57 (m, 7H). MS (M$^+$+H) 435.1.

1-(2-Ethoxy-pyrimidin-5-yl)-7-[6-(4-methoxy-benzylamino)-pyridin-2-yl]-hept-1-en-3-ol (16-6)

$^1$H NMR (400 MHz, CDCl$_3$) 8.48 (s, 2H), 7.30 (m, 3H), 6.86 (m, 2H), 6.45 (m, 2H), 6.19 (m, 2H), 4.86 (t, J=5.7 Hz, 1H), 4.41 (q, J=7.1 Hz, 2H), 4.38 (m, 2H), 4.31 (m, 1H), 3.79 (s, 3H), 2.63 (t, J=7.4 Hz, 2H), 1.57 (m, 7H), 1.43 (t, J=7.1 Hz, 3H). MS (M$^+$+H) 449.1.

Step C: (±)9-[6-(4-Methoxy-benzylamino)-pyridin-2-yl]-3-(2-methyl-pyrimidin-5-yl)-non-4-enoic acid ethyl ester (16-7)

A solution of the allylic alcohol 16-4 (2.3 g, 5.49 mmol) in (EtO)$_3$CMe (10 mL) was treated with 100 uL of a 1 mL solution of (EtO)₃CMe containing 10 uL of propionic acid. The yellow solution was heated at 150° for 90 minutes. The solution was cooled to room temperature and poured into 1N HCl/brine. The mixture was extracted with CHCl₃, dried, concentrated, and purified on silica gel (90:5:5 CHCl₃:EtOAc:MeOH) to give 2.32 g (86%) of 16-7.

¹H NMR (400 MHz, CDCl₃) 8.50 (s, 2H), 7.44 (dd, J=7.2, 8.8 Hz, 1H), 7.27 (m, 2H), 6.87 (m, 2H), 6.44 (d, J=7.2 Hz, 1H), 6.30 (d, J=8.8 Hz, 1H), 5.52 (m, 2H), 4.40 (d, J=3.6 Hz, 2H), 4.06 (q, J=7.2 Hz, 2H), 3.80 (m, 4H), 2.70 (m, 7H), 2.05 (m, 3H), 1.73 (m, 2H), 1.41 (m, 2H), 1.17 (t, J=7.1 Hz, 3H). MS (M⁺+H) 489.1.

(±)9-[6-(4-Methoxy-benzylamino)-pyridin-2-yl]-3-(2-methoxy-pyrimidin-5-yl)-non-4-enoic acid ethyl ester (16-8)

¹H NMR (400 MHz, CDCl₃) 8.37 (s, 2H), 7.50 (dd, J=7.2, 8.8 Hz, 1H), 7.28 (m, 2H), 6.88 (m, 2H), 6.46 (d, J=7.2 Hz, 1H), 6.37 (d, J=8.8 Hz, 1H), 5.52 (m, 2H), 4.42 (d, J=5.8 Hz, 2H), 4.07 (q, J=7.1 Hz, 2H), 3.99 (s, 3H), 3.78 (m, 4H), 2.69 (m, 4H), 2.07 (m, 3H), 1.73 (m, 2H), 1.42 (m, 2H), 1.19 (t, J=7.1 Hz, 3H). MS (M⁺+H) 505.1.

(±)3-(2-Ethoxy-pyrimidin-5-yl)-9-[6-(4-methoxy-benzylamino)-pyridin-2-yl]-non-4-enoic acid ethyl ester (16-9)

¹H NMR (400 MHz, CDCl₃) 8.35 (s, 2H), 7.30 (m, 3H), 6.86 (m, 2H), 6.42 (d, J=7.3 Hz, 1H), 6.18 (d, J=8.1 Hz, 1H), 5.51 (m, 2H), 4.39 (m, 4H), 4.06 (q, J=7.4 Hz, 2H), 3.77 (m, 4H), 2.63 (m, 4H), 2.04 (m, 3H), 1.66 (m, 2H), 1.41 (m, 5H), 1.17 (t, J=7.1 Hz, 3H). MS (M⁺+H) 519.1.

Step D: 3(R)- and 3(S)-9-[6-(4-Methoxy-benzylamino)-pyridin-2-yl]-3-(2-methyl-pyrimidin-5-yl)-nonanoic acid ethyl ester (16-10)

A solution of the 16-7 (2.3 g, 4.70 mmol) in 150 mL absolute EtOH was treated with 10% Pd—C (0.23 g, 10% by wt) at room temperature under an argon atmosphere. Then ammonium formate (1.78 g, 28.2 mmol) was added and the heterogeneous mixture was refluxed for 30 minutes. The reaction was >50% complete (by mass spectroscopy). At this point, more Pd—C (0.115 g, 5% by wt) and ammonium formate (0.89, 14.1 mmol) were added and the mixture refluxed for an additional 30 minutes (reaction complete by mass spectroscopy). The solution was then filtered through a Celite plug, washed with EtOH (200 mL), and concentrated in vacuo. The residue was chromatographed on silica gel (90:10:1 CHCl₃:MeOH:NOH) to give 16-10, which was resolved on a chiral AD column 240 ml/min 65:35 EtOH:Hex with 0.1% DEA. 0.53 g of enantiomer 1 and 0.51 g of enantiomer 2 were obtained from Prep HPLC.

¹H NMR (400 MHz, CDCl₃) 8.47 (s, 2H), 7.30 (m, 3H), 6.86 (m, 2H), 6.42 (d, J=7.3 Hz, 1H), 6.18 (d, J=8.2 Hz, 1H), 4.92 (br s, 1H), 4.37 (m, 2H), 4.03 (q, J=7.1 Hz, 2H), 3.79 (s, 3H), 3.05 (m, 1H), 2.70 (s, 3H), 2.65 (d, J=6.2 Hz, 1H), 2.53 (m, 3H), 1.63 (m, 6H), 1.28 (m, 4H), 1.15 (t, J=7.1 Hz, 3H). MS (M⁺+H) 491.2.

3(R)- and 3(S)-9-[6-(4-Methoxy-benzylamino)-pyridin-2-yl]-3-(2-methoxy-pyrimidin-5-yl)-nonanoic acid ethyl ester (16-11)

¹H NMR (400 MHz, CDCl₃) 8.34 (s, 2H), 7.29 (m, 3H), 6.86 (m, 2H), 6.42 (d, J=7.4 Hz, 1H), 6.19 (d, J=8.2 Hz, 1H), 5.00 (br s, 1H), 4.37 (d, J=5.6 Hz, 2H), 4.04 (q, J=7.1 Hz, 2H), 3.99 (s, 3H), 3.79 (s, 3H), 3.03 (m, 1H), 2.57 (m, 4H), 1.63 (m, 6H), 1.28 (m, 4H), 1.16 (t, J=7.1 Hz, 3H). MS (M⁺+H) 507.2.

3(R)- and 3(S)-3-(2-Ethoxy-pyrimidin-5-yl)-9-[6-(4-methoxy-benzylamino)-pyridin-2-yl]-nonanoic acid ethyl ester(16-12)

¹H NMR (400 MHz, CDCl₃) 8.32 (s, 2H), 7.29 (m, 3H), 6.86 (m, 2H), 6.42 (d, J=7.1 Hz, 1H), 6.19 (d, J=8.3 Hz, 1H), 5.06 (br s, 1H), 4.39 (m, 4H), 4.04 (q, J=7.1 Hz, 2H), 3.79 (s, 3H), 3.02 (m, 1H), 2.58 (m, 4H), 1.64 (m, 6H), 1.42 (t, J=7.1 Hz, 3H), 1.28 (m, 4H), 1.16 (t, J=7.2 Hz, 3H). MS (M⁺+H) 521.2.

Step E: 3(R)- and 3(S)-9-16-[(4-Methoxy-benzyl)-methyl-amino]-pyridin-2-yl}-3-(2-methyl-pyrimidin-5-yl)-nonanoic acid ethyl ester (16-13)

To a solution of 16-10 (0.222 g, 0.452 mmol) in methanol (5 mL) was added paraformaldehyde (0.10 g) and acetic acid (0.129 mL, 2.26 mmol). After stirring at 50° C. for 15 minutes, NaCNBH₃ (0.0369 g, 0.558 mmol) was added. After stirring 2 hours the solution was concentrated in vacuo. The residue was dissolved in CHCl₃ (125 mL) and washed with saturated NaHCO₃, dried, and concentrated to afford 16-13 (0.231 g).

¹H NMR (400 MHz, CDCl₃) 8.46 (s, 2H), 7.32 (t, J=7.8 Hz, 1H), 7.16 (d, J=8.7 Hz, 2H), 6.82 (d, J=8.7 Hz, 2H), 6.37 (d, J=7.2 Hz, 1H), 6.29 (d, J=8.3 Hz, 1H), 4.75 (s, 2H), 4.03 (q, J=7.1 Hz, 2H), 3.78 (s, 3H), 3.05 (m, 1H), 2.98 (s, 3H), 2.70 (s, 3H), 2.66 (m, 1H), 2.56 (m, 3H), 1.67 (m, 6H), 1.26 (m, 4H), 1.15 (t, J=7.1 Hz, 3H). MS (M⁺+H) 505.1.

3(R)- and 3(S)-9-{6-[(4-Methoxy-benzyl)-methyl-amino]-pyridin-2-yl}-3-(2-methoxy-pyrimidin-5-yl)-nonanoic acid ethyl ester (16-14)

¹H NMR (400 MHz, CDCl₃) 8.33 (s, 2H), 7.32 (t, J=7.8 Hz, 1H), 7.17 (d, J=8.8 Hz, 2H), 6.83 (d, J=8.8 Hz, 2H), 6.37 (d, J=7.3 Hz, 1H), 6.29 (d, J=8.5 Hz, 1H), 4.75 (s, 2H), 4.03 (q, J=7.1 Hz, 2H), 3.99 (s, 3H), 3.78 (s, 3H), 3.03 (m, 1H), 2.98 (s, 3H), 2.57 (m, 4H), 1.63 (m, 6H), 1.27 (m, 4H), 1.16 (t, J=7.1 Hz, 3H). MS (M⁺+H) 521.2.

3(R)- and 3(S)-3-(2-Ethoxy-pyrimidin-5-yl)-9-{6-[(4-methoxy-benzyl)-methyl-amino]-pyridin-2-yl}-nonanoic acid ethyl ester (16-15)

¹H NMR (400 MHz, CDCl₃) 8.31 (s, 2H), 7.32 (t, J=7.2 Hz, 1H), 7.16 (d, J=8.7 Hz, 2H), 6.82 (d, J=8.7 Hz, 2H), 6.37 (d, J=7.1 Hz, 1H), 6.29 (d, J=8.3 Hz, 1H), 4.75 (s, 2H), 4.39 (q, J=7.0 Hz, 2H), 4.03 (q, J=7.1 Hz, 2H), 3.78 (s, 3H), 3.02 (m, 1H), 2.98 (s, 3H), 2.58 (m, 4H), 1.65 (m, 6H), 1.42 (t, J=7.1 Hz, 3H), 1.27 (m, 4H), 1.15 (t, J=7.1 Hz, 3H). MS (M⁺+H) 535.1.

Step F: 3(R)- and 3(S)-9-(6-Methylamino-pyridin-2-yl)-3-(2-methyl-pyrimidin-5-yl)-nonanoic acid (16-16)

A solution of 16-13 (0.230 g, 1.83 mmol) in trifluoroacetic acid (5 mL) was stirred at 60° C. for 15 minutes. The solvent was evaporated and the residue was azeotroped (2×25 ml toluene). To a crude solution in dioxane (5 mL) was added NaOH (0.683 mL of 1N solution in water, 0.683 mmol). After stirring at 50° C. for 30 minutes, the mixture was neutralized with HCl (0.683 mL of 1N solution in water, 0.683 mmol) and the solvents were evaporated. The residue chromatographed on silica gel (90:5:5 CHCl₃:EtOAc:MeOH) to give 16-16 (0.125 g, 77% for 3 steps) as a white solid.

¹H NMR (400 MHz, CDCl₃) 8.52 (s, 2H), 7.61 (t, J=8.0 Hz, 1H), 6.42 (d, J=8.5 Hz, 2H), 3.80 (br s, 1H), 3.32 (m, 1H), 2.85 (m, 4H), 2.71 (s, 3H), 2.62 (m, 3H), 1.69 (m, 5H), 1.30 (m, 6H). MS (M⁺+H) 357.1.

3(R)- and 3(S)-3-(2-Methoxy-pyrimidin-5-yl)-9-(6-methylamino-pyridin-2-yl)-nonanoic acid (16-17)

¹H NMR (400 MHz, CDCl₃) 8.40 (s, 2H), 7.60 (t, J=8.1 Hz, 1H), 6.41 (d, J=8.6 Hz, 2H), 4.60 (br s, 1H), 4.00 (s, 3H), 3.29 (m, 1H), 2.85 (m, 4H), 2.63 (m, 1H), 2.55 (m, 2H), 1.86 (m, 1H), 1.68 (m, 3H), 1.59 (m, 1H), 1.26 (m, 6H). MS (M$^+$+H) 373.1.

3(R)- and 3(S)-3-(2-Ethoxy-pyrimidin-5-yl)-9-(6-methylamino-pyridin-2-yl)-nonanoic acid (16-18)

$^1$H NMR (400 MHz, CDCl$_3$) 9.18 (br s, 1H), 8.48 (s, 2H), 7.74 (t, J=8.1 Hz, 1H), 6.57 (d, J=8.8 Hz, 1H), 6.51 (d, J=7.3 Hz, 1H), 4.48 (q, J=7.1 Hz, 2H), 3.09 (m, 1H), 2.98 (s, 3H), 2.73 (m, 3H), 2.60 (m, 1H), 1.66 (m, 4H), 1.44 (t, J=7.0 Hz, 3H), 1.25 (m, 7H). MS (M$^+$+H) 387.2.

To a solution of 16-10 (0.266 g, 0.542 mmol) in EtOH (5 mL) was added acetaldehyde (1.0 mL) and acetic acid (0.155 mL, 2.71 mmol). After stirring at 50° C. for 15 minutes, NaCNBH$_3$ (0.0442 g, 0.704 mmol) was added and the mixture stirred for an additional hour. The reaction was >50% complete, additional acetaldehyde (1.0 mL) and NaCNBH$_3$ (0.0442 g, 0.704 mmol) was added. After stirring 2 hours the solution was concentrated in vacuo. The residue was dissolved in CHCl$_3$ (125 mL) and washed with saturated NaHCO$_3$, dried, and concentrated to afford 17-1 (0.293 g).

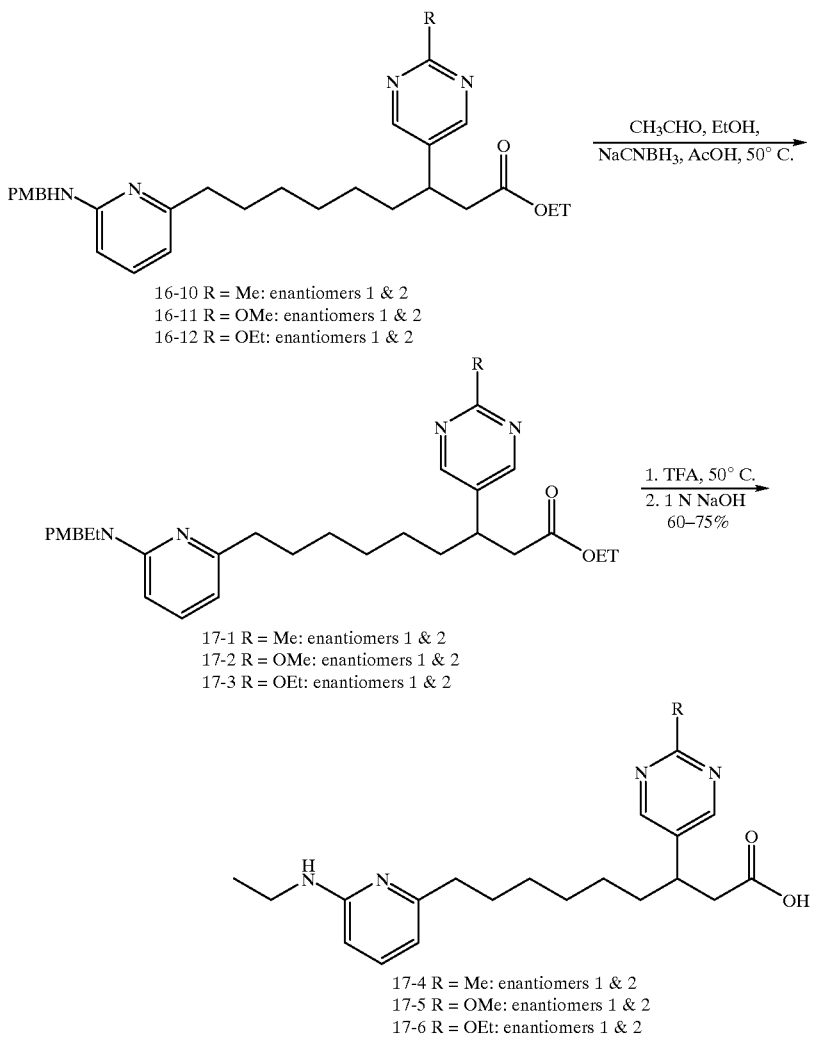

SCHEME 17

EXAMPLES 18–20

3(R)- and 3(S)-9-(6-Ethylamino-pyridin-2-yl)-3-(2-methyl-pyrimidin-5-yl)-nonanoic acid (17-4); 3(R)- and 3(S)-3-(2-Methoxy-pyrimidin-5-yl)-9-(6-ethylamino-pyridin-2-yl)-nonanoic acid (17-5); and 3(R)- and 3(S)-3-(2-Ethoxy-pyrimidin-5-yl)-9-(6-ethylamino-pyridin-2-yl)-nonanoic acid (17-6)

Step A: 3(R)- and 3(S)-9-{6-[Ethyl-(4-methoxy-benzyl)-amino]-pyridin-2-yl}-3-(2-methyl-pyrimidin-5-yl)-nonanoic acid ethyl ester (17-1)

$^1$H NMR (400 MHz, CDCl$_3$) 8.46 (s, 2H), 7.27 (m, 1H), 7.18 (d, J=8.3 Hz, 2H), 6.82 (d, J=8.6 Hz, 2H), 6.33 (d, J=7.2 Hz, 1H), 6.25 (d, J=8.4 Hz, 1H), 4.68 (s, 2H), 4.04 (q, J=7.1 Hz, 2H), 3.78 (s, 3H), 3.50 (q, J=7.0 Hz, 2H), 3.04 (m, 1H), 2.70 (s, 3H), 2.66 (m, 1H), 2.55 (m, 3H), 1.58 (m, 6H), 1.32 (m, 4H), 1.15 (t, J=7.1 Hz, 3H), 1.12 (t, J=7.0 Hz, 3H). MS (M$^+$+H) 519.2.

3(R)- and 3(S)-9-{6-[Ethyl-(4-methoxy-benzyl)-amino]-pyridin-2-yl}-3-(2-methoxy-pyrimidin-5-yl)-nonanoic acid ethyl ester (17-2)

MS (M$^+$+H) 535.1

3(R)- and 3(S)-3-(2-Ethoxy-pyrimidin-5-yl)-9-{6-[ethyl-(4-methoxy-benzyl)-amino]-pyridin-2-yl}-nonanoic acid ethyl ester (17-3)

$^1$H NMR (400 MHz, CDCl$_3$) 8.32 (s, 2H), 7.28 (m, 1H), 7.18 (d, J=8.8 Hz, 2H), 6.82 (d, J=8.7 Hz, 2H), 6.34 (d, J=7.1 Hz, 1H), 6.24 (d, J=8.4 Hz, 1H), 4.68 (s, 2H), 4.39 (q, J=7.1 Hz, 2H), 4.03 (q, J=7.1 Hz, 2H), 3.78 (s, 3H), 3.51 (q, J=7.0 Hz, 2H), 3.02 (m, 1H), 2.57 (m, 4H), 1.61 (m, 6H), 1.34 (m, 7H), 1.16 (m, 6H). MS (M$^+$+H) 549.2.

Step B: 3(R)- and 3(S)-9-(6-Ethylamino-pyridin-2-yl)-3-(2-methyl-pyrimidin-5-yl)-nonanoic acid (17-4)

A solution of 17-1 (0.293 g, 0.564 mmol) in trifluoroacetic acid (3 mL) was stirred at 60° C. for 15 minutes. The solvent was evaporated and the residue was azeotroped (2×25 ml toluene). The crude solution in dioxane (5 mL) was added NaOH (0.847 mL of 1N solution in water, 0.847 mmol). After 30 minutes, the mixture was neutralized with HCl (0.847 mL of 1N solution in water, 0.847 mmol) and the solvents were evaporated. The residue chromatographed on silica gel (90:5:5 CHCl$_3$:EtOAc:MeOH) to give 17-4 (0.150 g, 75% for 3 steps) as a white solid.

$^1$H NMR (400 MHz, CDCl$_3$) 8.51 (s, 2H), 7.57 (m, 1H), 6.43 (d, J=8.9 Hz, 1H), 6.40 (d, J=7.2 Hz, 1H), 3.80 (br s, 1H), 3.30 (m, 1H), 3.23 (q, J=7.2 Hz, 2H), 2.86 (m, 1H), 2.70 (s, 3H), 2.58 (m, 3H), 1.85 (m, 1H), 1.62 (m, 4H), 1.32 (m, 9H). MS (M$^+$+H) 371.2.

3(R)- and 3(S)-3-(2-Methoxy-pyrimidin-5-yl)-9-(6-ethylamino-pyridin-2-yl)-nonanoic acid (17-5)

$^1$H NMR (400 MHz, CDCl$_3$) 8.39 (s, 2H), 7.60 (t, J=8.1 Hz, 1H), 6.44 (d, J=9.2 Hz, 1H), 6.41 (d, J=7.1 Hz, 1H), 3.99 (s, 3H), 3.25 (m, 4H), 2.85 (m, 1H), 2.63 (m, 1H), 2.57 (d, J=6.8 Hz, 2H), 1.84 (m, 1H), 1.67 (m, 3H), 1.59 (m, 1H), 1.33 (m, 9H). MS (M$^+$+1H)373.1.

3(R)- and 3(S)-3-(2-Ethoxy-pyrimidin-5-yl)-9-(6-ethylamino-pyridin-2-yl)-nonanoic acid (17-6)

$^1$H NMR (400 MHz, CDCl$_3$) 8.36 (s, 2H), 7.62 (t, J=8.0 Hz, 1H), 6.47 (d, J=9.0 Hz, 1H), 6.42 (d, J=7.2 Hz, 1H), 4.39 (q, J=7.1 Hz, 2H), 3.26 (q, J=7.2 Hz, 2H), 3.17 (m, 1H), 2.77 (m, 1H), 2.61 (m, 3H), 1.77 (m, 1H), 1.67 (m, 2H), 1.56 (m, 2H), 1.42 (t, J=7.1 Hz, 3H), 1.32 (t, J=7.2 Hz, 3H), 1.26 (m, 6H). MS (M$^+$+H) 401.2.

SCHEME 18

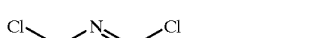
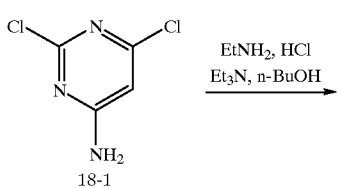

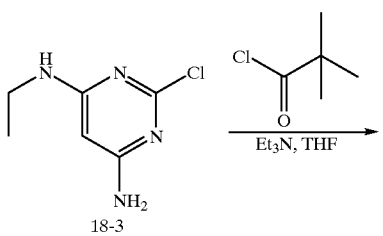

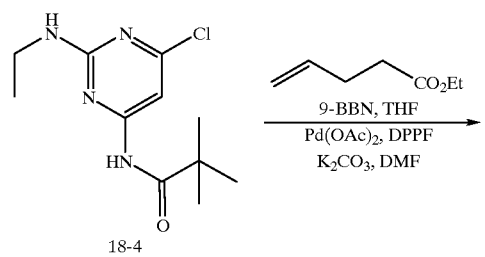

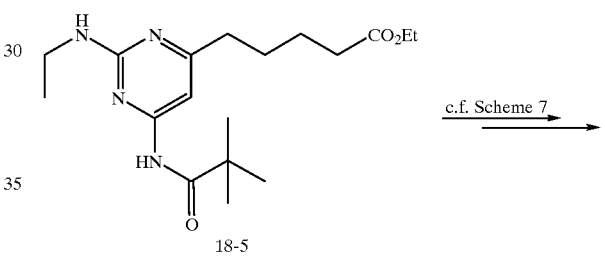

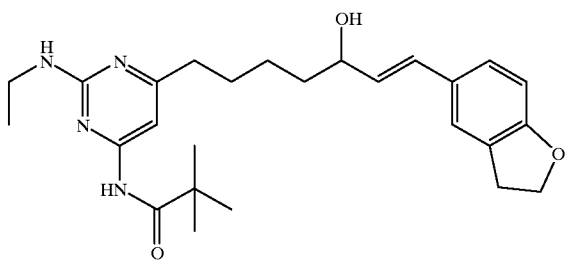

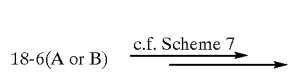

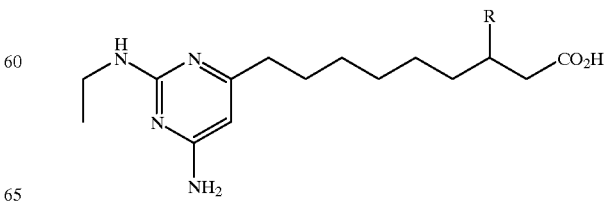

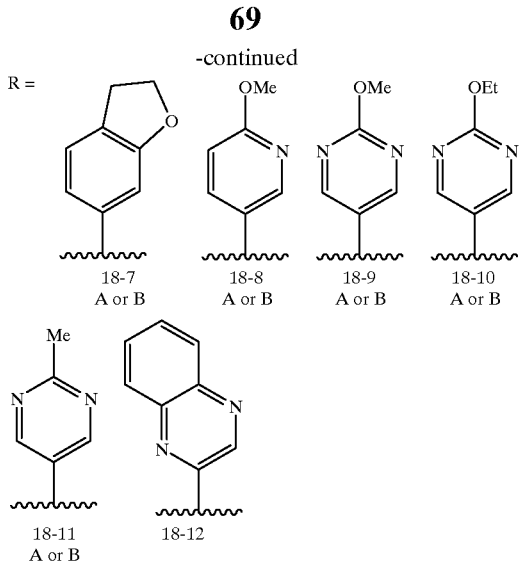

EXAMPLE 21

9-(4-Amino-2-ethylaminopyrimidin-6-yl)-3-(dihydrobenzofuran-6-yl)-nonanoic acid (18-7 Enantiomer A and Enantiomer B)

Step A: 4-Amino-6-chloro-2-ethylaminopyrimidine (18-2)

A mixture of 2,6-dichloro-4-aminopyrimidine 18-1 (Avocado; 4.8 g, 29.3 mmol), ethylamine hydrochloride (7.0 g, 85.8 mmol), Et$_3$N (20 mL, 144 mmol) and n-butanol (150 mL) was heated to 90° C. for 6 hours. After cooling, the solvent was removed in vacuo and the residue partitioned between saturated Na$_2$CO$_3$ solution and EtOAc. The EtOAc layer was washed with brine, dried (MgSO$_4$) and concentrated to give an orange solid. Purification by column chromatography (EtOAc/hexane 1:1) gave the title compound 18-2 as a white solid.

$^1$H NMR (400 MHz, CDCl$_3$): 5.78 (1H, s), 5.03 (1H, br s), 4.75 (2H, br s), 3.37 (2H, quintet), 1.18 (3H, t).

Further elution provided the minor isomer 4-aminoethyl-2-chloro-6-aminopyrimidine 18-3 as a solid.

$^1$H NMR (400 MHz, CDCl$_3$): 5.25 (1H, s), 5.14 (1H, br s), 4.98 (2H, br s), 3.20 (2H, quintet), 1.23 (3H, t).

Step B: 4-Pivaloylamino-6-chloro-2-ethylaminopyrimidine (18-4)

A mixture of the pyrimidine 18-2 (3.76 g, 21.8 mmol), pivaloyl chloride (10.7 mL, 87 mmol), Et$_3$N (15.2 mL, 109 mmol) and TEF (80 mL) were stirred at room temperature for 24 hours. A further 3 mL of pivaloyl chloride and 4 mL of Et$_3$N was added and the mixture stirred for another 24 hours. The solution was poured into saturated Na$_2$CO$_3$, extracted with EtOAc (2×), washed with brine, dried (MgSO$_4$) and filtered through a pad of silica gel. Removal of the solvent afforded an orange solid. Trituration with ether/hexane ~20:1 and filtration provided the title compound 18-4 as a white solid.

$^1$H NMR (400 MHz, CDCl$_3$): 7.77 (1H, br s), 7.5 (1H, s), 5.06 (1H, br s), 3.40 (2H, quintet), 1.30 (9H, s), 1.20 (3H, t).

Step C: 5-(2-ethylamino-4-pivaloylaminopyrimidin-6-yl)pentanoic acid ethyl ester (18-5)

Following the procedure described for Example 7, compound 7-3, but using 18-4 as starting material, the title compound 18-5 was prepared as an oil.

$^1$H NMR (600 MHz, CDCl$_3$): 7.77 (1H, br s), 7.33 (1H, s), 4.90 (1H, br s), 4.12 (2H, quintet), 3.39 (2H, quintet), 2.55 (2H, t), 2.32 (2H, t), 1.71 (4H, m), 1.30 (9H, s), 1.25 (2H, t), 1.20 (3H, t).

Step D: 9-(2-Ethylamino-4-pivaloylaminopyrimidin-6-yl)-1-(benzofuran-6-yl)hept-1-ene-3-ol (18-6 racemate, enantiomer A and enantiomer B)

Following the procedure described for Example 7, compound 7-6, but using 18-5 and benzofuran-6-carbaldehyde (for preparation, see U.S. Pat. No. 6,048,861, which is incorporated by reference herein in its entirety) as starting material, the title compound 18-6 was prepared as an oil. Separation of the enantiomers was achieved by chiral phase EPLC (Chiralcel AD column; hexane (0.1% diethylamine)/EtOH 30:70) to give both 18-6A enantiomer A and 18-6B enantiomer B as oils. Each was used without purification in the next step.

Step E: 9-(4-Amino-2-ethylaminopyrimidin-6-yl)-3-(dihydrobenzofuran-6-yl)nonanoic acid (18-7A Enantiomer A)

Following the procedure described for Example 7, compound 7-9, but using 18-6A enantiomer A as starting material, the title compound 18-7A enantiomer A (TFA salt) was prepared as a white solid.

$^1$H NMR (500 MHz, CD$_3$OD): 7.08 (1H, dd), 6.65 (1H, dd), 6.57 (1H, s), 5.87 (1H, s), 4.50 (2H, t), 3.43 (2H, q), 3.12 (2H, t), 2.96 (1H, m), 2.56 (1H, dd), 2.48 (3H, m), 1.6 (4H, m), 1.30 (4H, m), 1.2 (5H, m). Mass spectrum: found (M+H)$^+$=413.2

Step F: 9-(4-Amino-2-ethylaminopyrimidin-6-yl)-3-(dihydrobenzofuran-6-yl)nonanoic acid (18-7B Enantiomer B)

$^1$H NMR identical to that for 18-7A enantiomer A. Mass spectrum: found (M+H)$^+$=413.2

EXAMPLE 22

9-(4-Amino-2-ethylaminopyrimidin-6-yl)-3-(6-methoxypyridin-3-yl)nonanoic acid (18-8A Enantiomer A)

Following the procedure described for Example 21, compound 18-7A enantiomer A, but using 6-methoxypyridine-3-carbaldehyde as starting material, the title compound 18-8A enantiomer A (TFA salt) was prepared as a white solid.

$^1$H NMR (400 MHz, CD$_3$OD): 7.98 (1H, s), 7.69 (1H, dd), 6.87 (1H, dd), 5.87 (1H, s), 4.84 (3H, s), 3.44 (2H, q), 3.05 (1H, m), 2.65 (1H, dd), 2.5 (3H, m), 1.7 (1H, m), 1.6 (3H, m), 1.3 (4H, m), 1.2 (5H, m). Mass spectrum: found (M+H)$^+$=402.2

9-(4-Amino-2-ethylaminopyrimidin-6-yl)-3-(6-methoxypyridin-3-yl)nonanoic acid (18-8B Enantiomer B)

Following the procedure described for Example 21, compound 18-7B enantiomer B, but using 6-methoxypyridine-3-carbaldehyde as starting material, the title compound 18-8B enantiomer B (TFA salt) was prepared as a white solid.

$^1$H NMR identical to that for 18-8A enantiomer A. Mass spectrum: found (M+H)$^+$=402.2

EXAMPLE 23

9-(4-Amino-2-ethylaminopyrimidin-6-yl)-3-(2-methoxypyridin-5-yl)nonanoic acid (18-9A Enantiomer A)

Following the procedure described for Example 21, compound 18-7A enantiomer A, but using 2-methoxypyrimidine-5-carbaldehyde as starting material, the title compound 18-9A enantiomer A (TFA salt) was prepared as a white solid.

$^{1}$H NMR (400 MHz, CD$_{3}$OD): 8.45 (2H, s), 5.87 (1H, s), 3.98 (3H, s), 3.45 (2H, q), 3.06 (1H, m), 2.72 (1H, dd), 2.58 (1H, dd), 2.49 (2H, t), 1.7 (1H, m), 1.6 (3H, m), 1.3 (4H, m), 1.2 (5H, m). Mass spectrum: found (M+H)$^{+}$=403.1

9-(4-Amino-2-ethylaminopyrimidin-6-yl)-3-(2-methoxypyrimidin-5-yl)nonanoic acid (18-9B Enantiomer B)

Following the procedure described for Example 21, compound 18-7B enantiomer B, but using 2-methoxypyrimidine-5-carbaldehyde as starting material, the title compound 18-9B enantiomer B (TFA salt) was prepared as a white solid.

$^{1}$H NMR identical to that for 18-9A enantiomer A Mass spectrum: found (M+H)$^{+}$=403.1

EXAMPLE 24

9-(4-Amino-2-ethylaminopyrimidin-6-yl)-3-(2-ethoxypyrimidin-5-yl)nonanoic acid (18-10A Enantiomer A)

Following the procedure described for Example 21, compound 18-7A enantiomer A, but using 2-ethoxypyrimidine-5-carbaldehyde as starting material, the title compound 18-10A enantiomer A (TFA salt) was prepared as a white solid.

$^{1}$H NMR (400 MHz, CD$_{3}$OD): 8.42 (2H, s), 5.85 (1H, s), 4.38 (2H, q), 3.41 (2H, q), 3.03 (1H, m), 2.70 (1H, dd), 2.55 (1H, dd), 2.46 (2H, t), 1.7 (1H, m), 1.6 (3H, m), 1.1–1.4 (12H, m). Mass spectrum: found (M+H)$^{+}$=417.2

9-(4-Amino-2-ethylaminopyrimidin-6-yl)-3-(2-ethoxypyrimidin-5-yl)nonanoic acid (18-10B Enantiomer B)

Following the procedure described for Example 21, compound 18-7B enantiomer B, but using 2-ethoxypyrimidine-5-carbaldehyde as starting material, the title compound 18-10B enantiomer B (TFA salt) was prepared as a white solid.

$^{1}$H NMR identical to that for 18-10A enantiomer A Mass spectrum: found (M+H)$^{+}$=417.2

EXAMPLE 25

9-(4-Amino-2-ethylaminopyrimidin-6-yl)-3-(2-methylpyrimidin-5-yl)nonanoic acid (18-11A Enantiomer A)

Following the procedure described for Example 21, compound 18-7A enantiomer A, but using 2-methylpyrimidine-5-carbaldehyde as starting material, the title compound 18-11A enantiomer A (TFA salt) was prepared as a white solid.

$^{1}$H NMR (400 MHz, CD$_{3}$OD): 8.61 (2H, s), 5.87 (1H, s), 3.44 (2H, q), 3.10 (1H, m), 2.75 (1H, dd), 2.67 (3H, s), 2.63 (1H, dd), 2.49 (2H, t), 1.75 (1H, m), 1.68 (1H, m), 1.6 (2H, m), 1.35 (4H, m), 1.21 (3H, t), 1.2 (2H, m). Mass spectrum: found (M+H)$^{+}$=387.2

9-(4-Amino-2-ethylaminopyrimidin-6-yl)-3-(2-methylpyrimidin-5-yl)nonanoic acid (18-11B Enantiomer B)

Following the procedure described for Example 21, compound 18-7B enantiomer B, but using 2-methylpyrimidine-5-carbaldehyde as starting material, the title compound 18-11B enantiomer B (TFA salt) was prepared as a white solid.

1H NMR identical to that for 18-11A enantiomer A

Mass spectrum: found (M+H)$^{+}$=387.2

EXAMPLE 26

9-(4-Amino-2-ethylaminopyrimidin-6-yl)-3-(quinoxalin-2-yl)nonanoic acid (18-12)

Following the procedure described for Example 21, compound 18-7, but using quinoxalin-2-carbaldehyde 14-1 as starting material, the title compound 18-12 racemate (TFA salt) was prepared as a white solid.

$^{1}$H NMR (500 MHz, CD$_{3}$OD): 8.83 (1H, s), 8.07 (2H, m), 7.82 (2H, m), 5.86 (1H, s), 3.66 (1H, m), 3.44 (2H, q), 3.05 (1H, dd), 2.82 (1H, dd), 2.46 (2H, t), 1.9 (1H, m), 1.82 (1H, m), 1.58 (2H, m), 1.35 (4H, m), 1.2 (5H, m). Mass spectrum: found (M+H)$^{+}$=423.2

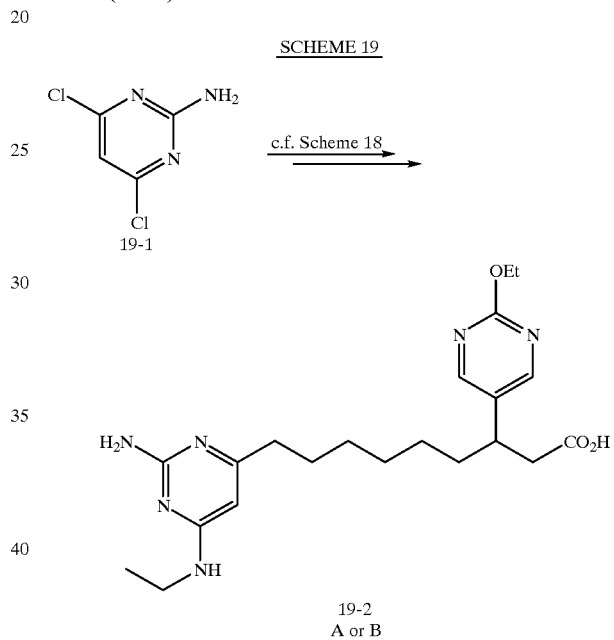

SCHEME 19

EXAMPLE 27

9-(2-Amino-4-ethylaminopyrimidin-6-yl)-3-(2-ethoxypyrimidin-5-yl)nonanoic acid (19-2A Enantiomer A)

Following the procedure described for Example 21, compound 18-7A enantiomer A, but using 2-amino-4,6-dichloropyrimidine (19-1; Aldrich) and 2-ethoxypyrimidine-5-carbaldehyde as starting materials, the title compound 19-2A enantiomer A (TFA salt) was prepared as a white solid.

$^{1}$H NMR (400 MHz, CD$_{3}$OD): 8.41 (2H, s), 5.82 (1H, s), 4.38 (2H, q), 3.44 (2H, q), 3.03 (1H, m), 2.70 (1H, dd), 2.55 (1H, dd), 2.46 (2H, t), 1.7 (1H, m), 1.6 (3H, m), 1.37 (3H, t), 1.1–1.35 (6H, m), 1.18 (3H, t). Mass spectrum: found (M+H)$^{+}$=417.2

9-(2-Amino-4-ethylaminopyrimidin-6-yl)-3-(2-ethylpyridine-5-yl)nonanoic acid (19-2B Enantiomer B)

Following the procedure described for Example 21, compound 18-7B enantiomer B, but using 19-1 and 2-ethoxypyrimidine-5-carbaldehyde as starting materials, the title compound 19-2B enantiomer B (TFA salt) was prepared as a white solid.

1H NMR identical to that for 19-2A enantiomer A Mass spectrum: found (M+H)+=417.

Following the procedure described for Example 7, compound 7-9, but using 20-1B as starting material, the title compound 20-2B enantiomer B (TFA salt) was prepared as a white solid.

$^1$H NMR identical to that for 20-2A enantiomer A Mass spectrum: found (M+H)+=359.2

SCHEME 20

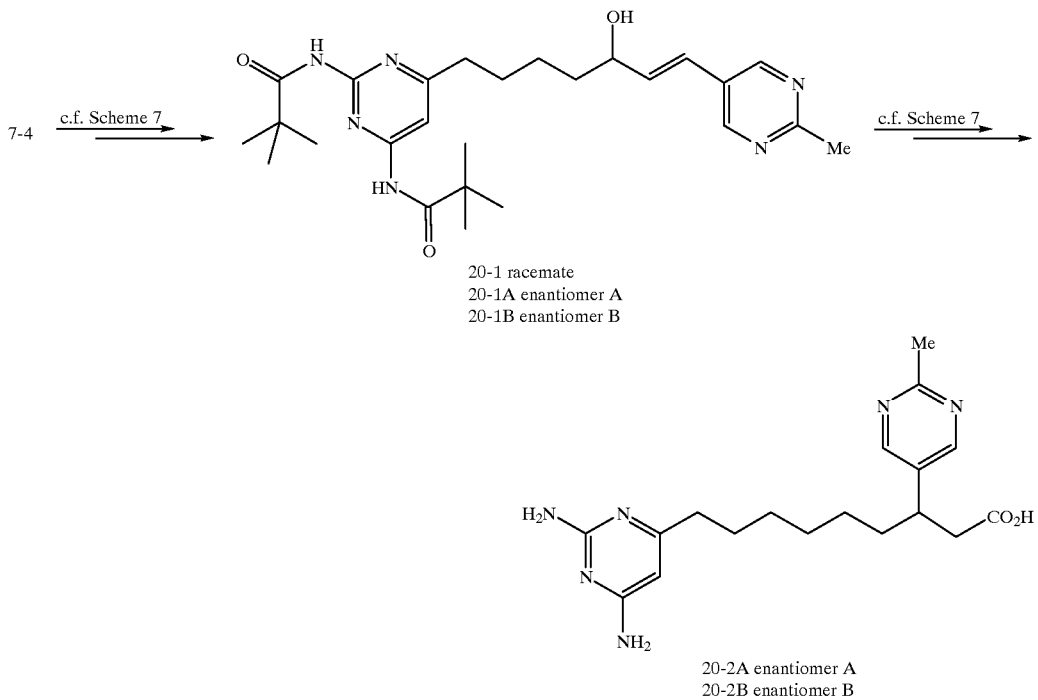

20-1 racemate
20-1A enantiomer A
20-1B enantiomer B 20-2A enantiomer A
20-2B enantiomer B

EXAMPLE 28

9-(4-Amino-2-aminopyrimidin-6-yl)-3-(2-methylpyrimidin-5-yl)nonanoic acid (20-2 Enantiomer A and Enantiomer B)

Step A: 7-(2,4-Dipivaloylaminopyrimidin-6-yl)-1-(2-methylpyrimidin-5-yl)-3-hydroxy-hept-1-ene (20-1 racemate, enantiomer A and enantiomer B)

Following the procedure described for Example 7, compound 7-6, but using 2-methylpyrimidine-5-carbaldehyde, the title compound 20-1 was prepared as a yellow foam. Preparative HPLC separation using Chiralpak AS column (eluting with 70:30 hexane:isopropyl alcohol containing 0.1% diethyl amine) afforded the faster eluting enantiomer 20-1A (enantiomer A) followed by the slower eluting enantiomer 20-1B (enantiomer B).

Step B: 9-(4-Amino-2-aminopyrimidin-6-yl)-3-(2-methylpyrimidin-5-yl)nonanoic acid (20-2A Enantiomer A)

Following the procedure described for Example 7, compound 7-9, but using 20-1A as starting material, the title compound 20-2A enantiomer A (TFA salt) was prepared as a white solid.

$^1$H NMR (400 MHz, CD$_3$OD): 8.64 (2H, s), 5.88 (1H, s), 3.10 (1H, m), 2.74 (1H, dd), 2.66 (3H, s), 2.61 (1H, dd), 2.47 (2H, t), 1.5–1.8 (4H, m), 1.1–1.4 (5H, m). Mass spectrum: found (M+H)+=359.2

Step C: 9-(4-Amino-2-aminopyrimidin-6-yl)-3-(2-methylpyrimidin-5-yl)nonanoic acid (20-2B Enantiomer B)

SCHEME 21

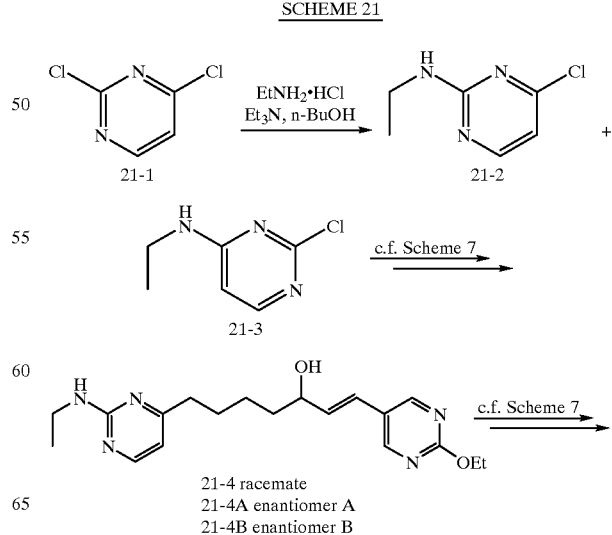

21-4 racemate
21-4A enantiomer A
21-4B enantiomer B

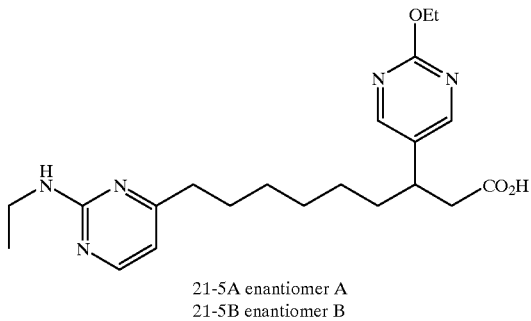

21-5A enantiomer A
21-5B enantiomer B

EXAMPLE 29

9-(2-Ethylaminopyrimidin-6-yl)-3-(2-ethoxypyrimidin-5-yl)nonanoic acid (21-5 Enantiomer A and Enantiomer B)

Step A: 4-Chloro-2-ethylaminopyrimidine (21-2)

A mixture of 2,4-dichloropyrimidine 21-1 (7.0 g, 47 mmol), ethylamine hydrochloride (5.75 g, 70.5 mmol), triethylamine (19.6 mL, 141 mmol) and n-butanol (150 mL) was heated at 90° C. for 6 hours. The solution was cooled, poured into water and extracted with EtOAc (2×). After washing with water then brine, the organic layer was dried (MgSO$_4$) and concentrated to give an oil. Column chromatography (hexane:EtOAc 2:1 then 1:1) afforded the title compound 21-2 as the minor compound.

$^1$H NMR (400 MHz, CDCl$_3$): 8.14 (1H, dd), 6.54 (1H, dd), 5.29 (1H, br s), 3.45 (2H, quintet), 1.23 (3H, t).

Further elution then afforded the isomeric compound 21-3 as the major compound.

Step B: 7-(2-Ethylaminopyrimidin-6-yl)-1-(2-ethoxypyrimidin-5-yl)-3-hydroxy-hept-1-ene (21-4 racemate, enantiomer A and enantiomer B)

Following the procedure described for Example 7, compound 7-6, but starting with 21-2 and using 2-ethoxypyrimidine-5-carbaldehyde, the title compound 21-4 was prepared as a racemate. Preparative HPLC separation using Chiralcel AD column (eluting with 30:70 hexane (0.1% diethyl amine):ethanol) afforded the faster eluting enantiomer 21-4A (enantiomer A) followed by the slower eluting enantiomer 21-4B (enantiomer B).

9-(2-Ethylaminopyrimidin-6-yl)-3-(2-ethoxypyrimidin-5-yl)nonanoic acid (21-5A Enantiomer A)

Following the procedure described for Example 7, compound 7-9, but using 21-4A as starting material, the title compound 21-5A enantiomer A (TFA salt) was prepared as a white solid.

$^1$H NMR (400 MHz, CDCl$_3$): 9.52 (1H, br s), 8.47 (2H, s), 7.99 (1H, dd), 6.57 (1H, br s), 4.46 (2H, q), 3.57 (2H, m), 3.08 (1H, m), 2.75 (3H, m), 2.58 (1H, dd), 1.55–1.8 (4H, m) 1.43 (3H, t), 1.1–1.4 (9H, m). Mass spectrum: found (M+H)$^+$=402.2

9-(2-Ethylaminopyrimidin-6-yl)-3-(2-ethoxypyrimidin-5-yl)nonanoic acid (21-5B Enantiomer B)

Following the procedure described for Example 7, compound 7-9, but using 21-4B as starting material, the title compound 21-5B enantiomer B (TFA salt) was prepared as a white solid.

1H NMR identical to that for 21-5A enantiomer A. Mass spectrum: found (M+H)$^+$=402.2

SCHEME 22

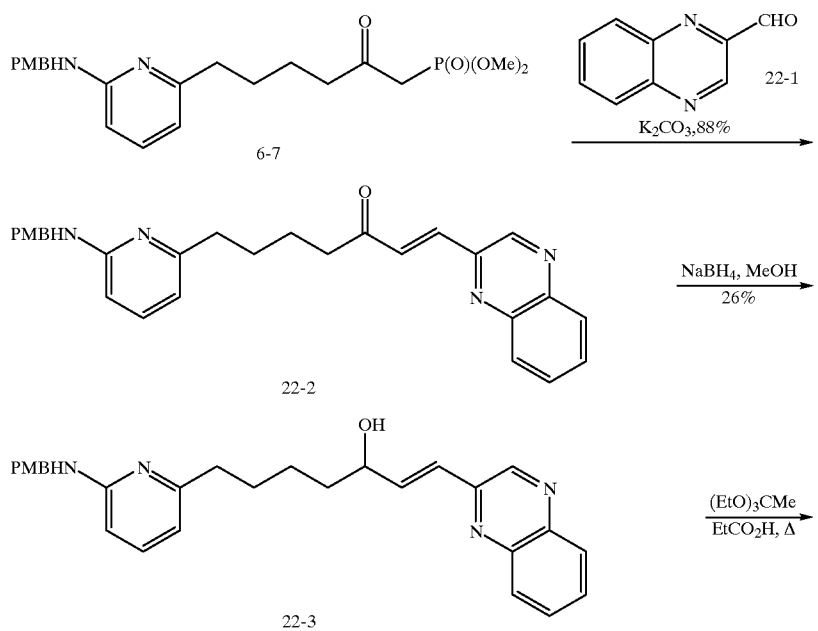

-continued

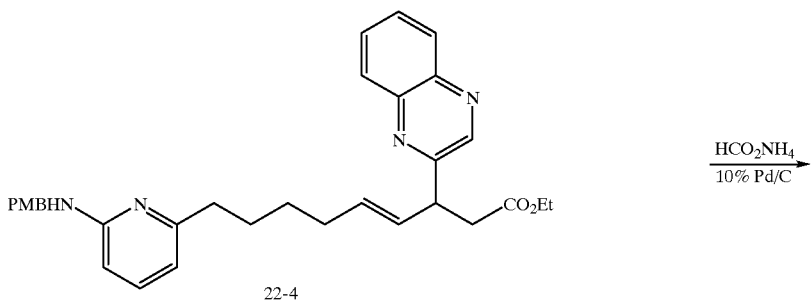
22-4

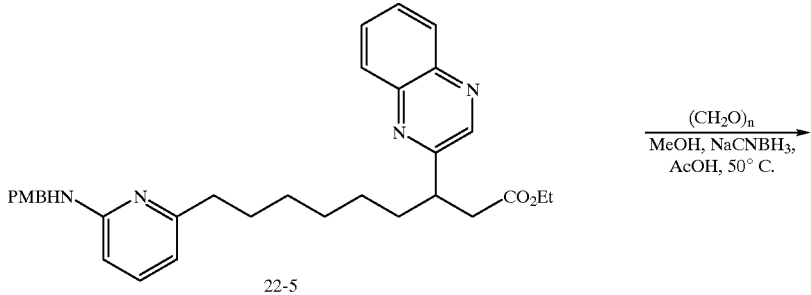
22-5

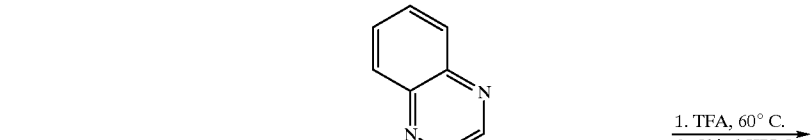
22-6

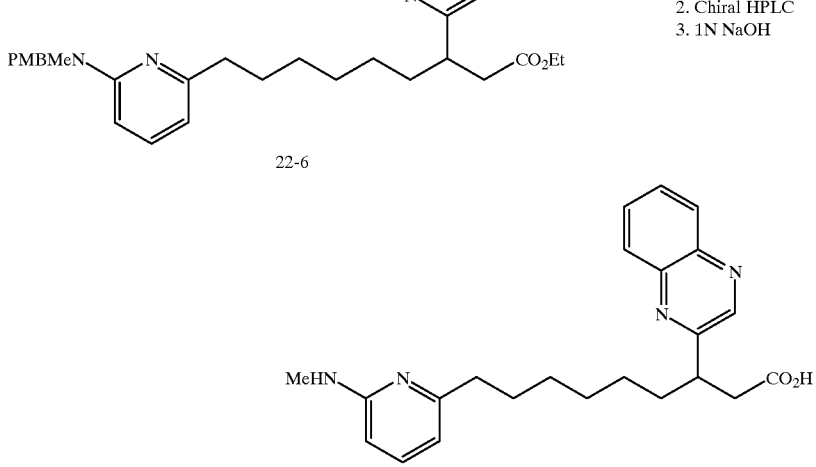
22-7a
22-7b

EXAMPLE 30

Step A: 7-[6-(4-Methoxy-benzylamino)-pyridin-2-yl]-1-quinoxalin-2-yl-hept-1-en-3-one (22-2)

To a solution of 6-7 (12.0 g, 28.5 mmol) and quinoxaline-2-carbaldehyde 22-1 (4.51 g, 28.5 mmol) in THF (250 mL) at 0° C. was added 4M NaOH (7.49 mL, 29.9 mmol) dropwise. After 15 minutes the ice bath was removed and the mixture stirred for an additional 10 minutes. The solution was diluted with water, extracted with ethyl acetate, and dried ($Na_2SO_4$). Following concentration, the residue was triturated with ether to give 11.4 g (88%) of 22-2 as a white solid.

$^1$H NMR (400 MHz, $CDCl_3$): δ9.02 (s, 1H), 8.10 (m, 2H), 7.81 (m, 2H), 7.73 (d, J=16.1 Hz, 1H), 7.38 (d, J=16.1 Hz, 1H), 7.32 (t, J=7.8 Hz, 1H), 7.27 (s, 1H), 6.85 (d, J=8.3 Hz, 2H), 6.47 (d, J=7.3 Hz, 1H), 6.19 (d, J=8.3 Hz, 1H), 4.80 (br s, 1H), 4.38 (d, J=4.6 Hz, 2H), 3.78 (s, 3H), 2.79 (m, 2H), 2.67 (m, 2H), 1.80 (m, 4H). MS: ($M^+$+H) 453.2.

Step B: (±)7-[6-(4-Methoxy-benzylamino)-pyridin-2-yl]-1-quinoxalin-2-yl-hept-1-en-3-ol (22-3)

A solution of the enone 22-2 (1.0 g, 2.2 mmol) in MeOH (50 mL) at 0° C. was treated with $NaBH_4$ (0.092 g, 2.4 mmol). The ice bath was removed and the solution was stirred at room temperature for 1 hr. The reaction was quenched with water (25 mL) and extracted with EtOAc (3×125 mL). The organics were combined, dried ($Na_2SO_4$), concentrated in vacuo, and purified on silica gel (90:5:5 $CHCl_3$:EtOAc:MeOH) to afford 0.26 g of 22-3.

$^1$H NMR (400 MHz, $CDCl_3$): δ8.92 (s, 1H), 8.05 (m, 2H), 7.73 (m, 2H), 7.30 (m, 3H), 6.96 (m, 2H), 6.86 (d, J=8.5 Hz, 2H), 6.45 (m, 2H), 6.19 (d, J=8.3 Hz, 1H), 4.91 (br s, 1H), 4.48 (m, 1H), 4.38 (d, J=5.4 Hz, 2H), 3.79 (s, 3H), 2.64 (m, 2H), 1.63 (m, 7H).

Step C: (±)9-[6-(4-Methoxy-benzylamino)-pyridin-2-yl]-3-quinoxalin-2-yl-non-4-enoic acid ethyl ester (22-4)

A solution of the allylic alcohol 22-3 (0.26 g, 0.57 mmol) in (EtO)$_3$CMe (10 mL) was treated with 100 μL of a 1 mL solution of (EtO)$_3$CMe containing 10 μL of propionic acid. The yellow solution was heated at 150° C. for 90 minutes. The solution was cooled to room temperature and poured into 1N HCl/brine. The mixture was extracted with CHCl$_3$, dried, concentrated, and purified on silica gel (90:5:5 CHCl$_3$:EtOAc:MeOH) to give 0.143 g (48%)of 22-4.

$^1$H NMR (400 MHz, CDCl$_3$): δ8.80 (s, 1H), 8.02 (m, 2H), 7.70 (m, 2H), 7.28 (m, 3H), 6.85 (m, 2H), 6.40 (d, J=7.4 Hz, 1H), 6.16 (d, J=8.2 Hz, 1H), 5.65 (m, 2H), 4.37 (d, J=4.6 Hz, 2H), 4.23 (q, J=6.8 Hz, 1H), 4.07 (q, J=7.2 Hz, 2H), 3.79 (s, 3H), 3.22 (m, 1H), 2.82 (dd, J=8.4 Hz, 1H), 2.57 (t, J=7.7 Hz, 2H), 2.05 (m, 2H), 1.66 (m, 2H), 1.42 (m, 2H). 1.26 (m, 1H), 1.17 (t, J=7.1 Hz, 3H). MS (M$^+$+H) 525.2.

Step D: (±)9-[6-(4-Methoxy-benzylamino)-pyridin-2-yl]-3-quinoxalin-2-yl-nonanoic acid ethyl ester (22-5)

A solution of the 22-4 (0.141 g, 0.268 mmol) in 25 mL absolute EtOH was treated with 10% Pd—C (0.015 g, 10% by wt) at room temperature under an argon atmosphere. Then ammonium formate (0.101 g, 1.61 mmol) was added and the heterogeneous mixture was refluxed for 30 minutes. The reaction was >50% complete (by ms). At this point, more Pd—C (0.008 g, 5% by wt) and NH$_4$CO$_2$ (0.050 g, 0.80 mmol) were added and the mixture refluxed for an additional 30 minutes (reaction complete by ms). The solution was then filtered through a Celite plug, washed with EtOH (75 mL), and concentrated in vacuo to afford 0.130 g 22-5.

$^1$NMR (400 MHz, CDCl$_3$): δ8.74 (s, 1H), 8.02 (m, 2H), 7.71 (m, 2H), 7.28 (m, 3H), 6.86 (m, 2H), 6.40 (d, J=7.0 Hz, 1H), 6.16 (d, J=8.2 Hz, 1H), 4.96 (br s, 1H), 4.36 (d, J=4.7 Hz, 2H), 4.01 (q, J=7.1 Hz, 2H), 3.79 (s, 3H), 3.52 (m, 1H), 3.05 (m, 1H), 2.76 (dd, J=5.4 Hz, 3H), 2.54 (t, J=7.8 Hz, 2H), 1.66 (m, 5H), 1.28 (m, 5H), 1.12 (t, J=7.0 Hz, 3H). MS (M$^+$+H) 527.2.

Step D: (±)9-{6-[(4-Methoxy-benzyl)-methyl-amino]-pyridin-2-yl}-3-quinoxalin-2-yl-nonanoic acid ethyl ester (22-6)

To a solution of 22-5 (0.130 g, 0.246 mmol) in methanol (5 mL) was added paraformaldehyde (0.07 g) and acetic acid (0.071 mL, 1.23 mmol). After stirring at 50° C. for 15 minutes, NaCNBH$_3$ (0.020 g, 0.32 mmol) was added. After stirring 2 hours the solution was concentrated in vacuo. The residue was dissolved in CHCl$_3$ (125 mL) and washed with saturated NaHCO$_3$, dried, and concentrated to afford 22-6 (0.132 g).

$^1$H NMR (400 MHz, CDCl$_3$): δ8.74 (s, 1H), 8.04 (m, 2H), 7.71 (m, 2H), 7.30 (t, J=7.8 Hz, 1H), 7.15 (d, J=8.5 Hz, 2H), 6.82 (d, J=8.5 Hz, 2H), 6.35 (d, J=7.2 Hz, 1H), 6.27 (d, J=8.3 Hz, 1H), 4.75 (m, 2H), 4.01 (q, J=7.1 Hz, 2H), 3.77 (s, 3H), 3.52 (m, 1H), 3.05 (m, 1H), 2.97 (s, 3H), 2.76 (dd, J=5.4 Hz, 1H), 2.56 (t, J=7.6 Hz, 2H), 1.61 (m, 5H), 1.28 (m, 5H), 1.11 (t, J=7.1 Hz, 3H). MS (M$^+$+H) 540.9.

Step E: 3(R)- and 3(S)-9-(6-Methylamino-pyridin-2-yl)-3-quinoxalin-2-yl-nonanoic acid (22-7a and 22-7b)

A solution of 22-6 (0.130 g, 0.24 mmol) in trifluoroacetic acid (2 mL) was stirred at 50° C. for 15 minutes. The solvent was evaporated and the residue was azeotroped (2×25 ml toluene), then resolved on a chiral AD column 1 ml/min 1:1 MeOH:IPA affording 0.041 g of enantiomer 1 and 0.037 g of enantiomer 2 obtained from Prep HPLC. Each enantiomer was hydrolyzed in the following manner. To a crude solution of the enantiomer in dioxane (5 mL) was added NaOH (0.683 mL of 1N solution in water, 0.683 mmol). After stirring at 50° C. for 30 minutes, the mixture was neutralized with HCl (0.176 mL of 1N solution in water, 0.176 mmol) and the solvents were evaporated. The residue chromatographed on silica gel (90:5:5 CHCl$_3$:EtOAc:MeOH) to give 22-7a or 22-7b (0.0246 g) as a white solid.

$^1$H NMR (400 MHz, CDCl$_3$): δ8.81 (s, 1H), 8.06 (m, 2H), 7.71 m, 2H), 7.56 (t, J=7.9 Hz, 1H), 6.38 (m, 2H), 3.82 (m, 1H), 2.85 (m, 5H), 2.75 (m, 1H), 2.58 (m, 1H), 1.96 (m, 2H), 1.84 (m, 1H), 1.67 (m, 2H), 1.38 (m, 6H). MS (M$^+$+H) 393.1.

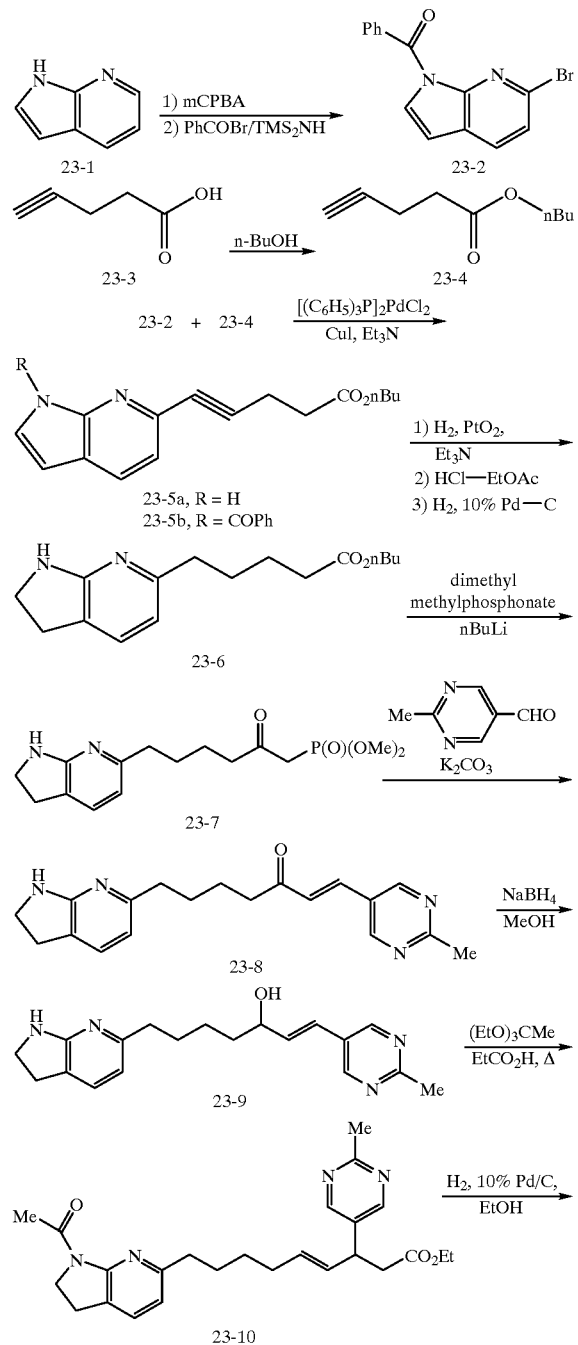

Scheme 23

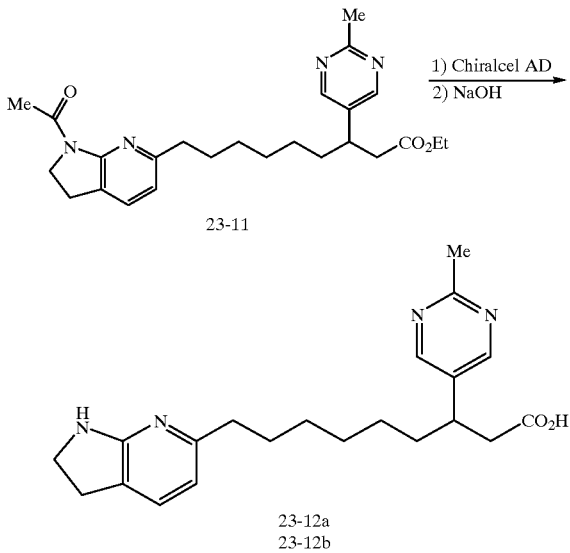

23-11

23-12a
23-12b

EXAMPLE 31

(R and S) 9-(2,3-Dihydro-1H-pyrrolo[2,3-b]pyridin-6-yl)-3-(2-methyl-pyrimidin-5-yl)-nonanoic acid Step A: 1H-Pyrrolo[2,3-b]pyridine 7-oxide A solution of 7-azaindole 22-1 (30.6 g, 259 mmol) in methylene chloride (300 mL) was treated with mCPBA (75.6 g, 285 mmol) at room temperature for 12 h. The reaction mixture was washed with saturated aqueous NaHCO$_3$ (3×100 mL), dried (Na$_2$SO$_4$), filtered, and concentrated in vacuo. Silica gel chromatography (100×250 mm silica, 10% to 50% EtOAc/hexanes) afforded 23.5 g of 1H-pyrrolo[2,3-b]pyridine 7-oxide as a white solid.

$^1$H NMR (300 MHz, CDCl$_3$) δ8.26 (d, 1H, J=6.2 Hz), 7.75 (d, 1H, J=7.9), 7.45 (d, 1H, J=3.4 Hz), 7.11 (dd, 1H, J=6.2, 7.9 Hz), 6.59 (d, 1H, J=3.4).

Step B: (6-Bromo-pyrrolo[2,3-b]pyridin-1-yl)-phenyl-methanone (23-2)

A benzene solution (25 mL) of the N-oxide was treated simultaneously with two separate solutions (PhCOBr, 6.39 g, 34.5 mmol in benzene and TMS$_2$NH 2.23 g, 13.8 mmol in benzene) via addition funnels at room temperature over a 1 h period. The solution was stirred overnight at room temperature. The solvent was removed in vacuo and the residue was purified by PCTLC (6 mm, 0–25% EtOAc-hexane) providing the 1.68 g (40% yield) of 23-2.

$^1$H NMR (300 MHz, CDCl$_3$) δ8.18 (m, 1H), 7.80 (m, 2H), 7.75 (m, 2H), 7.52 (m, 2H), 7.35 (m, 1H), 6.64 (d, 1H, J=3.9).

Step C: 5-(1H-Pyrrolo[2,3-b]pyridin-6-yl)-pent-4-ynoic acid butyl ester (23-5a) and 5-[6-(4-Methoxy-benzylamino)-pyridin-2-yl]-pent-4-Ynoic acid butyl ester (23-5b)

To a mixture of 23-2 (2.00 g, 6.64 mmol) and 23-4 (1.30 g, 7.97 mmol) in Et$_3$N (20 mL) at 0° was added CuI (0.032 g, 0.17 mmol). The solution was purged with argon and [(C$_6$H$_5$)$_3$P]$_2$PdCl$_2$ (0.093 g, 0.17 mmol) was added. After 1 h the cooling bath was removed and the solution was stirred for an additional 12 h. An additional equivalent of [(C$_6$H$_5$)$_3$P]$_2$PdCl$_2$ (0.093 g, 0.17 mmol) was added. Upon completion by tlc, the mixture was concentrated in vacuo. PCTLC (6 mm, 0–50% ethyl acetate/hexanes) provided 0.98 g of 23-5a and 1.13 g of 23-5b.

For 23-5a: $^1$H NMR (400 MHz, CDCl$_3$) δ7.87 (m, 1H), 7.38 (m, 2H), 7.20 (d, 1H, J=8.0 Hz), 6.50 (m, 1H), 4.13 (t, 2H), 2.82 (m, 2H), 2.70 (m, 2H), 1.63 (m, 2H), 1.38 (m, 2H), 0.92 (t, 3H).

For 23-5b: $^1$H NMR (400 MHz, CDCl$_3$) δ7.80 (m, 3H), 7.61 (m, 2H), 7.50 (m, 2H), 7.30 (d, 1H), 6.60 (d, 1H), 4.10 (t, 2H), 2.71 (m, 2H), 2.62 (m, 2H), 1.60 (m, 2H), 1.40 (m, 2H), 0.94 (t, 3H).

Step D: 5-(2,3-Dihydro-1H-pyrrolo[2,3-b]pyridin-6-yl)-pentanoic acid butyl ester (23-6)

A mixture of 23-5 (0.600 g, 2.20 mmol), Et$_3$N (0.31 mL, 2.20 mmol), and PtO$_2$ (0.060 g, 10% by weight) in EtOH (30 mL) was stirred under a balloon of hydrogen for 6 h. Filtration through celite, evaporative removal of the solvent, and PCTLC (6 mm, 10–80% EtOAc-hexane) afforded 0.384 g of the product of acetylene reduction.

$^1$H NMR (400 MHz, CDCl$_3$) δ9.22 (br s, 1H), 7.85 (d, 1H, J=8.0 Hz), 7.20 (m, 1H, obscured by CDCl$_3$), 6.96 (d, 1H, J=8.0), 6.57 (m, 1H), 4.10 (t, 2H), 2.89 (dd, 2H), 2.35 (dd, 2H), 1.82 (m, 2H), 1.73 (m, 2H), 1.59 (m, 2H), 1.37 (m, 2H), 0.93 (t, 3H).

This material (0.839 g, 3.06 mmol) was treated with a 4.0 M HCl-dioxane solution (5 mL) at room temperature for 1 h, then concentrated in vacuo. The residue was dissolved in dry EtOH (30 mL), degassed (Argon purge), treated with 10% Pd—C (0.21 mg, 25% by weight), degassed, and purged to hydrogen atmosphere (balloon—1 atmosphere). Upon completion as determined by liquid chromatography-mass spectroscopy (1 cms), the mixture was filtered through a Celite plug, washed with EtOH, concentrated in vacuo, and purified by PCTLC (4 mm, 0–10% MeOH-CHCl$_3$) providing 0.75 g (89% yield) of 23-6.

$^1$H NMR (400 MHz, CDCl$_3$) δ8.07 (br s, 1H), 7.30 (d, 1H, J=7.0 Hz), 6.33 (d, 1H, J=7.0), 4.08 (m, 2H), 3.92 (m, 2H), 3.15 (m, 2H), 2.74 (m, 2H), 2.36 (m, 2H), 1.82 (m, 2H), 1.69 (m, 2H), 1.61 (m, 2H), 1.39 (m, 2H), 0.93 (t, 3H).

Step E: [6-(2,3-Dihydro-1H-pyrrolo[2,3-b]pyridin-6-yl)-2-oxo-hexyl]-phosphonic acid dimethyl ester (23-7)

A solution of dimethyl methylphosphonate (1.35 g, 10.9 mmol) in anhydrous THF (20 mL) was cooled to −78° and treated dropwise with 2.6 M n-BuLi (4.1 mL). After stirring at −78° for 15 min, a solution of ester 23-6 (0.750 g, 2.71 mmol) in THF (10 mL) was added dropwise and the resulting solution stirred for 15 min at −78°, quenched with sat. NH$_4$Cl (25 mL), then extracted with CHCl$_3$ (1×25 mL), and the organic layer was applied to PCTLC (4 mm, 10% MeOH/CHCl$_3$) affording 0.79 g (89% yield) of 23-7.

$^1$H NMR (400 MHz, CDCl$_3$) δ7.19 (d, 1H), 6.38 (d, 1H), 4.40 (br s, 1H), 3.80 (s, 3H), 3.77 (s, 3H), 3.60 (m, 2H), 3.15 (m, 2H), 3.08 (m, 2H), 2.63 (m, 2H), 2.58 (m, 2H), 1.65 (m, 4H).

Step F: 7-(2,3-Dihydro-1H-pyrrolo[2,3-b]pyridin-6-yl)-1-(2-methyl-pyrimidin-5-yl)-hept-1-en-3-one (23-8)

To a solution of 23-7 (0.49 g, 1.5 mmol) and 2-methyl-pyrimidine-5-carbaldehyde (0.183 g, 1.5 mmol) in 15 mL DMF was added K$_2$CO$_3$ (0.310 g, 2.25 mmol). The mixture was stirred at ambient temperature for 2 hr and concentrated to a paste. The residue was purified by PCTLC (0–10% MeOH/CH$_2$Cl$_2$) which provided 0.400 g (83% yield) of 23-8.

$^1$H NMR (400 MHz, CDCl$_3$) δ8.79 (s, 2H), 7.42 (d, 1H, J=16.4 Hz), 7.18 (m, 1H), 6.81 (d, 1H, J=16.4 Hz), 6.38 (m, 1H), 4.39 (br s, 1H), 3.60 (m, 2H), 3.02 (m, 2H), 2.77 (s, 3H), 2.70 (d, 2H), 2.62 (d, 2H), 1.74 (m, 4H).

Step G: 7-(2,3-Dihydro-1H-pyrrolo[2,3-b]pyridin-6-yl)-1-(2-methyl-pyrimidin-5-yl)-hept-1-en-3-ol (23-9)

A solution of the enone 23-8 (0.400 g, 1.24 mmol) in THF:MeOH (5 mL each) was treated with NaBH$_4$ (0.047 g, 1.24 mmol). The reaction was quenched with acetone (2 mL), concentrated in vacuo, partitioned between water (5 mL) and chloroform (5 mL), and extracted with chloroform (4×10 mL). The organics were combined, dried (Na₂SO₄), and concentrated in vacuo to afford 0.387 g (96% yield) of 23-9.

¹H NMR (300 MHz, CDCl₃) 8.64 (s, 2H), 7.18 (d, 1H), 6.51 (m, 1H), 6.38 (m, 2H), 4.42 (br s, 1H), 4.39 (m, 1H), 3.79 (m, 2H), 3.60 (m, 4H), 2.72 (s, 3H), 2.60 (m, 2H), 1.74 (m, 4H).

Step H: 9-(1-Acetyl-2,3-dihydro-1H-pyrrolo[2,3-b]pyridin-6-yl)-3-(2-methyl-pyrimidin-5-yl)-non-4-enoic acid ethyl ester (23-10)

A solution of the allylic alcohol 23-9 (0.402 g, 1.24 mmol) in (EtO)₃CMe (20 mL) was treated with 1 uL propionic acid. The yellow solution was heated at reflux until complete by 1 cms. The solution was cooled to room temperature, concentrated, and purified by PCTLC (4 mm, 0–10% MeOH/CHCl₃) which provided 0.198 g (37% yield) of 23-10.

¹H NMR (400 MHz, CDCl₃) δ8.55 (s, 2H), 7.35 (d, 1H), 6.68 (d, 1H), 5.56 (m, 2H), 4.08 (m, 4H), 3.80 (m, 1H), 3.59 (m, 1H), 3.00 (m, 2H), 2.68 (m, 7H), 2.12 (m, 2H), 1.56 (m, 5H), 1.40 (m, 2H), 1.20 (t, 3H).

Step I: 9-(1-Acetyl-2,3-dihydro-1H-pyrrolo[2,3-b]pyridin-6-yl)-3-(2-methyl-pyrimidin-5-yl)-nonanoic acid ethyl ester (23-11)

To a solution of 23-10 (0.150 g, 0.34 mmol), ammonium formate (0.192 g, 3.09 mmol), and 10% Pd/C (0.150 g) in EtOH (25 mL) was refluxed for 15 minutes. Filtration through celite and evaporative removal of the solvent followed by purification by PCTLC (0–10% MeOH-CHCl₃) afforded 0.050 g of 23-11.

¹H NMR (400 MHz, CDCl₃) δ8.47 (s, 2H), 7.34 (d, 1H), 6.68 (d, 1H), 4.08 (m, 5H), 3.10 (m, 1H), 3.03 (m, 2H), 2.72 (s, 3H), 2.68 (s, 3H), 2.64 (m, 2H), 2.52 (m, 1H), 1.70 (m, 4H), 1.28 (m, 6H), 1.18 (t, 3H).

Step J: 3(R)- and 3(S)-9-(2,3-Dihydro-1H-pyrrolo[2,3-b]pyridin-6-yl)-3-(2-methyl-pyrimidin-5-yl)-nonanoic acid (23-12a and 23-12b)

A mixture of 23-11 (0.050 g, 0.11 mmol) in THF/H₂O 1:1(4 mL) was added NaOH (0.50 mL of 2 N solution in water, 1.03 mmol). After 48 hours, the mixture was neutralized with HCl (1.16 mL of 1N solution in water, 1.16 mmol) and the solvents were evaporated. PCTLC (1 mm, 0–10% MeOH/CHCl₃) provided 0.028 g of 23-12 (70% yield) as a white solid. 23-12 was resolved on a chiral AD column (2.54×20 cm), 8 ml/min, 70:20:10 Hexane (0.5% diethylamine):methanol (0.2% diethylamine): 1-propanol to give enantiomers 23-12a (faster-eluting) and 23-12b (slower eluting).

¹H NMR (400 MHz, CDCl₃) δ8.50 (s, 2H), 7.19 (d, 1H), 6.21 (d, 1H), 3.82 (m, 2H), 3.45 (br s, 1H), 3.42 (m, 2H), 3.25 (m, 1H), 3.06 (m, 2H), 2.70 (s, 3H), 2.65 (m, 1H), 2.61 (m, 1H), 2.55 (m, 2H), 1.84 (m, 1H), 1.62 (m, 1H), 1.23 (m, 6H).

Scheme 24

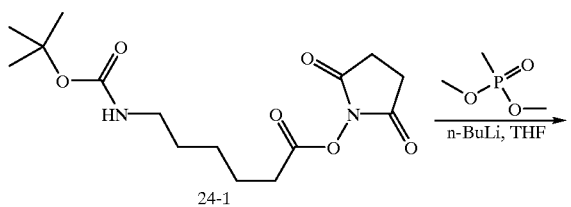

24-1

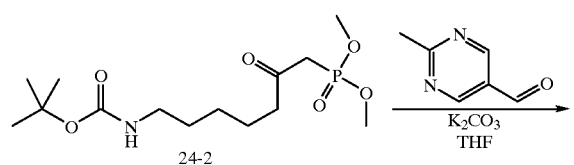

24-2

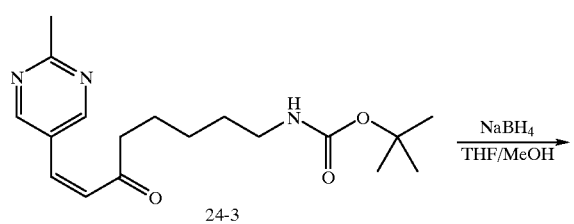

24-3

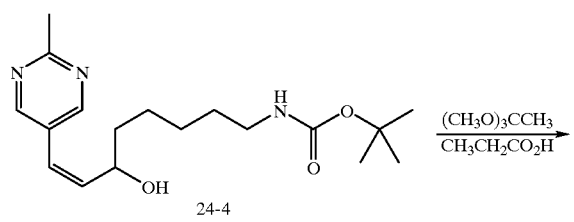

24-4

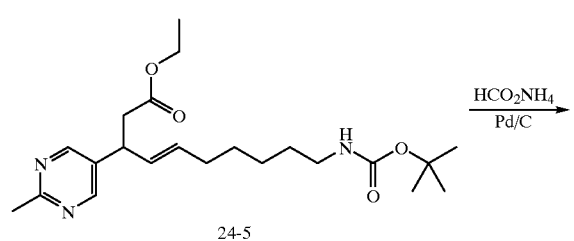

24-5

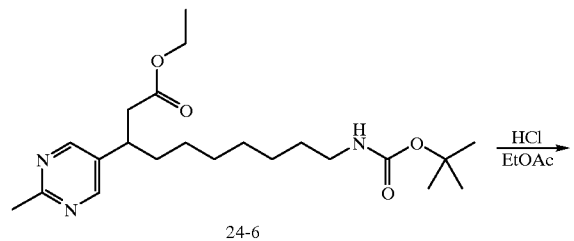

24-6

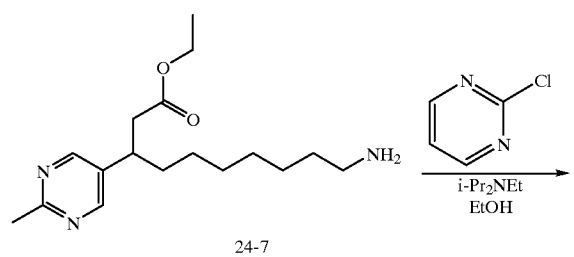

24-7

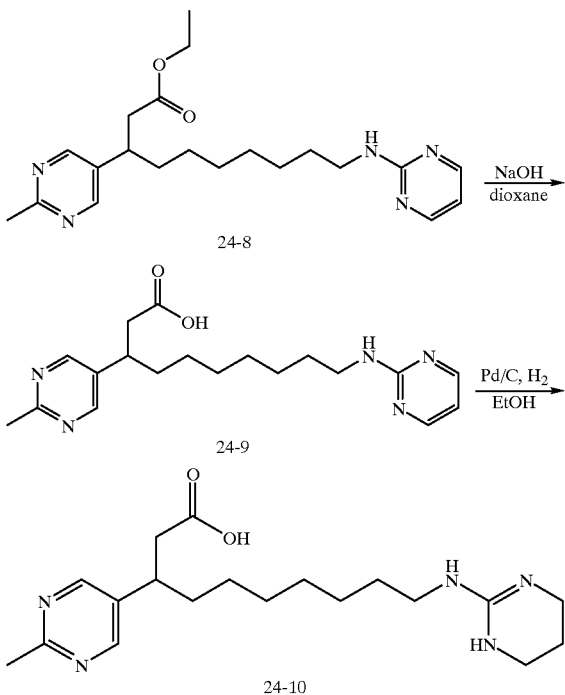

EXAMPLE 32

Step A (7-tert-Butoxycarbonylamino-2-oxo-heptyl)-phosphonic acid dimethyl ester (24-2)

A solution of dimethyl methylphosphonate (9.308 g, 75.01 mmol) in THF (30 mL) was cooled to −78 ° C. and treated with n-butyllithium (29.5 mL of 2.5 M). The reaction mixture was stirred at −78° C. for 10 min, followed by addition of 6-tert-butoxycarbonylamino-hexanoic acid 2,5-dioxo-pyrrolidin-1-yl ester (24-1) (5.060 g, 15.41 mmol) in THF (30 mL). After 15 min the reaction was quenched with aqueous NH$_4$Cl and allowed to warm to room temperature overnight. The water was extracted three times with ethyl acetate and the combined organics washed with brine and dried (Na$_2$SO$_4$). The solvent was removed in vacuo to afford the title compound 24-2 as a pale yellow oil (5.5 g).

Step B: [8-(2-Methyl-pyrimidin-5-yl)-6-oxo-oct-7-enyl]-carbamic acid tert-butyl ester (24-3)

A solution of 24-2 (3.13 g, 9.28 mmol), potassium carbonate (1.75 g, 12.6 mmol), and 2-methyl-pyrimidine-5-carbaldehyde (1.04 g, 8.51 mmol) in THF (20 mL) was warmed to 40° C. for 5 h. The mixture was diluted with water and extracted four times with ether. The combined organics were washed with brine and dried (Na$_2$SO$_4$). Purification via silica chromatography (hexane/ethyl acetate) afforded the title compound 24-3 (1.67 g).

$^1$H NMR (CDCl$_3$, 400 MHz) δ8.80 (s, 2H), 7.46 (d, 1H, J=16.3 Hz), 6.83 (d, 1H, J=16.3 Hz), 4.55 (s, 1H), 3.13 (m, 2H), 2.78 (s, 3H), 2.68 (t, 2H, J=7.3 Hz), 1.71 (m, 2H), 1.53 (m, 2H), 1.44 (s, 9H), 1.38 (m, 2H). ESLRMS m/e 334 g/mole (M$^+$, C$_{18}$H$_{27}$N$_3$O$_3$=334 g/mole.)

Step C: [6-Hydroxy-8-(2-methyl-pyrimidin-5-yl)-oct-7-enyl]-carbamic acid tert-butyl ester (24-4)

A solution of 24-3 (1.419 g, 4.255 mmol) in THF (10 mL) and methanol (5 mL) was treated with sodium borohydride (162.0 mg, 4.282 mmol) and stirred at room temperature (1 h). The reaction was quenched with acetone and the solvent removed in vacuo. Purification via silica chromatography (hexane/ethyl acetate) afforded the title compound 24-4 (1.0 g).

$^1$H NMR (CDCl$_3$, 400 MHz) δ8.63 (s, 2H), 6.51 (d, 1H, J=16.1 Hz), 6.33 (dd, 1H, J=5.9, 16.1 Hz), 4.53 (s, 1H), 4.31 (m, 1H), 3.13 (m, 2H), 2.73 (s, 3H), 1.96 (s, 1H), 1.64 (m, 2H), 1.44 (s, 9H), 1.43 (m, 6H). ESLRMS m/e 336 g/mole (M$^+$, C$_{18}$H$_{29}$N$_3$O$_3$=336 g/mole.)

Step D: 10-tert-Butoxycarbonylamino-3-(2-methyl-pyrimidin-5-yl)-dec-4-enoic acid ethyl ester (24-5)

A solution of 24-4 (1.00 g, 2.98 mmol) in triethyl orthoacetate (50 mL) was treated with propionic acid (2.5 mg, 0.034 mmol) and heated to 150 ° C. for 3 h. The reaction mixture was cooled to room temperature and treated with 1 N HCl and brine (75 mL each). The mixture was extracted with two portions of ethyl acetate. The combined organics were washed with brine and dried (Na$_2$SO$_4$). Purification via PCTLC (SiO$_2$, 4 mm, 10% EtOH; 90% CH$_2$Cl$_2$) afforded 24-5 (650 mg).

$^1$H NMR (CDCl$_3$, 400 MHz) δ8.49 (s, 2H), 5.52 (m, 2H), 4.54 (s, 1H), 4.08 (q, 2H, J=7.1 Hz), 3.80 (m, 1H), 3.09 (m, 2H), 2.71 (m, 5H), 2.02 (m, 2H), 1.37 (m, 15H), 1.19 (t,3H, J=7.1 Hz).

Step E: 10-tert-Butoxycarbonylamino-3-(2-methyl-pyrimidin-5-yl)-decanoic acid ethyl ester (24-6)

A solution of 24-5 (650 mg, 1.60 mmol), water (100 mg), ammonium formate (512 mg, 8.12 mmol), and 10% palladium on carbon (75 mg) in ethanol (40 mL) was heated to 90 ° C. for 1 hour. The reaction mixture was filtered through celite and the filtrate evaporated in vacuo to afford the title compound 24-6 (600 mg). The crude product was used directly in the next reaction. ESLRMS m/e 408 g/mole (M$^+$+H, C$_{22}$H$_{37}$N$_3$O$_4$=408 g/mole.)

Step F: 10-Amino-3-(2-methyl-pyrimidin-5-yl)-decanoic acid ethyl ester (24-7)

A solution of 24-6 (495 mg, 1.21 mmol) in ethyl acetate (3 mL) was treated with a saturated solution HCl in ethyl acetate (10 mL) at room temperature overnight. The solvent was removed in vacuo to afford 24-7 (390 mg). The crude product was used directly in the next reaction.

Step G: 3-(2-Methyl-pyrimidin-5-yl)-10-(pyrimidin-2-ylamino)-decanoic acid ethyl ester (24-8)

A solution of 24-7 (360 mg, 1.17 mmol), 2-chloropyrimidine (145 mg, 1.26 mmol), and N,N-diisopropylethylamine (456 mg, 3.53 mmol) in ethanol (5 mL) was heated to 65° C. in a sealed tube (4 days). The solvent was removed in vacuo and the residue diluted in aqueous sodium carbonate and extracted with two portions of dichloromethane. The combined organics were washed with brine and dried (Na$_2$SO$_4$). The solvent was removed in vacuo. PCTLC (SiO$_2$, 4mm, 1% NH$_4$OEt; 10% EtOH; 90% CH$_2$Cl$_2$) afforded 24-8 (150 mg). ESLRMS m/e 386 g/mole (M$^+$+H, C$_{21}$H$_{31}$N$_5$O$_2$=386 g/mole.)

Step H: 3-(2-Methyl-pyrimidin-5-yl)-10-(pyrimidin-2-ylamino)-decanoic acid (24-9)

A solution of 24-8 (170 mg, 0.441 mmol) in 1,4-dioxane (2 mL) was treated with 1M aqueous NaOH (1.50 mL) at room temperature (90 min). The reaction was neutralized with 1M aqueous HCl (1.50 mL) and the solvents were removed in vacuo. PCTLC (SiO$_2$, 2 mm, 10% MeOH; 25% EtOAc, 65% CHCl$_3$) afforded 24-9 (90 mg).

$^1$H NMR (CDCl$_3$, 500 MHz) δ8.53 (s, 2H), 8.23 (s, 2H), 6.61 (s, 1H), 6.51 (t, 1H, J=4.9 Hz), 3.39 (m, 2H), 3.16 (m, 1H), 2.64 (m, 5H), 1.81 (m, 1H), 1.60 (m, 3H), 1.31 (m, 8H). ESLRMS m/e 358 g/mole (M$^+$+H, C$_{19}$H$_{27}$N$_5$O$_2$=358 g/mole.); Exact MS (ES) (M$^+$+H, C$_{19}$H$_{27}$N$_5$O$_2$=358.2238), Found 358.2268

Step I: 3-(2-Methyl-pyrimidin-5-yl)-10-(1,4,5,6-tetrahydro-pyrimidin-2-ylamino)-decanoic acid (24-10)

A solution of 24-9 (47 mg, 0.131 mmol) in ethanol (1 mL) was treated with 10% palladium on carbon (7 mg) and hydrogen gas at one atmosphere (6 days). The reaction mixture was filtered through celite and the filtrate evaporated in vacuo. PCTLC (SiO$_2$, 1 mm, 2% AcOH; 18% MeOH; 80% CHCl$_3$) afforded 24-10 (37 mg).

$^1$H NMR (CDCl$_3$, 500 MHz) δ9.20 (s, 1H), 8.52 (s, 2H), 4.69 (s, 1H), 3.34 (m, 4H), 3.16 (m, 1H), 3.06 (m, 2H), 2.70 (s, 3H), 2.53 (m, 2H), 1.92 (m, 2H), 1.83 (m, 1H), 1.56 (m, 3H), 1.29 (m, 9H). ESLRMS m/e 362 g/mole (M$^+$+H, C$_{19}$H$_{31}$N$_5$O$_2$=362 g/mole.) HPLC (Vydac; C18; diameter= 4.6 mm; length=150 mm; gradient=H$_2$O [0.1% H$_3$PO$_4$]— CH$_3$CN, 95%–5%, 5%–95%, over 6 minutes, 2 ml/min flow rate) RT=2.52 min; focus=215 nm; 100% pure.

The following compounds whose structures are depicted below can also be prepared as described above and depicted in Schemes 1-24 using synthetic methodologies or variations thereon which are known and understood by those skilled in the art of synthetic organic chemistry:

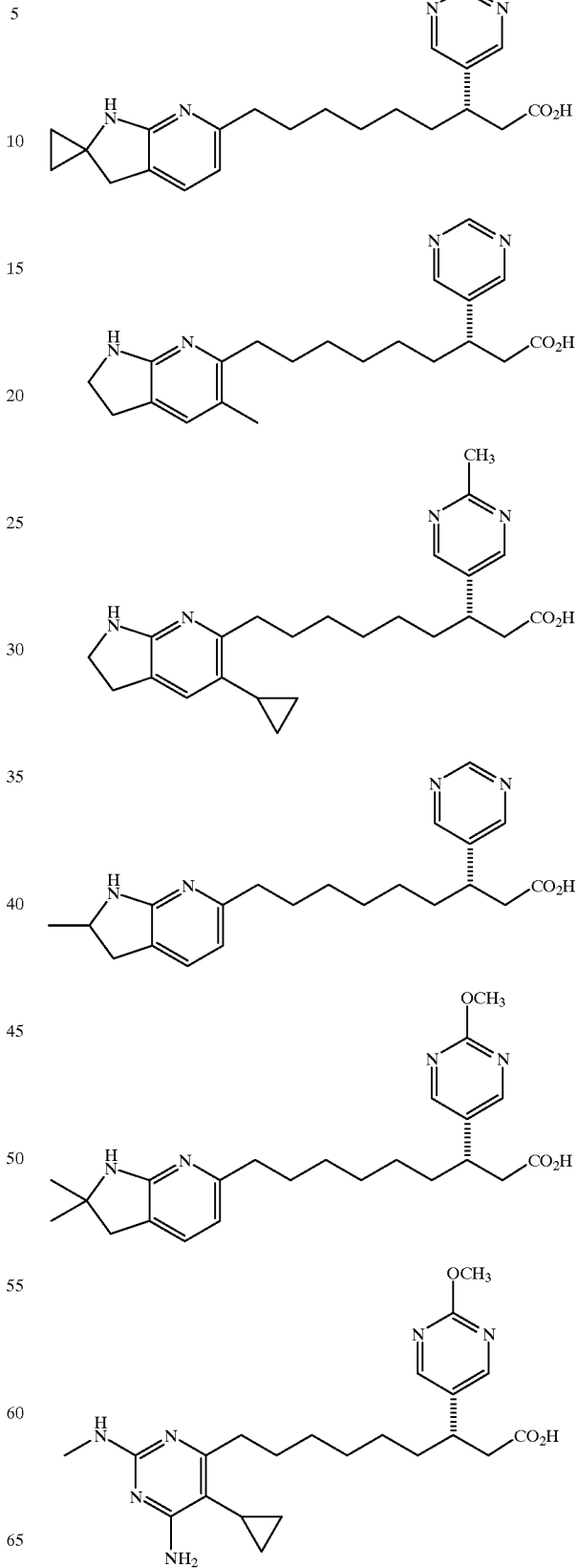

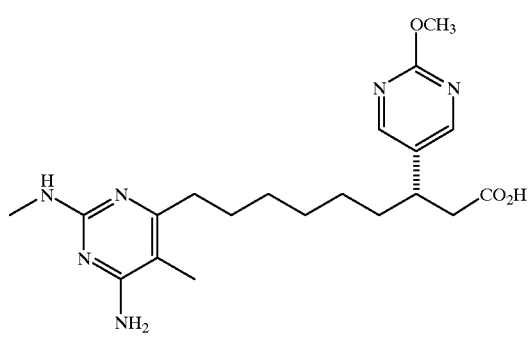
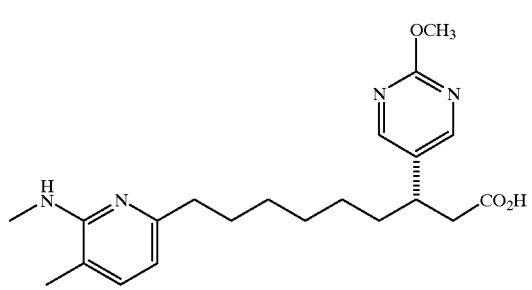
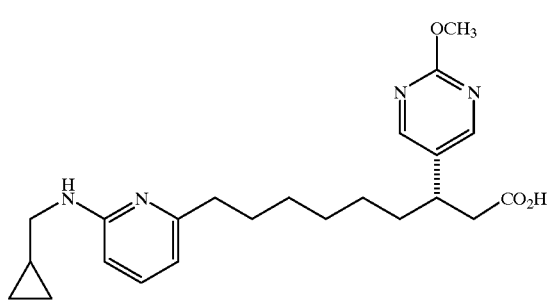
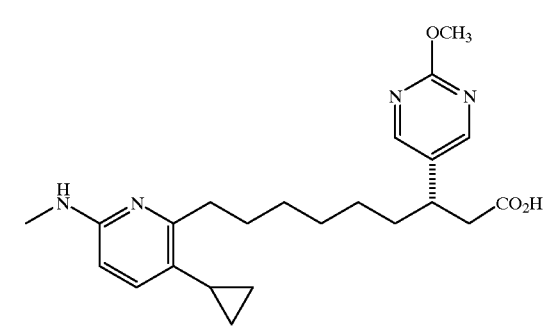
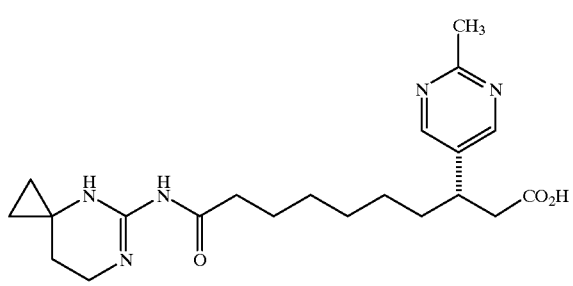
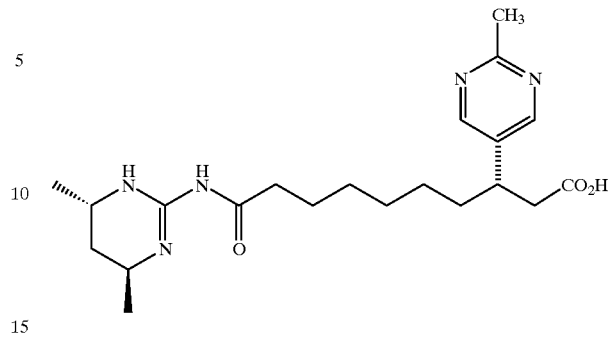
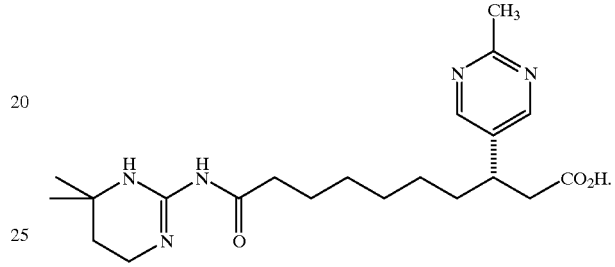
SCHEME A
Synthesis of Radioligand for SPAV3 Assay
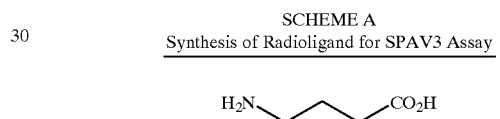
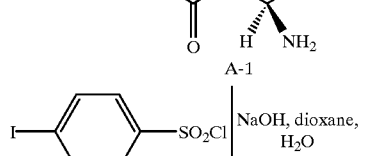
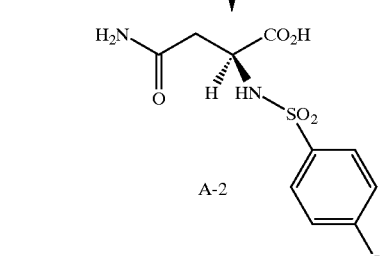
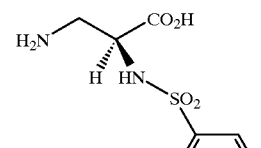

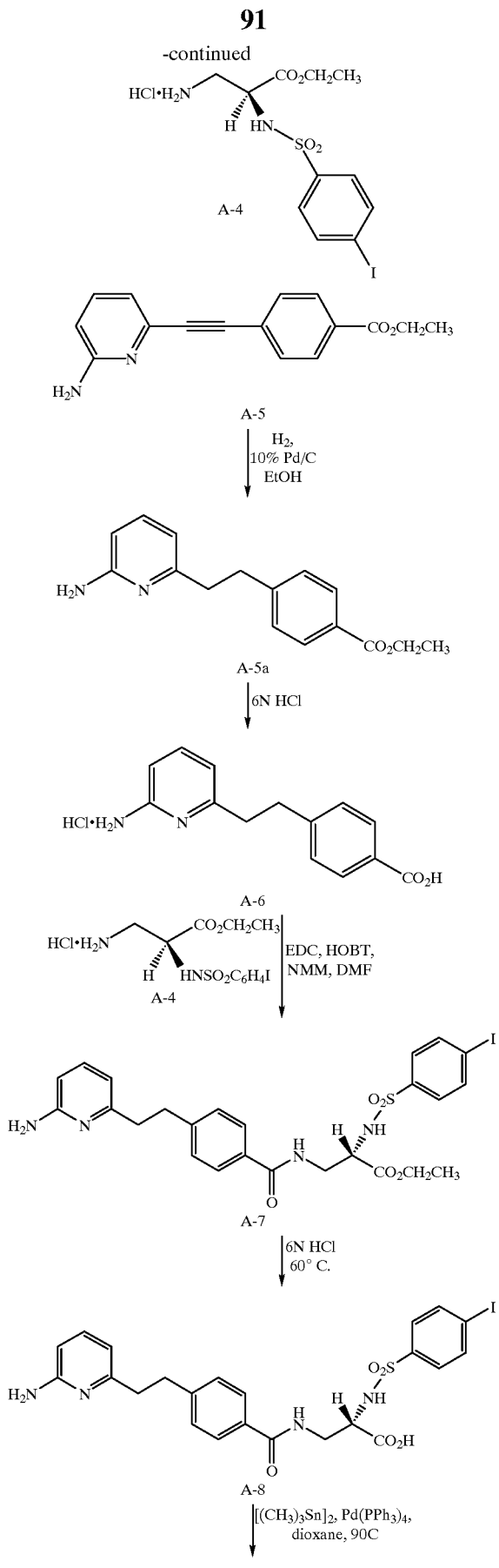

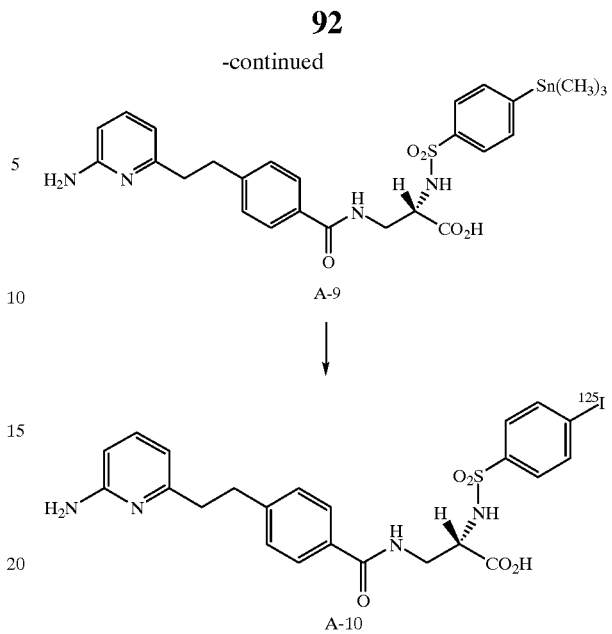

N-(4-Iodo-phenylsulfonylamino)-L-asparagine (A-2)

To a stirred solution of acid A-1 (4.39 g, 33.2 mmol), NaOH (1.49 g, 37.2 mmol), dioxane (30 ml) and H$_2$O (30 ml) at 0° C. was added pipsyl chloride (10.34 g, 34.2 mmol). After ~5 minutes, NaOH (1.49, 37.2 mmol) dissolved in 15 ml H$_2$O, was added followed by the removal of the cooling bath. After 2.0 h, the reaction mixture was concentrated. The residue was dissolved in H$_2$O (300 ml) and then washed with EtOAc. The aqueous portion was cooled to 0° C. and then acidified with concentrated HCl. The solid was collected and then washed with Et$_2$O to provide acid A-2 as a white solid.

$^1$H NMR (300 MHz, D$_2$O) δ7.86 (d, 2H, J=8 Hz ), 7.48 (d, 2H, J=8 Hz) 3.70 (m, 1H), 2.39 (m, 2H).

2(S)-(4-Iodo-phenylsulfonylamino)-β-alanine (A-3)

To a stirred solution of NaOH (7.14 g, 181.8 mmol) and H$_2$O (40 ml) at 0° C. was added Br$_2$ (1.30 ml, 24.9 mmol) dropwise over a ten minute period. After ~5 minutes, acid A-2 (9.9 g, 24.9 mmol), NaOH (2.00 g, 49.8 mmol) and H$_2$O (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid A-3 as a white solid.

$^1$H NMR (300 MHz, D$_2$O) δ8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (A-4)

HCl gas was rapidly bubbled through a suspension of acid A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.

$^1$H NMR (300 MHz, CD$_3$OD) δ7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyrimidin-6-yl)ethyl]benzoate (A-5a)

A mixture of ester A-5 (700 mg, 2.63 mmol), (for preparation, see: Scheme 29 of PCT International Application Publication No. WO 95/32710, published Dec. 7, 1995) 10% Pd/C (350 mg) and EtOH were stirred under 1 atm $H_2$. After 20 h, the reaction was filtered through a celite pad and then concentrated to provide ester A-5a as a brown oil.

TLC $R_f$=0.23 (silica, 40% EtOAc/hexanes) $^1$H NMR (300 MHz, $CDCl_3$) δ7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyrimidin-6-yl)ethyl]benzoic acid hydrochloride (A-6)

A suspension of ester A-5a (625 mg, 2.31 mmol) in 6N HCl (12 ml) was heated to 60° C. After ~20 h, the reaction was concentrated to give acid A-6 as a tan solid. $^1$H NMR (300 MHz, $CD_3OD$) δ7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodo-phenylsulfonylamino)-β-alanine (A-7)

A solution of acid 15-6 (400 mg, 1.43 mmol), amine A-4 (686 mg, 1.57 mmol), EDC (358 mg, 1.86 mmol), HOBT (252 mg, 1.86 mmol), NMM (632 μl, 5.72 mmol) in DMF (10 ml) was stirred for ~20 h. The reaction was diluted with EtOAc and then washed with sat. $NaHCO_3$, brine, dried ($MgSO_4$) and concentrated. Flash chromatography (silica, EtOAc then 5% isopropanol/EtOAc) provided amide A-7 as a white solid.

TLC $R_f$=0.4 (silica, 10% isopropanol/EtOAc) $^1$H NMR (300 MHz, $CD_3OD$) δ7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyrimidin-6-yl)ethyl]benzoyl-2(S)-(4-iodophenyl-sulfonylamino)-β-alanine (A-8)

A solution of ester A-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/$NH_4OH$/$H_2O$) provided acid A-8 as a white solid.

TLC $R_f$=0.45 (silica, 20:20:1:1 EtOAc/EtOH/$NH_4OH$/$H_2O$) $^1$H NMR (400 MHz, DMSO) δ8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyrimidin-6-yl)ethyl)benzoyl-2(S)-(4-trimethylstannyl-phenylsulfonylamino-β-alanine (A-9)

A solution of iodide A-8 (70 mg, 0.1178 mmol), [($CH_3$)$_3$Sn]$_2$ (49 μl, 0.2356 mmol), Pd(PPh$_3$)$_4$ (5 mg) and dioxane (7 ml) was heated to 90° C. After 2 h, the reaction was concentrated and then purified by preparative HPLC (Delta-Pak $C_{18}$ 15 μM 100 Å°, 40×100 mm; 95:5 then 5:95 $H_2O$/$CH_3CN$) to provide the trifluoroacetate salt. The salt was suspended in $H_2O$ (10 ml), treated with $NH_4OH$ (5 drops) and then lyophilized to provide amide A-9 as a white solid.

$^1$H NMR (400 MHz, DMSO) δ8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyrimidin-6-yl)ethyl]benzoyl-2(S)-4-$^{125}$iodo-phenylsulfonylamino-β-alanine (A-10)

An iodobead (Pierce) was added to a shipping vial of 5 mCi of Na$^{125}$I (Amersham, IMS30) and stirred for five minutes at room temperature. A solution of 0.1 mg of A-9 in 0.05 mL of 10% $H_2SO_4$/MeOH was made and immediately added to the Na$^{125}$I/iodobead vial. After stirring for three minutes at room temperature, approximately 0.04–0.05 mL of $NH_4OH$ was added so the reaction mixture was at pH 6–7. The entire reaction mixture was injected onto the HPLC for purification [Vydac peptide-protein C-18 column, 4.6×250 mm, linear gradient of 10% acetonitrile (0.1% (TFA):$H_2O$ (0.1% TFA) to 90% acetonitrile (0.1% TFA):$H_2O$ (0.1% TFA) over 30 minutes, 1 mL/min]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

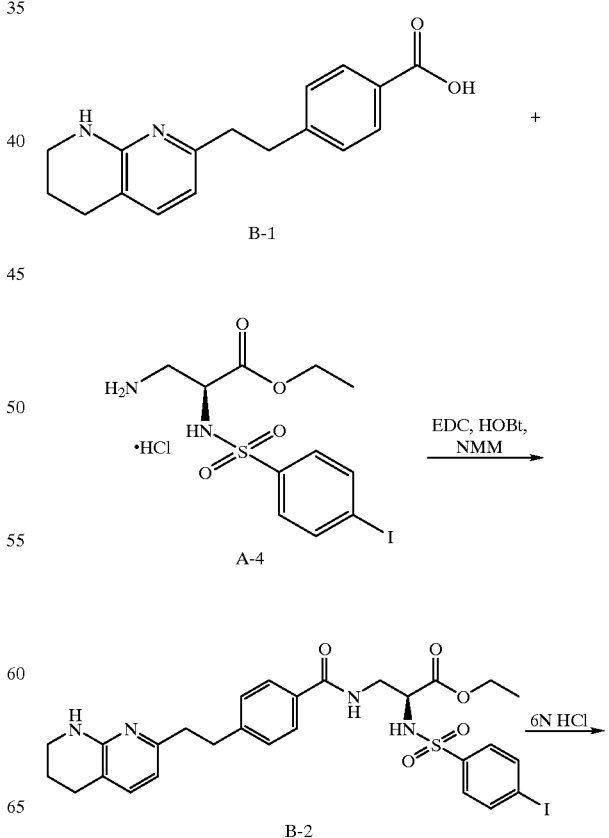

SCHEME B
Synthesis of Radioligand for SPAV5 Assay

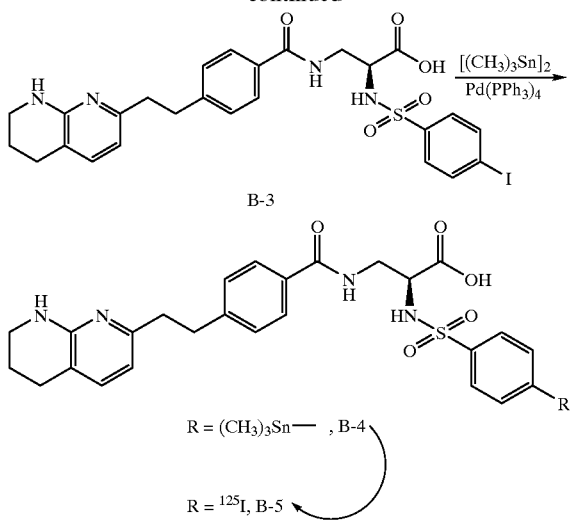

2(S)-(4-Iodo-benzenesulfonylamino)-3-{4-[2-(5,6,7,8-tetrahydro-[1,8]naphthyridin-2-yl)-ethyl]-benzoylamino}-propionic acid ethyl ester (B-2)

A mixture of B-1 (0.23 g, 0.72 mmol; for preparation see U.S. Pat. No. 5,741,796), A-4 (0.343 g, 0.792 mmol), EDC (0.179 g, 0.93 mmol), HOBT (0.126 g, 0.93 mmol), NMM (0.316 mL, 2.86 mmol) in acetonitrile (3 mL) and DMF (3 mL) was stirred for 2 hours at ambient temperature then diluted with ethyl acetate, washed with water, saturated aqueous NaHCO$_3$, and brine, dried over MgSO$_4$, and concentrated. The residue was chromatographed on silica gel (70:25:5 CHCl$_3$/EtOAc/MeOH) to give B-2 as a white solid.

TLC R$_f$=0.22 (silica, 70:25:5 CHCl$_3$/EtOAc/MeOH). $^1$H NMR (300 MHz, CDCl$_3$) δ7.79 (d, 2H, J=8 Hz), 7.63 (d, 2H, J=8 Hz), 7.54 (d, 2H, J=8 Hz), 7.27 (d, 2H, J=8 Hz), 7.04 (d, 1H, J=7 Hz), 6.60 (m, 1H), 6.29 (d, 1H, J=7 Hz), 4.83 (br s, 1H), 4.09 (m, 3H), 3.84 (m, 1H), 3.68 (m, 1H), 3.42 (m, 2H), 3.01 (m, 4H), 2.86 (m, 4H), 2.69 (t, 2H, J=6 Hz), 1.88 (m, 2H).

2(S)-(4-Iodo-benzenesulfonylamino)-3-{4-[2-(5,6,7,8-tetrahydro-[1,8]naphthyridin-2-yl)-ethyl]-benzoylamino}-propionic acid (B-3)

A mixture of B-2 (0.38 g, 0.573 mmol) and 6N HCl (50 mL) was stirred for 14 hours at 60° C. After cooling to room temperature, the mixture was concentrated, and the residue chromatographed on silica gel (25:10:1:1 to 15:10:1:1 EtOAc/EtOH NH$_4$OH/H$_2$O) to give B-3 as a white solid.

TLC R$_f$=0.43 (silica, 10:10:1:1 EtOAc/EtOH/NH$_4$OH/H$_2$O). $^1$H NMR (300 MHz, DMSO-d$_6$) δ8.42 (m, 1H), 7.79 (d, 2H, J=8 Hz), 7.63 (d, 2H, J=8 Hz), 7.44 (d, 2H, J=8 Hz), 7.27 (d, 2H, J=8 Hz), 7.10 (d, 1H, J=7 Hz), 6.58 (br s, 1H), 6.32 (d, 1H, J=7 Hz), 3.96 (m, 1H), 3.51 (m, 1H), 3.30 (m, 5H), 2.96 (m, 2H), 2.78 (m, 2H), 2.62 (m, 2H), 1.77 (m, 2H). HRMS: For C$_{26}$H$_{27}$IN$_4$O$_5$S, expected 635.0818, found 635.0831.

3-{4-[2-(5,6,7,8-Tetrahydro-[1,8]naphthyridin-2-yl)-ethyl]-benzoylamino}-2(S)-(4-trimethylstannyl-benzenesulfonylamino)-propionic acid (B-4)

A mixture of B-3 (0.10 g, 0.16 mmol), hexamethyldistannane (0.065 mL, 0.32 mmol), Pd(PPh$_3$)$_4$, and dioxane (10 mL) was stirred for one hour at 90° C. After cooling to room temperature, the mixture was concentrated, and the residue chromatographed on silica gel (50:10:1:1 to 25:10:1:1 EtOAc/EtOH/NH$_4$OH/H$_2$O) to give B-4 as a white solid.

TLC R$_f$=0.48 (silica, 15:10:1:1 EtOAc/EtOH/NH$_4$OH/H$_2$O). $^1$H NMR (300 MHz, DMSO-d$_6$) δ8.38 (m, 1H), 8.14 (m, 1H), 7.63 (m, 4H), 7.28 (d, 2H, J=8 Hz), 7.08 (d, 1H, J=7 Hz), 6.50 (br s, 1H), 6.28 (d, 1H, J=7 Hz), 3.96 (m, 1H), 3.48 (m, 1H), 3.31 (m, 5H), 2.96 (m, 2H), 2.78 (m, 2H), 2.62 (m, 2H), 1.77 (m, 2H), 0.28 (s, 9H). High resolution mass spectrum: For C$_{29}$H$_{36}$N$_4$O$_5$SSn, expected 665.1533 ($^{112}$Sn) and 673.1507 ($^{120}$Sn), found 665.1510 and 673.1505.

2(S)-(4-$^{125}$Iodo-benzenesulfonylamino)-3-{4-[2-(5,6,7,8-tetrahydro-[1,8]naphthyridin-2-yl)-ethyl]-benzoylamino}-propionic acid (B-5)

A stir bar, methanol (0.05 mL) and an iodobead (Pierce) were added to a shipping vial of Na$^{125}$I (10 mCi, Amersham, IMS300) and stirred for five minutes at room temperature. A solution of B-4 (~0.1 mg) in methanol (0.04 mL) was made and a portion (0.02 mL) was added to a mixture of H$_2$SO$_4$ (0.005 mL) in methanol (0.025 mL), and this solution was added immediately to the Na$^{125}$I/iodobead vial. After stirring for two minutes at room temperature, the reaction was quenched with NH$_4$OH (0.04–0.05 mL) and the entire reaction mixture was injected onto the HPLC for purification [Vydac peptide-protein C-18 column, 4.6×250 mm, linear gradient of 10% acetonitrile:H$_2$O (0.1% TFA) to 90% acetonitrile:H$_2$O (0.1% TFA) over 20 minutes, 1 mL/min]. The retention time of B-5 is 16 minutes under these conditions. Fractions containing the majority of the radioactivity were pooled, lyophilized and diluted with ethanol to give approximately 1 mCi of B-5, which coeluted on BPLC analysis with an authentic sample of B-3.

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure αvβ3 and αvβ5 binding and the bone resorption inhibiting activity of the compounds of the present invention are described below.

Bone Resorption-pit Assay

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur diaphysis are cut with a low speed diamond saw (Isomet, Beuler, Ltd., Lake Bluff, Ill.). Bone slices are pooled, placed in a 10% ethanol solution and refrigerated until further use.

Prior to experimentation, bovine bone slices are ultrasonicated twice, 20 minutes each in $H_2O$. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml αMEM, pH 6.9 containing 5% fetal bovine serum and 1% penicillin/streptomycin.

Long bones from 7–14 day old rabbits (New Zealand White Hare) are dissected, cleaned of soft tissue and placed in αMEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically ~$2 \times 10^7$ cells/ml). A cell suspension consisting of $5 \times 10^6$/ml in αMEM containing 5% fetal bovine serum, 10 nM $1,25(OH)_2D_3$, and pencillin-streptomycin is prepared. 200 ml aliquots are added to bovine bone slices (200 mm×6 mm) and incubated for 2 hrs. at 37° C. in a humidified 5% $CO_2$ atmosphere. The medium is removed gently with a micropipettor and fresh medium containing test compounds is added. The cultures are incubated for 48 hrs., and assayed for c-telopeptide (fragments of the a1 chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of $H_2O$, and the bone slices are then fixed for 20 minutes in 2.5% glutaraldehyde, 0.1 M cacodylate, pH 7.4. After fixation, any remaining cellular debris is removed by 2 min. ultrasonication in the presence of 0.25 M $NH_4OH$ followed by 2×15 min ultrasonication in $H_2O$. The bone slices are immediately stained for 6–8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting $IC_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp. 31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB Assay

Duong et al., *J. Bone Miner. Res.*, 8: S378 (1993), describes a system for expressing the human integrin αvβ3. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture 1. 175 μl TBS buffer (50 mM Tris.HCl pH 7.2, 150 mM NaCl, 1% BSA, 1 mM $CaCl_2$, 1 mM $MgCl_2$).
2. 25 ml cell extract (dilute with 100 mM octylglucoside buffer to give 2000 cpm/25 μl).
3. $^{125}$I-echistatin (25 μl/50,000 cpm) (see EP 382 451).
4. 25 μl buffer (total binding) or unlabeled echistatin (non-specific binding).

The reaction mixture was then incubated for 1 h at room temp. The unbound and the bound αvβ3 were separated by filtration using a Skatron Cell Harvester. The filters (prewet in 1.5% poly-ethyleneimine for 10 mins) were then washed with the wash buffer (50 mM Tris HCl, 1 mM $CaCl_2/MgCl_2$, pH 7.2). The filter was then counted in a gamma counter.

SPAV3 Assay

Materials

1. Wheat germ agglutinin Scintillation Proximity Beads (SPA): Amersham
2. Octylglucopyranoside: Calbiochem
3. HEPES: Calbiochem
4. NaCl: Fisher
5. $CaCl_2$: Fisher
6. $MgCl_2$: SIGMA
7. Phenylmethylsulfonylfluoride (PMSF): SIGMA
8. Optiplate: PACKARD
9. Compound A-10 (specific activity 500–1000 Ci/mmole)
10. test compound
11. Purified integrin receptor: αvβ3 was purified from 293 cells overexpressing αvβ3 (Duong et al., *J. Bone Min. Res.*, 8:S378, 1993) according to Pytela (Methods in Enzymology, 144:475, 1987)
12. Binding buffer: 50 mM HEPES, pH 7.8, 100 mM NaCl, 1 mM $Ca^{2+}/Mg^{2+}$, 0.5 mM PMSF
13. 50 mM octylglucoside in binding buffer: 50-OG buffer

Procedure

1. Pretreatment of SPA beads:
   500 mg of lyophilized SPA beads were first washed four times with 200 ml of 50-OG buffer and once with 100 ml of binding buffer, and then resuspended in 12.5 ml of binding buffer.
2. Preparation of SPA beads and receptor mixture
   In each assay tube, 2.5 μl (40 mg/ml) of pretreated beads were suspended in 97.5 μl of binding buffer and 20 ml of 50-OG buffer. 5 ml (~30 ng/μl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 μl of binding buffer and 25 μl of 50-OG buffer.
3. Reaction
   The following were sequentially added into Optiplate in corresponding wells:
   (i) Receptor/beads mixture (75 μl)
   (ii) 25 μl of each of the following: compound to be tested, binding buffer for total binding or A-8 for non-specific binding (final concentration 1 μM)
   (iii) A-10 in binding buffer (25 μl, final concentration 40 μM)
   (iv) Binding buffer (125 μl)
   (v) Each plate was sealed with plate sealer from PACKARD and incubated overnight with rocking at 4° C.

4. Plates were counted using PACKARD TOPCOUNT
5. % inhibition was calculated as follows:
   A=total counts
   B=nonspecific counts
   C=sample counts
   % inhibition=[{(A-B)-(C-B)}/(A-B)]/(A-B)×100

Ocform Assay

Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 mm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1 \times 10^6$ cells/mL. 50 µL was added to each well of 1.8 cells to yield 50,000 cells/well and 1,25-dihydroxy-vitamin $D_3$ ($D_3$) was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing $D_3$ to quadruplicate wells. Compounds were added again after 48 h with fresh medium containing D3. After an additional 48 h., the medium was removed, cells were fixed with 10% formaldehyde in phosphate buffered saline for 10 minutes at room temperature, followed by a 1–2 minute treatment with ethanol: acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells was counted in each well.

SPAV5 Assay

Materials

1. Wheat germ agglutinin Scintillation Proximity Beads (SPA): Amersham
2. Octylglucopyranoside and Phorbo-12-myristate-13-acetate (PMA): Calbiochem
3. Tris-HCl, NaCl and $CaCl_2$: Fisher
4. Minimum Essential Media (MEM): Gibco/BRL
5. Fetal bovine serum (FBS): Hyclone
6. $MgCl_2$, $MnCl_2$, and Phenylmethylsulfonylfluoride (PMSF): SIGMA
7. Protease inhibitor cocktail tablets: Boehringer Mannheim.
8. Optiplate-96 wells: PACKARD
9. B-5 was used as radiolabeled ligand (specific activity 500–1000 Ci/mmole) and cold (2.5 µM) was used to achieve 100% inhibition.
10. Test compound.
11. HEK293 cells overexpressing $\alpha_v\beta_5$ integrins (Simon et al., J. Biol. Chem. 272, 29380–29389, 1997) are cultured in 150 mm dishes in 10% FBS/MEM media (Gibco/BRL).
12. Lysis buffer: 100 mM octylglucopyranoside, 50 mM Tris, pH 7.5, 100 mM NaCl, 1 mM $CaCl_2$, 1 mM $MgCl_2$, 0.5 mM PMSF and protease inhibitors (1 tablet/50 ml buffer).
13. Binding buffer: 50 mM Tris, pH 7.5, 100 mM NaCl, 1 mM $CaCl_2$ 1 MM $MgCl_2$ and 1 mM $MnCl_2$
14. 50 mM octylglucopyranoside in binding buffer: 50-OG buffer Procedure 1. $\alpha_v\beta_5$-cell lysates: HEK 293 cells expressing $\alpha_v\beta_5$ integrins were cultured until confluent. Cells were then starved overnight in media containing 0.5% FBS, followed by treatment with 100 nM PMA for 20 min. Cells were washed 2 times with cold phosphate buffer saline (4° C.) and solubilized in lysis buffer for 30 min on ice. Lysates were clarified using a Beckman JA-20 at 20,000× g. Protein concentration of clarified lysates was determined using a micro BCA kit (Pierce) and stored in aliquots at 80° C.
2. Pretreatment of SPA beads:
   500 mg of lyophilized SPA beads were first washed four times with 200 ml of 50-OG buffer and once with 100 ml of binding buffer, and then resuspended in 12.5 ml of binding buffer.
3. Preparation of SPAV5 binding reaction
   To each assay well, the following were sequentially added into Optiplate plates:
   (i) Binding buffer to make up final volume of 125 µl per well.
   (ii) 3 µl (120 µg/well) of pretreated beads diluted with 22 µl of 50-OG Buffer
   (iii) 15 µg of $\alpha_v\beta_5$-cell lysate proteins.
   (iv) at 50,000 cpm.
   (v) 25 µl of graded concentrations of test compound.
   (vi) Each plate was sealed with plate sealer from PACKARD and incubated overnight with rocking at 4° C.
4. Plates were counted using PACKARD TOPCOUNT microplate scintillation counter.
5. % Inhibition was calculated as follows:
   A=total counts (binding of receptor to B-5)
   B=nonspecific counts (binding of receptor to B-5 in the presence of 2.5 µM cold ligand)
   C=counts from receptor binding to test compound % inhibition=[{(A-B)-(C-B)}/(A-B)]/(A-B)×100
   $IC_{50}$ of test compound was calculated as 50% of inhibition.

Example of a Pharmaceutical Formulation

As a specific embodiment of an oral composition, 100 mg of any of the compounds of the present invention are formulated with sufficient finely divided lactose to provide a total amount of 580 to 590 mg to fill a size O hard gel capsule.

Representative compounds of the present invention were tested and found to bind to human αvβ3 integrin. These compounds were generally found to have $IC_{50}$ values less than about 100 nM in the SPA assay.

Representative compounds of the present invention were tested and generally found to inhibit ≧50% the attachment of αvβ5 expressing cells to plates coated with vitronectin at concentrations of about 1 µM.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound selected from the group consisting of:
   3-(5-3,4-Dihydro-2H-pyrido[3,2-b][1,4]oxazin-6-yl-pentanoylamino)-3-(quinolin-3-yl)-propionic acid;
   3-(5-3,4-Dihydro-2H-pyrido[3,2-b][1,4]oxazin-6-yl-pentanoylamino)-3(R)-(quinolin-3-yl)-propionic acid;
   3-(5-3,4-Dihydro-2H-pyrido[3,2-b][1,4]oxazin-6-yl-pentanoylamino)-3(S)-(quinolin-3-yl)-propionic acid;
   3-(Quinolin-3-yl)-3-(5-1,2,3,4-tetrahydro-pyrido[2,3-b]pyrazin-6-yl-pentanoylamino)-propionic acid;
   3(R)-(Quinolin-3-yl)-3-(5-1,2,3,4-tetrahydro-pyrido[2,3-b]pyrazin-6-yl-pentanoylamino)-propionic acid;
   3(S)-(Quinolin-3-yl)-3-(5-1,2,3,4-tetrahydro-pyrido[2,3-b]pyrazin-6-yl-pentanoylamino)-propionic acid;
   9-(6-Methylamino-pyridin-2-yl)-3-(pyrimidin-5-yl)-nonanoic acid;
   9-(6-Methylamino-pyridin-2-yl)-3(R)-(pyrimidin-5-yl)-nonanoic acid;
   9-(6-Methylamino-pyridin-2-yl)-3(S)-(pyrimidin-5-yl)-nonanoic acid;
   9-(6-Methylamino-pyridin-2-yl)-3-(2-methyl-pyrimidin-5-yl)-nonanoic acid;
   9-(6-Methylamino-pyridin-2-yl)-3(R)-(2-methyl-pyrimidin-5-yl)-nonanoic acid;
   9-(6-Methylamino-pyridin-2-yl)-3(S)-(2-methyl-pyrimidin-5-yl)-nonanoic acid;
   3-(2-Methoxy-pyrimidin-5-yl)-9-(6-methylamino-pyridin-2-yl)-nonanoic acid;
   3(R)-(2-Methoxy-pyrimidin-5-yl)-9-(6-methylamino-pyridin-2-yl)-nonanoic acid;
   3(S)-(2-Methoxy-pyrimidin-5-yl)-9-(6-methylamino-pyridin-2-yl)-nonanoic acid;
   3-(2-Ethoxy-pyrimidin-5-yl)-9-(6-methylamino-pyridin-2-yl)-nonanoic acid;
   3(R)-(2-Ethoxy-pyrimidin-5-yl)-9-(6-methylamino-pyridin-2-yl)-nonanoic acid;
   3(S)-(2-Ethoxy-pyrimidin-5-yl)-9-(6-methylamino-pyridin-2yl)-nonanoic acid;
   9-(6-Ethylamino-pyridin-2-yl)-3-(2-methyl-pyrimidin-5-yl)-nonanoic acid;
   9-(6-Ethylamino-pyridin-2-yl)-3(R)-(2-methyl-pyrimidin-5-yl)-nonanoic acid;
   9-(6-Ethylamino-pyridin-2-yl)-3(S)-(2-methyl-pyrimidin-5-yl)-nonanoic acid;
   3-(2-Methoxy-pyrimidin-5-yl)-9-(6-ethylamino-pyridin-2-yl)-nonanoic acid;
   3(R)-(2-Methoxy-pyrimidin-5-yl)-9-(6-ethylamino-pyridin-2-yl)-nonanoic acid;
   3(S)-(2-Methoxy-pyrimidin-5-yl)-9-(6-ethylamino-pyridin-2-yl)-nonanoic acid;
   3-(2-Ethoxy-pyrimidin-5-yl)-9-(6-ethylamino-pyridin-2-yl)-nonanoic acid;
   3(R)-(2-Ethoxy-pyrimidin-5-yl)-9-(6-ethylamino-pyridin-2-yl)-nonanoic acid;
   3(S)-(2-Ethoxy-pyrimidin-5-yl)-9-(6-ethylamino-pyridin-2-yl)-nonanoic acid;
   3-9-(6-Methylamino-pyridin-2-yl)-3-quinoxalin-2-yl)-nonanoic acid;
   3(R)-9-(6-Methylamino-pyridin-2-yl)-3-quinoxalin-2-yl)-nonanoic acid;
   3(S)-9-(6-Methylamino-pyridin-2-yl)-3-quinoxalin-2-yl)-nonanoic acid;
   3-9-(2,3Dihydro-1H-pyrrolo[2,3-b]pyridin-6-yl)-3-(2-methyl-pyrimidin-5-yl)-nonanoic acid;
   3-(R)-9-(2,3Dihydro-1H-pyrrolo[2,3-b]pyridin-6-yl)-3-(2-methyl-pyrimidin-5-yl)-nonanoic acid; and
   3(S)-9-(2,3Dihydro-1H-pyrrolo[2,3-b]pyridin-6-yl)-3-(2-methyl-pyrimidin-5-yl)-nonanoic acid; or a pharmaceutically acceptable salt thereof.

* * * * *